(12) United States Patent
Zhuang et al.

(10) Patent No.: US 11,788,123 B2
(45) Date of Patent: Oct. 17, 2023

(54) SYSTEMS AND METHODS FOR HIGH-THROUGHPUT IMAGE-BASED SCREENING

(71) Applicant: President and Fellows of Harvard College, Cambridge, MA (US)

(72) Inventors: Xiaowei Zhuang, Lexington, MA (US); George Alexander Emanuel, Cambridge, MA (US); Jeffrey R. Moffitt, Boston, MA (US)

(73) Assignee: President and Fellows of Harvard College, Cambridge, MA (US)

(*) Notice: Subject to any disclaimer, the term of this patent is extended or adjusted under 35 U.S.C. 154(b) by 561 days.

(21) Appl. No.: 16/616,833

(22) PCT Filed: May 25, 2018

(86) PCT No.: PCT/US2018/034651
§ 371 (c)(1),
(2) Date: Nov. 25, 2019

(87) PCT Pub. No.: WO2018/218150
PCT Pub. Date: Nov. 29, 2018

(65) Prior Publication Data
US 2020/0095630 A1    Mar. 26, 2020

Related U.S. Application Data

(60) Provisional application No. 62/511,920, filed on May 26, 2017.

(51) Int. Cl.
*C12Q 1/6841* (2018.01)
*C40B 30/04* (2006.01)
*C40B 70/00* (2006.01)

(52) U.S. Cl.
CPC ........... *C12Q 1/6841* (2013.01); *C40B 30/04* (2013.01); *C40B 70/00* (2013.01); *C12Q 2525/161* (2013.01); *C12Q 2563/179* (2013.01); *C12Q 2565/514* (2013.01)

(58) Field of Classification Search
CPC ........... C12Q 1/6841; C12Q 2525/161; C12Q 2563/179; C12Q 2565/514; C40B 30/04; C40B 70/00
See application file for complete search history.

(56) References Cited

U.S. PATENT DOCUMENTS

| | | |
|---|---|---|
| 4,888,278 A | 12/1989 | Singer et al. |
| 5,382,511 A | 1/1995 | Stapleton |
| 5,501,954 A | 3/1996 | Mahr et al. |
| 5,563,033 A | 10/1996 | Lawrence et al. |
| 5,563,056 A | 10/1996 | Swan et al. |
| 6,001,568 A | 12/1999 | Chetverin et al. |
| 6,150,516 A | 11/2000 | Brenner et al. |
| 6,232,067 B1 | 5/2001 | Hunkapiller et al. |
| 6,444,421 B1 | 9/2002 | Chung et al. |
| 6,524,798 B1 | 2/2003 | Goldbard et al. |
| 6,620,584 B1 | 9/2003 | Chee et al. |
| 7,033,754 B2 | 4/2006 | Chee et al. |
| 7,122,319 B2 | 10/2006 | Liu et al. |
| 7,226,734 B2 | 6/2007 | Chee et al. |
| 7,368,265 B2 | 5/2008 | Brenner et al. |
| 7,455,971 B2 | 11/2008 | Chee et al. |
| 7,473,767 B2 | 1/2009 | Dimitrov |
| 7,499,806 B2 | 3/2009 | Kermani et al. |
| 7,629,125 B2 | 12/2009 | Sood et al. |
| 7,727,721 B2 | 6/2010 | Pierce et al. |
| 7,776,613 B2 | 8/2010 | Zhuang et al. |
| 7,785,790 B1 | 8/2010 | Church et al. |
| 7,807,447 B1 | 10/2010 | Shoemaker et al. |
| 7,838,302 B2 | 11/2010 | Zhuang et al. |
| 7,906,285 B2 | 3/2011 | Drmanac |
| 7,910,304 B2 | 3/2011 | Drmanac |
| 7,981,604 B2 | 7/2011 | Quake |
| 8,460,865 B2 | 6/2013 | Chee et al. |
| 8,564,792 B2 | 10/2013 | Zhuang et al. |
| 8,741,566 B2 | 6/2014 | Winther et al. |
| 9,163,283 B2 | 10/2015 | Chee et al. |
| 9,201,063 B2 | 12/2015 | Sood et al. |
| 9,359,636 B2 | 6/2016 | Tuschl et al. |
| 9,371,598 B2 | 6/2016 | Chee |

(Continued)

FOREIGN PATENT DOCUMENTS

| | | |
|---|---|---|
| CN | 1570140 A | 1/2005 |
| CN | 1898397 A | 1/2007 |

(Continued)

OTHER PUBLICATIONS

U.S. Appl. No. 15/329,683, filed Jan. 27, 2017, Zhuang et al.
U.S. Appl. No. 16/253,919, filed Jan. 22, 2019, Zhuang et al.
U.S. Appl. No. 16/347,874, filed May 7, 2019, Zhuang et al.
U.S. Appl. No. 16/348,071, filed May 7, 2019, Zhuang et al.
CN 201580052678.7, Jan. 16, 2019, Chinese Office Action.
CN 201580052678.7, Nov. 14, 2019, Chinese Office Action.
EP 15827358.1, Feb. 6, 2018, Extended European Search Report.
EP 15827358.1, Sep. 26, 2018, European Office Action.
EP 15827358.1, Oct. 16, 2019, European Office Action.
PCT/US2015/042556, Oct. 6, 2015, Invitation to Pay Additional Fees.

(Continued)

*Primary Examiner* — David C Thomas
(74) *Attorney, Agent, or Firm* — Wolf, Greenfield & Sacks, P.C.

(57) ABSTRACT

The present invention generally relates to imaging cells, for example, to determine phenotypes and/or genotypes in populations of cells. The cells may be exposed to a nucleic acid comprising an identification portion, which may be used to distinguish the cells from each other. In some embodiments, the cells may be exposed to a nucleic acid comprising an expression portion. The identification portion, the expression portion, or both may be introduced into the genome of a host organism or as exogenous materials, e.g. plasmids.

13 Claims, 12 Drawing Sheets

Specification includes a Sequence Listing.

(56) References Cited

U.S. PATENT DOCUMENTS

| | | | |
|---|---|---|---|
| 9,518,982 B2 | 12/2016 | Sood et al. |
| 9,556,473 B2 | 1/2017 | Bernitz et al. |
| 9,677,125 B2 | 6/2017 | Sood et al. |
| 9,712,805 B2 | 7/2017 | Zhuang et al. |
| 9,778,154 B2 | 10/2017 | Gradinaru et al. |
| 9,850,536 B2 | 12/2017 | Oliphant et al. |
| 9,944,972 B2 | 4/2018 | Yin et al. |
| 10,073,035 B2 | 9/2018 | Zhuang et al. |
| 10,190,151 B2 | 1/2019 | Yin et al. |
| 10,227,639 B2 | 3/2019 | Levner et al. |
| 10,240,146 B2 | 3/2019 | Zhuang et al. |
| 10,266,876 B2 | 4/2019 | Cai et al. |
| 10,267,808 B2 | 4/2019 | Cai |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,563,257 B2 | 2/2020 | Boyden et al. |
| 10,870,846 B2 | 12/2020 | Scott et al. |
| 10,961,566 B2 | 3/2021 | Chee |
| 11,021,737 B2 | 6/2021 | Church et al. |
| 11,078,520 B2 | 8/2021 | Church et al. |
| 11,098,303 B2 | 8/2021 | Zhuang et al. |
| 2002/0058248 A1 | 5/2002 | Kolanko et al. |
| 2002/0094116 A1 | 7/2002 | Frost et al. |
| 2003/0104428 A1 | 6/2003 | Branton et al. |
| 2003/0148335 A1 | 8/2003 | Shen et al. |
| 2004/0002095 A1 | 1/2004 | Liu et al. |
| 2004/0053300 A1 | 3/2004 | Soderlund et al. |
| 2004/0081979 A1 | 4/2004 | Knezevic et al. |
| 2004/0091880 A1 | 5/2004 | Wiebusch et al. |
| 2004/0137488 A1 | 7/2004 | Kenten et al. |
| 2004/0248144 A1 | 12/2004 | Mir |
| 2005/0042612 A1 | 2/2005 | Hubbard et al. |
| 2005/0064435 A1 | 3/2005 | Su et al. |
| 2005/0106594 A1 | 5/2005 | Ellington et al. |
| 2005/0123959 A1 | 6/2005 | Williams et al. |
| 2005/0176023 A1 | 8/2005 | Ramon et al. |
| 2005/0233318 A1 | 10/2005 | Chee et al. |
| 2006/0024711 A1 | 2/2006 | Lapidus et al. |
| 2006/0051798 A1 | 3/2006 | Mirken et al. |
| 2006/0141502 A1 | 6/2006 | Capodieci et al. |
| 2006/0177833 A1 | 8/2006 | Brenner |
| 2006/0228733 A1 | 10/2006 | Pierce et al. |
| 2006/0275782 A1 | 12/2006 | Gunderson et al. |
| 2006/0292559 A1 | 12/2006 | Reddy et al. |
| 2007/0020650 A1 | 1/2007 | Kahvejian |
| 2007/0048759 A1 | 3/2007 | Luo et al. |
| 2007/0190543 A1 | 8/2007 | Livak |
| 2008/0050731 A1 | 2/2008 | Agnew et al. |
| 2008/0269068 A1 | 10/2008 | Church et al. |
| 2008/0299565 A1 | 12/2008 | Schneider et al. |
| 2009/0105082 A1 | 4/2009 | Chetverin et al. |
| 2009/0131269 A1 | 5/2009 | Martin et al. |
| 2010/0323348 A1 | 1/2010 | Hamady et al. |
| 2010/0216146 A1 | 8/2010 | Williams et al. |
| 2010/0291557 A1 | 11/2010 | Livak et al. |
| 2010/0304994 A1 | 12/2010 | Wu et al. |
| 2011/0002530 A1 | 1/2011 | Zhuang et al. |
| 2011/0086774 A1 | 4/2011 | Dunaway |
| 2011/0092381 A1 | 4/2011 | Sood et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0035065 A1 | 2/2012 | Smolke et al. |
| 2012/0040397 A1 | 2/2012 | Luo et al. |
| 2012/0088235 A1 | 4/2012 | Kokoris et al. |
| 2012/0100540 A1 | 4/2012 | Wu et al. |
| 2012/0129165 A1 | 5/2012 | Raj et al. |
| 2012/0208724 A1 | 8/2012 | Steemers et al. |
| 2012/0270214 A1 | 10/2012 | Bernitz et al. |
| 2013/0096014 A1 | 4/2013 | Anderson et al. |
| 2013/0190196 A1 | 7/2013 | Onderdonk et al. |
| 2013/0261019 A1 | 10/2013 | Lin et al. |
| 2014/0024024 A1 | 1/2014 | Sood et al. |
| 2014/0031243 A1 | 1/2014 | Cai et al. |
| 2015/0087001 A1 | 3/2015 | Gradinaru et al. |
| 2015/0105298 A1 | 4/2015 | Czaplinski |
| 2015/0144490 A1 | 5/2015 | Deisseroth et al. |
| 2015/0211023 A1 | 7/2015 | Shiboleth et al. |
| 2015/0267251 A1 | 9/2015 | Cai et al. |
| 2016/0010054 A1 | 1/2016 | Gartner et al. |
| 2016/0116384 A1 | 4/2016 | Chen et al. |
| 2016/0153005 A1 | 6/2016 | Cong et al. |
| 2016/0161472 A1 | 6/2016 | Jungmann et al. |
| 2016/0194701 A1 | 7/2016 | Beechem et al. |
| 2016/0257997 A1 | 9/2016 | Stender et al. |
| 2016/0304952 A1 | 10/2016 | Boyden et al. |
| 2016/0305856 A1 | 10/2016 | Stuart et al. |
| 2016/0369329 A1 | 12/2016 | Cai et al. |
| 2016/0370295 A1 | 12/2016 | Zhuang et al. |
| 2017/0212986 A1 | 7/2017 | Zhuang et al. |
| 2017/0220733 A1 | 8/2017 | Zhuang et al. |
| 2017/0327876 A1 | 11/2017 | Khafizov et al. |
| 2018/0142286 A1 | 5/2018 | Dunaway et al. |
| 2018/0230226 A1 | 8/2018 | Podack et al. |
| 2019/0233812 A1 | 8/2019 | Zhuang et al. |
| 2019/0264270 A1 | 8/2019 | Zhuang et al. |
| 2019/0276881 A1 | 9/2019 | Zhuang et al. |
| 2020/0064340 A1 | 2/2020 | Jungmann et al. |
| 2020/0399689 A1 | 12/2020 | Luo et al. |
| 2022/0025442 A1 | 1/2022 | Zhuang et al. |
| 2022/0064697 A1 | 3/2022 | Zhuang et al. |
| 2022/0205983 A1 | 6/2022 | Zhuang et al. |

FOREIGN PATENT DOCUMENTS

| | | | |
|---|---|---|---|
| CN | 1950516 A | 4/2007 | |
| CN | 102149829 A | 8/2011 | |
| CN | 102171234 A | 8/2011 | |
| CN | 103649331 A | 3/2014 | |
| CN | 103703143 A | 4/2014 | |
| CN | 103890586 A | 6/2014 | |
| CN | 104350372 A | 2/2015 | |
| CN | 105164279 A | 12/2015 | |
| CN | 105274144 A | 1/2016 | |
| CN | 105531377 A | 4/2016 | |
| CN | 105556309 A | 5/2016 | |
| EP | 1064399 A2 | 1/2001 | |
| EP | 1 196 630 B1 | 11/2008 | |
| EP | 2 082 226 B1 | 8/2011 | |
| WO | WO 1999/031277 A1 | 6/1999 | |
| WO | WO-9931277 A1 * | 6/1999 | ......... C12N 15/1079 |
| WO | WO 01/23614 A1 | 4/2001 | |
| WO | WO 02/00336 A2 | 1/2002 | |
| WO | WO 03/02979 A2 | 1/2003 | |
| WO | WO 2003/003810 A2 | 1/2003 | |
| WO | WO 2003/003810 A3 | 1/2003 | |
| WO | WO 2005/047535 A1 | 5/2005 | |
| WO | WO 2005/066368 A2 | 7/2005 | |
| WO | WO 2006/003423 A2 | 1/2006 | |
| WO | WO 2007/001986 A2 | 1/2007 | |
| WO | WO 2008/064067 A2 | 5/2008 | |
| WO | WO 2008/091296 A2 | 7/2008 | |
| WO | WO 2008/108843 A2 | 9/2008 | |
| WO | WO 2009/085218 A1 | 7/2009 | |
| WO | WO 2011/038403 A1 | 3/2011 | |
| WO | WO 2011/094669 A1 | 8/2011 | |
| WO | WO 2011/112634 A2 | 9/2011 | |
| WO | WO 2011/143583 A1 | 11/2011 | |
| WO | WO 2012/049316 A1 | 4/2012 | |
| WO | WO 2012/110899 A2 | 8/2012 | |
| WO | WO 2013/090360 A2 | 6/2013 | |
| WO | WO 2014/028538 A2 | 2/2014 | |
| WO | WO 2015/127183 A2 | 8/2015 | |
| WO | WO 2015/160690 A1 | 10/2015 | |
| WO | WO-2015160690 A1 * | 10/2015 | ....... C07K 14/43595 |
| WO | WO 2016/018960 A1 | 2/2016 | |
| WO | WO 2016/018963 A9 | 2/2016 | |
| WO | WO 2016/028843 A2 | 2/2016 | |
| WO | WO-2016018960 A1 * | 2/2016 | ............ C07H 21/02 |
| WO | WO-2017143155 A2 * | 8/2017 | ......... C12N 15/1065 |
| WO | WO 2018/026873 A1 | 2/2018 | |

(56) References Cited

FOREIGN PATENT DOCUMENTS

| WO | WO 2018/089438 A1 | 5/2018 |
|---|---|---|
| WO | WO 2018/089445 A1 | 5/2018 |
| WO | WO 2018/218150 A1 | 11/2018 |

OTHER PUBLICATIONS

PCT/US2015/042556, Dec. 18, 2015, International Search Report and Written Opinion.
PCT/US2015/042556, Feb. 9, 2017, International Preliminary Report on Patentability.
EP 15828133.7, Feb. 5, 2018, Extended European Search Report.
EP 15828133.7, Sep. 24, 2018, European Office Action.
PCT/US2015/042559, Oct. 9, 2015, International Search Report and Written Opinion.
PCT/US2015/042559, Feb. 9, 2017, International Preliminary Report on Patentability.
PCT/US17/60570, Feb. 5, 2018, International Search Report and Written Opinion.
PCT/US17/60570, May 23, 2019, International Preliminary Report on Patetability.
PCT/US18/34651, Aug. 6, 2018, Invitation to Pay Additional Fees.
PCT/US18/34651, Oct. 4, 2018, International Search Report and Written Opinion.
PCT/US18/34651, Dec. 5, 2019, International Preliminary Report on Patentability.
PCT/US17/60558, Feb. 5, 2018, International Search Report and Written Opinion.
PCT/US17/60558, May 23, 2019, International Preliminary Report on Patentability.
Chinese Office Action dated Jan. 16, 2019 for Application No. 201580052678.7.
Chinese Office Action dated Nov. 14, 2019 for Application No. 201580052678.7.
Extended European Search Report dated Feb. 6, 2018 for Application No. 15827358.1.
European Office Action dated Sep. 26, 2018 for Application No. 15827358.1.
European Office Action dated Oct. 16, 2019 for Application No. 15827358.1.
Invitation to Pay Additional Fees mailed Oct. 6, 2015 for Application No. PCT/US2015/042556.
International Search Report and Written Opinion dated Dec. 18, 2015 for Application No. PCT/US2015/042556.
International Preliminary Report on Patentability dated Feb. 9, 2017 for Application No. PCT/US2015/042556.
Extended European Search Report dated Feb. 5, 2018 for Application No. 15828133.7.
European Office Action dated Sep. 24, 2018 for Application No. 15828133.7.
International Search Report and Written Opinion dated Oct. 9, 2015 for Application No. PCT/US2015/042559.
International Preliminary Report on Patentability dated Feb. 9, 2017 for Application No. PCT/US2015/042559.
International Search Report and Written Opinion dated Feb. 5, 2018 for Application No. PCT/US 17/60570.
International Preliminary report on Patentability dated May 23, 2019 for Application No. PCT/US17/60570.
Invitation to Pay Additional Fees mailed Aug. 6, 2018 for Application No. PCT/US18/34651.
International Search Report and Written Opinion dated Oct. 4, 2018 for Application No. PCT/US18/34651.
International Preliminary Report on Patentability dated Dec. 5, 2019 for Application No. PCT/US18/34651.
International Search Report and Written Opinion dated Feb. 5, 2018 for Application No. PCT/US17/60558.
International Preliminary report on Patentability dated May 23, 2019 for Application No. PCT/US17/60558.

Binladen et al., The use of coded PCR primers enables high-throughput sequencing of multiple homolog amplification products by 454 parallel sequencing. PLoS One. Feb. 14, 2007;2(2):e197.
Chen et al., Expansion microscopy. Science. Jan. 2015; 347(6221):543-548.
Chen et al., Nanoscale imaging of RNA with expansion microscopy. Nature Methods. 2016; 13:679-684.
Chen et al., Spatially resolved, highly multiplexed RNA profiling in single cells. Science. Apr. 24, 2015;348(6233):aaa6090. doi: 10.1126/science.aaa6090. Epub Apr. 9, 2015.
Darouich et al., Use of DOP-PCR for amplification and labeling of BAC DNA for FISH. Biotech Histochem. Feb. 2012;87(2):117-21. doi: 10.3109/10520295.2011.559175.
Fakruddin et al., Nucleic acid sequence based amplification (NASBA)-prospects and applications. Int. J. Life Sci. Pharm. Res. Mar. 2012; 2(1): L106-L121.
Levsky et al., Single-cell gene expression profiling. Science. Aug. 2, 2002; 297:836-840.
Lubeck et al., Single-cell in situ RNA profiling by sequential hybridization. Nature Methods. Apr. 2014; 11(4): 360-1.
Lubeck et al., Single-cell in situ RNA profiling by sequential hybridization. Nature Methods. Apr. 2014; 11(4): 360-1. Supplementary Information.
Moffitt et al., High-performance multiplexed fluorescence in situ hybridization in culture and tissue with matrix imprinting and clearing. Proc Natl Acad Sci U S A. Dec. 13, 2016; 113(50):14456-14461. Epub Nov. 22, 2016.
Moffitt et al., High-throughput single-cell gene-expression profiling with multiplexed error-robust fluorescence in situ hybridization. Proc Natl Acad Sci U S A. Sep. 27, 2016; 113(39): 11046-51. doi: 10.1073/pnas.1612826113. Epub Sep. 13, 2016.
Moffitt et al., RNA Imaging with Multiplexed Error-Robust Fluorescence In Situ Hybridization (MERFISH). Methods Enzymol. 2016;572:1-49. doi: 10.1016/bs.mie.2016.03.020. Epub Apr. 27, 2016.
Player et al., Single-copy gene detection using branched DNA (bDNA) in situ hybridization. The Journal of Histochemistry & Cytochemistry. 2001; 49(5): 603-611.
Shiels et al., RNA-DNA hybrids containing damaged DNA are substrates for RNase H. Bioorg Med Chem Lett. Oct. 8, 2001;11(19):2623-6.
Tillberg et al., Protein-retention expansion microscopy of cells and tissues labeled using standard fluorescent proteins and antibodies. Nat. Biotechnol. 2016; 34(9):987-992.
Zhen et al., Poly-fish: A technique of repeated hybridizations that improves cytogenetic analysis of fetal cells in maternal blood. Prenatal Diagnosis. Mar. 21, 1998; 18: 1181-1185.
European Office Action dated Oct. 16, 2020 for Application No. EP 15827358.1.
European Office Action dated Apr. 8, 2022 for Application No. EP 15827358.1.
Chinese Office Action dated Mar. 5, 2020 for Application No. CN 201580051029.5.
Chinese Office Action dated Aug. 19, 2020 for Application No. CN 201580051029.5.
Chinese Office Action dated Feb. 1, 2021 for Application No. CN 201580051029.5.
European Office Action dated Aug. 19, 2020 for Application No. 15828133.7.
European Office Action dated Feb. 16, 2022 for Application No. EP 15828133.7.
Extended European Search Report dated May 20, 2020 for Application No. EP 17869122.6.
Chinese Office Action dated Jan. 6, 2022 for Application No. CN 201780082227.7.
Chinese Office Action dated Jul. 5, 2022 for Application No. CN 201780082227.7.
Extended European Search Report dated Jul. 20, 2020 for Application No. EP 17869515.1.
European Office Action dated Aug. 9, 2021 for Application No. EP 17869515.1.
Invitation to Pay Additional Fees for Application No. PCT/US2019/065857 mailed Mar. 3, 2020.

(56) References Cited

OTHER PUBLICATIONS

International Search Report and Written Opinion for Application No. PCT/US2019/065857 dated May 1, 2020.
International Preliminary Report on Patentability dated Jun. 24, 2021 for Application No. PCT/US2019/065857.
International Search Report and Written Opinion for Application No. PCT/US20/28632 dated Jul. 16, 2020.
International Preliminary Report on Patentability dated Oct. 28, 2021 for Application No. PCT/US2020/28632.
International Search Report and Written Opinion dated Mar. 22, 2021 for Application No. PCT/US2020/061254.
International Preliminary Report on Patentability dated Jun. 2, 2022 for Application No. PCT/US2020/061254.
International Preliminary Report on Patentability dated Jul. 14, 2022 for Application No. PCT/US2020/065797.
Babcock, Multiplane and Spectrally-Resolved Single Molecule Localization Microscopy with Industrial Grade CMOS cameras. Scientific Reports. Jan. 2018;8:1726. 8 pages.
Baeissa et al., DNA-Functionalized Monolithic Hydrogels and Gold Nanoparticles for Colorimetric DNA Detection. Applied Materials & Interfaces. Nov. 2010; 2(12):3594-3600. doi:10.1021/am100780d.
Beliveau et al., Versatile design and synthesis platform for visualizing genomes with Oligopaint FISH probes. Proc Natl Acad Sci U S A. Dec. 26, 2012;109(52):21301-6. doi: 10.1073/pnas.1213818110. Epub Dec. 11, 2012.
Chen et al., RNA imaging. Spatially resolved, highly multiplexed RNA profiling in single cells. Science. 2015;348(6233):aaa6090.
Chen et al., Supplemental Material for Expansion microscopy. Science. Jan. 2015; 347(6221):1-18.
Chung et al., CLARITY for mapping the nervous system [published correction appears in Nat Methods. Oct. 2013;10(10):1035]. Nat Methods. 2013;10(6):508-513.
Datlinger et al., Pooled CRISPR screening with single-cell transcriptome readout. Nat Methods. Mar. 2017;14(3):297-301. doi: 10.1038/nmeth.4177. Epub Jan. 18, 2017.
Dixit et al., Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Epstein et al., Reutilization of Previously Hybridized Slides for Flourescence In Situ Hybridization. Cytometry. 1995;21:378-381.
Gunderson et al., Decoding Randomly Ordered DNA Arrays. Methods. 2004;14:870-877.
Koshkin et al., LNA (locked nucleic acids: Synthesis, of the adenine, cytosine, guanine, 5-methylcytosine, thymine and uracil bicyclonucleside monomers, oligomerization and unprecedented nucleic acid recognition. Tetrahedron. 1998;54:3607-30.
Libus et al., Quantification of cDNA generated by reverse transcription of total RNA provides a simple alternative tool for quantitative RT-PCR normalization. Biotechniques. Aug. 2006;41(2):156, 158, 160 passim. doi: 10.2144/000112232.
May, How many species are there on Earth? Science. Sep. 16, 1988;241(4872):1441-9. doi: 10.1126/science.241.4872.1441.
Nilsson et al. Comparison of fungal 80 S ribosomes by cryo-EM reveals diversity in structure and conformation of rRNA expansion segments. J Mol Biol. Jun. 1, 2007;369(2):429-38. doi: 10.1016/j.jmb.2007.03.035. Epub Mar. 20, 2007.
Philippova et al., Polymer Gels. In: Polymer Science: A Comprehensive Reference (vol. 1). 2012. Chapter 1.13: 339-366.
Prabhat et al., Simultaneous imaging of different focal planes in fluorescence microscopy for the study of cellular dynamics in three dimensions. IEEE Trans Nanobioscience. Dec. 2004;3(4):237-42. doi: 10.1109/tnb.2004.837899.
Thomsen et al., Dramatically improved RNA in situ hybridization signals using LNA-modified probes.RNA. Nov. 2005;11(11):1745-8. doi: 10.1261/rna.2139705. Epub Sep. 21, 2005.
Tsanov et al., smiFISH and FISH-quant—a flexible single RNA detection approach with super-resolution capability. Nucleic Acids Res. 2016;44(22):e165.
Valczi et al., Sensitive and specific detection of microRNAs by northern blot analysis using LNA-modified oligonucleotide probes. Nucleic Acids Res. Dec. 14, 2004;32(22):e175. doi: 10.1093/nar/gnh171.
Ward, The Human Cell Atlas; An International Effort. AltTox.org. Oct. 31, 2016. Available at: http://alttox.org/the-human-cell-atlas-an-international-effort/ [Last accessed Jan. 21, 2022].
Wienholds et al., MicroRNA expression in zebrafish embryonic development. Science. Jul. 8, 2005;309(5732):310-1. doi: 10.1126/science.1114519. Epub May 26, 2005.
Yang et al., Single-cell phenotyping within transparent intact tissue through whole-body clearing. Cell. 2014;158(4):945-958.
Zhang et al., Tandem Spinach Array for mRNA Imaging in Living Bacterial Cells. Sci Rep. 2015;5:17295.
Chinese Office Action dated Nov. 25, 2022 for Application No. 201780082228.1.
European Office Action dated Mar. 24, 2023 for Application No. EP 17869122.6.
Extended European Search Report dated Oct. 10, 2022 for Application No. 19894439.9.
Extended European Search Report dated Dec. 9, 2022 for Application No. 20791572.9.
International Search Report and Written Opinion dated Mar. 24, 2021 for Application No. PCT/US2020/065797.
Albrecht et al., Photo-and electropatterning of hydrogel-encapsulated living cell arrays. Lab Chip. Jan. 2005;5(1):111-8. doi: 10.1039/b406953f. Epub Nov. 24, 2004.
Bintu et al., Super-resolution chromatin tracing reveals domains and cooperative interactions in single cells. Science. Oct. 26, 2018;362(6413):eaau1783. doi: 10.1126/science.aau1783.
Cai, Turning single cells into microarrays by super-resolution barcoding. Brief Funct Genomics. Mar. 2013;12(2):75-80. doi: 10.1093/bfgp/els054. Epub Nov. 22, 2012.
Carmona et al., LncRNA Jpx induces Xist expression in mice using both trans and cis mechanisms. PLoS Genet. May 7, 2018;14(5):e1007378. doi: 10.1371/journal.pgen.1007378. eCollection May 2018.
Chung et al., Structural and molecular interrogation of intact biological systems. Nature. May 16, 2013;497(7449):332-7. doi: 10.1038/nature12107. Epub Apr. 10, 2013. Author manuscript provided. 23 pages.
Church, Proposal for a Center for the determination of the Causal Transcriptional Consequences of Human Genetic Variation (CTCHGV). Department of Genetics, Harvard Medical School. May 25, 2009. 64 pages.
Cremer et al., Multicolor 3D Fluorescence In Situ Hybridization for Imagin Interphase Chromosomes. Methods Mol Biol. The Nucleus: vol. 1: Nuclei and Subnuclear Components. 2008;463:205-39. doi: 10.1007/978-1-59745-406-3_15.
Cui et al., Beyond quantification: in situ analysis of transcriptome and pre-mRNA alternative splicing at the nanoscale. Wiley Interdiscip Rev Nanomed Nanobiotechnol. Jul. 2017;9(4). doi: 10.1002/wnan.1443. Epub Nov. 4, 2016. 19 pages.
Fan et al., Highly parallel genomic assays. Review. Nat Rev Genet. Aug. 2006;7(8):632-44. doi: 10.1038/nrg1901.
Femino et al., Visualization of Single RNA Transcripts in Situ. Science. Apr. 24, 1998;280(5363):585-90. doi: 10.1126/science.280.5363.585.
Goransson, Readout Strategies for Biomolecular Analyses. Digital Comprehensive Summaries of Uppsala Dissertations from the Faculty of Science and Technology 563, Uppsala Universitet. 2008:42 pages.
Kanagawa, Bias and artifacts in multitemplate polymerase chain reactions (PCR). J Biosci Bioeng. 2003;96(4):317-23. doi: 10.1016/S1389-1723(03)90130-7.
Ke et al., In situ sequencing for RNA analysis in preserved tissue and cells. Nat Methods. Sep. 2013;10(9):857-60. doi: 10.1038/nmeth.2563. Epub Jul. 14, 2013.
Kuhn et al., Poly(A) Tail Length is Controlled by the Nuclear Poly(A)-binding Protein Regulating the Interaction between Poly(A) Polymerase and the Cleavage and Polyadenylation Specificity Factor. The Journal of Biological Chemistry. Aug. 21, 2009;284(34):22803-22814.

(56) References Cited

OTHER PUBLICATIONS

Larsson et al., In situ genotyping individual DNA molecules by target-primed rolling-circle amplification of padlock probes. Nat Methods. Dec. 2004;1(3):227-32. doi: 10.1038/nmeth723. Epub Nov. 18, 2004.

Lubeck et al., Single cell in situ RNA profiling by sequential hybridization. Nat Methods. Apr. 2014;11(4):360-361. doi:10.1038/nmeth.2892. Author manuscript provided. 3 pages.

Lubeck et al., Single Cell Systems Biology by Super-resolution imaging and combinatorial Labeling. Nat Methods. Jun. 3, 2012;9(7):743-8. doi: 10.1038/nmeth.2069. Author manuscript provided. 18 pages.

Mali et al., Barcoding cells using cell-surface programmable DNA-binding domains. Nat Methods. May 2013;10(5):403-6. doi: 10.1038/nmeth.2407. Epub Mar. 17, 2013. Author manuscript provided. 12 pages.

Mitra et al., In situ localized amplification and contact replication of Many individual DNA Molecules, Nucleic Acids Res. Dec. 15, 1999;27(24):e34. doi: 10.1093/nar/27.24.e34.

Müller et al., A Nonredundant Multicolor Bar Code as a Screening Tool for Rearrangements in Neoplasia, Genes, Chromosomes & Cancer. Jan. 1, 2004;39(1):59-70.

Murgha et al., Large-Scale Generation of Synthetic DNA Libraries: Sequence-Specific Priming of Reverse Transcription, PhD Dissertation. University of Michigan. 2012. 199 pages.

Namekawa et al., Detection of nascent RNA, single-copy DNA and protein localization by immunoFISH in mouse germ cells and preimplantation embryos. Nat Protoc. Mar. 2011;6(3):270-84. doi: 10.1038/nprot.2010.195. Epub Feb. 10, 2011. Author manuscript provided. 36 pages.

Polz et al., Bias in template-to-product ratios in multitemplate PCR. Appl Environ Microbiol. Oct. 1998;64(10):3724-30. doi: 10.1128/AEM.64.10.3724-3730.1998.

Reinartz et al., Technique Review: Massively parallel signature sequencing (MPSS) as a tool for in-depth quantitaive gene expression profiling in all organisms. Brief Funct Genomic Proteomic. Feb. 2002;1(1):95-104. doi: 10.1093/bfgp/1.1.95.

Steemers et al., Whole genome genotyping technologies on the BeadArray TM Platform. Biotechnol J. Jan. 2007;2(1):41-9. doi: 10.1002/biot.200600213.

Su et al., Genome-Scale Imaging of the 3D Organization and Transcriptional Activity of Chromatin. Cell. Sep. 17, 2020;182(6):1641-1659.e26. doi: 10.1016/j.cell.2020.07.032. Epub Aug. 20, 2020.

Torgersen et al., Localization of mRNAs and Proteins in Methyl Methacrylate-embedded Tissues. Journal of Histochemistry & Cytochemistry. 2009;57(9):825-830. Epub May 11, 2009.

Volpi et al., FISH glossary: an overview of the fluorescence in situ hybridization technique. Biotechniques. Oct. 2008;45(4):385-6, 388, 390, 392, 394, 396, 398, 400, 402, 404, 406, 408-9. doi: 10.2144/000112811.

Wang et al., Imaging-based pooled CRISPR screening reveals regulators of lncRNA localization. Proc Natl Acad Sci U S A. May 28, 2019;116(22):10842-10851. doi: 10.1073/pnas.1903808116. Epub May 13, 2019.

Weibrecht et al., Simultaneous Visualization of Both Signaling Cascade Activity and End-Point Gene Expression in Single Cells. PLoS One. 2011;6(5):e20148. doi: 10.1371/journal.pone.0020148. Epub May 25, 2011.

Wenming, Application of in situ Nucleic Acid Hybridization in Molecular Pathology of Tumor. Pathology Department, Institute of Hepatobiliary Surgery, The Second Military Medical University. Jul. 12, 1992: 182-184.

Xia et al., Spatial transcriptome profiling by MERFISH reveals subcellular RNA compartmentalization and cell cycle-dependent gene expression. Proc Natl Acad Sci U S A. Sep. 24, 2019;116(39):19490-19499. doi: 10.1073/pnas.1912459116. Epub Sep. 9, 2019.

Xiaojun et al., Imaging of Single Molecules by Wide-Field Optical Microscopy. Progress in Chemistry. Mar. 2013; 25(2/3):370-379.

Yujiao et al., Application of Fluorescence In Situ Hybridization In Analysis Of Environmental Microbial Ecology. Techniques and Equipment for Environmental Pollution Control. Nov. 2004;5(11):14-20.

\* cited by examiner ated May 26, 2017, entitled "High-Throughput, Image-Based Screening of Genetic Variant Libraries," by Zhuang, et al., incorporated herein by reference in their entirety.

SYSTEMS AND METHODS FOR HIGH-THROUGHPUT IMAGE-BASED SCREENING

RELATED APPLICATIONS

This application is a national stage filing under 35 U.S.C. § 371 of International Application Serial No. PCT/US2018/034651, filed May 25, 2018, which claims the benefit of U.S. Provisional Patent Application Ser. No. 62/511,920, filed May 26, 2017, entitled "High-Throughput, Image-Based Screening of Genetic Variant Libraries," by Zhuang, et al., incorporated herein by reference in their entirety.

GOVERNMENT FUNDING

This invention was made with government support under MH113094 awarded by National Institutes of Health. The government has certain rights in the invention.

FIELD

The present invention generally relates to imaging cells, for example, to determine phenotypes and/or genotypes in populations of cells.

BACKGROUND

High-throughput screening of genetic perturbations is playing an increasingly important role in advancing biology and biotechnology. For example, by observing the effects of a large number of amino acid changes within a selected protein, large-scale screening allows efficient searches for fluorescent proteins better adapted as bioimaging tools or protein and nucleic acid drugs with desired therapeutic properties. It also allows examining how mutations of a protein or gene regulatory element affect cell function or physiology. Since each cell is composed of many genes, high-throughput screening also allows the effects of inhibition or activation of individual genes or combinations of genes to be tested at the genomic scale, which can help deciphering the effects of genes, gene regulatory networks and cell signaling networks on cellular behaviors.

Screening relies on the ability to select based on the phenotype of interest. Many phenotypes require imaging-based assays to measure. While for a single genetic variant, it is straightforward to introduce genetic variation and measure any image-based phenotype, measuring such phenotypes for many genetic variants is more difficult. It is possible to create and characterize each variant in isolation in many well chambers, but, as the number of variants increases, this approach quickly becomes impractical. Creating all desired variants simultaneously as a pooled library is only moderately more complicated than for a single mutant, but this strategy requires the ability to identify which introduced genetic variation results in which genotype. Although cell sorting methods have been adapted to measure fluorescence intensities for each genetic variant by sorting into multiple intensity bins, high-throughput association of genetic variants to more general image-based phenotypes remains difficult. Accordingly, improvements in such techniques are needed.

SUMMARY

The present invention generally relates to imaging cells, for example, to determine phenotypes and/or genotypes in populations of cells. The subject matter of the present invention involves, in some cases, interrelated products, alternative solutions to a particular problem, and/or a plurality of different uses of one or more systems and/or articles.

In one aspect, the present invention is generally directed to a method. In one set of embodiments, the method comprises introducing, into a plurality of cells, nucleic acids comprising an identification portion and an expression portion; determining phenotype of the cells; and determining genotype of the plurality of cells by sequentially exposing the plurality of cells to nucleic acid probes, and determining binding of target sequences of the nucleic acid probes within the plurality of cells.

The method, in another set of embodiments, includes introducing, into a plurality of cells, a nucleic acid comprising an identification portion and an expression portion; imaging the plurality of cells to determine phenotype of the cells; and determining genotype of the plurality of cells.

According to yet another set of embodiments, the method comprises acquiring an image of a plurality of cells transfected with a plurality of nucleic acids comprising an identification portion and an expression portion, wherein the cells exhibit imagable differences in phenotype due to expression of the expression portion; and acquiring a plurality of images of the plurality of cells, wherein the images of the cells exhibit differences due to differences in the identification portions of the nucleic acids within the cells.

Still another set of embodiments is generally directed to a method comprising acquiring an image of a plurality of cells transfected with a plurality of nucleic acids comprising an identification portion and an expression portion, wherein the cells exhibit imagable differences in phenotype due to expression of the expression portion; and performing in situ hybridization, FISH, multiplexed FISH, smFISH, CAS-FISH, and/or MERFISH on the cells.

In one set of embodiments, the method includes acquiring an image of a plurality of cells transfected with a plurality of nucleic acids comprising an identification portion and an expression portion, wherein the cells exhibit imagable differences in phenotype due to expression of the expression portion; and determining genotype of the plurality of cells.

In another set of embodiments, the method includes introducing, into a plurality of cells, a nucleic acid comprising an identification portion and an expression portion; and determining phenotype of the plurality of cells by sequentially exposing the plurality of cells to nucleic acid probes, and determining binding of the target sequences of the nucleic acid probes within the plurality of cells.

According to yet another set of embodiments, the method includes creating plurality of nucleic acids comprising an identification portion and an expression portion, wherein when expressed in cells, the identification portion is identifiable by sequentially exposing the cells to nucleic acid probes.

Another aspect of the present invention is generally directed to a composition. In accordance with one set of embodiments, the composition comprises a plurality of nucleic acids comprising an identification portion and an expression portion. In some cases, when expressed in cells, the identification portion is identifiable by sequentially exposing the cells to nucleic acid probes.

In another set of embodiments, the composition comprises a plurality of nucleic acids comprising an identification portion and an expression portion. In certain embodiments, the identification portion comprises N variable portions, N being at least 3, each variable portion being of at least two possibilities. In some cases, each possible combination of variable portions is present within the plurality of nucleic acids.

The present invention, in still another embodiment, is generally directed to a protein. In accordance with one set of embodiments, for example, the protein may comprise a sequence (SEQ ID NO: 3)
EHVAFGSEDIENTLAKMDDGQLDGLAFGAIQLDGDGNILQYNAAEGDITG

RDPKQVIGKNLFKDVACGTRSSEFYGKFKEGVASGNLNTMFEWMIPTSRG

PTKVKVHMKKALSGDSYWVFVKRV.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
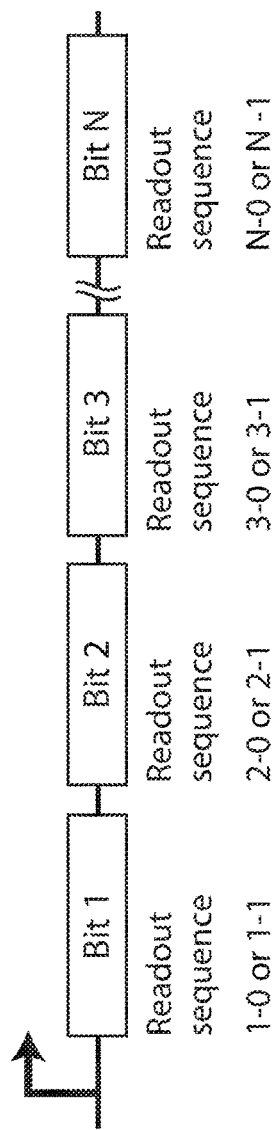
FIGS. 1A-1C illustrate an image-based screening method in accordance with one embodiment of the invention.

The present invention generally relates to imaging cells, for example, to determine phenotypes and/or genotypes in populations of cells. In some aspects, cells may be analyzed, e.g., imaged, to determine their phenotype, and their genotypes may be determined by exposing the cells to nucleic acid probes, e.g., as in smFISH, MERFISH, FISH, in situ hybridization, or other suitable techniques. In some cases, the cells may be exposed to a nucleic acid comprising an identification portion, which may be used to distinguish the cells from each other. In some embodiments, the cells may be exposed to a nucleic acid comprising an expression portion, e.g. a gene, or coding region for a non-translated RNA, etc., that when expressed, produces a protein, RNA, DNA, or the like that may alter the phenotype of the cell or the variable nucleic acid sequence can consist of promoters, gene regulatory elements, transcription factor binding sites, Cas9 guide RNA coding regions, etc. that otherwise alter the phenotype of the cell. In some embodiments, the modifications that contain either the identification portion, the expression portion, or both may be introduced into the genome of a host organism or as exogenous materials, e.g. plasmids. Such changes may involve the addition of synthetic materials, such as synthetic nucleic acids, or modifications, e.g. deletions or mutations, of the genomic material of the host organism. Other aspects are generally directed to compositions or devices for use in such methods, kits for use in such methods, or the like.

Thus, according to one aspect, the present invention is generally directed to systems and methods for determining the phenotypes and/or genotypes of populations of cells using imaging. In some cases, relatively large numbers of cells may be studied, e.g., using suitable imaging techniques such as those described herein, to determine their phenotypes and genotypes. In some embodiments, due to the use of such imaging techniques, relatively large number of cells may be determined, allowing for relatively large-scale or high-throughput screening, as discussed herein. For instance, a plurality of cells may be determined for specific phenotypes (for example, the expression of a suitable protein), and cells with a desirable phenotype may also be determined genotypically.

In some cases, relatively large numbers of cells may be determined. For example, depending on the magnification, a single field of view may contain relatively large numbers of cells (for example, at least 10, at least 100, at least 1,000, at least 10,000, at least 100,000, etc. cells). In addition, a sample may be larger than a single field of view (e.g., especially at relatively high magnifications), and multiple images of different portions of a sample may be acquired, e.g., manually or automatically (for example, using computer control). This may allow even larger numbers of cells to be studied via the use of more than one field of view, for example, at least 10, at least 100, at least 1,000, at least 10,000, at least 100,000, at least 1,000,000, at least 10,000, 000, etc. cells. For instance, an overall image of a sample may be assembled using multiple fields of views (for example, taken simultaneously or near-simultaneously) to produce an image; for example, at least 2, at least 3, at least 5, at least 7, at least 10, at least 15, at least 20, at least 30, at least 50, at least 75, or at least 100 images may be acquired at different fields of views (e.g., corresponding to different portions of a sample) to produce the overall image. Thus, the sample may, in some cases, be substantially larger than a single field of view. For example, a sample may have an area of at least about 0.01 cm$^2$, at least about 0.03 cm$^2$, at least about 0.1 cm$^2$, at least about 0.3 cm$^2$, at least about 1 cm$^2$, at least about 3 cm$^2$, or at least about 10 cm$^2$, etc.

In some embodiments, multiple images may be taken for the same field of view. For example, at least 2, at least 3, at least 5, at least 7, at least 10, at least 15, at least 20, at least 30, at least 50, at least 75, or at least 100 images may be acquired for the same field of view.

In some cases, multiple images may be taken at each of the fields of view imaged within a sample, in one set of embodiments. In some embodiments, different wavelengths may be used. For example, in some cases, images may be collected, for example, with different illumination sources, and captured using different optical filters so as to produce different colors of images that probe the presence of different fluorescent compounds. Thus, in some embodiments, multiple images may be taken at different wavelengths, e.g., to view the images in different colors (for example, red-green-blue, red-yellow-blue, cyan-magenta-yellow, or the like).

In some embodiments, these images may be collected at defined time intervals so as to create time-lapse images of the sample. This may be useful, for example, to determine properties that change with time, e.g., the growth of cells. For example, an image (or a plurality of images) may be acquired at different points in time, e.g., with a periodicity of about 5 seconds, about 10 seconds, about 15 seconds, about 30 seconds, about 1 minute, about 2 minutes, about 3 minutes, about 5 minutes, about 10 minutes, about 15 minutes, about 20 minutes, about 30 minutes, about 1 hour, about 2 hours, about 3 hours, about 4 hours, about 1 day, or the like.

Similarly, in some embodiments, images may be collected after different treatments of the same sample.

In addition, in some embodiments, multiple images may be collected with different imaging modalities, e.g. super-resolution optical microscopy, conventional epi-fluorescence microscopy, confocal microscopy, etc., including those described herein. Such images may be combined, in some cases, to create high content optical measurements of the properties of the cells.

The cells may be any suitable cells, for example, bacterial cells (e.g., *E. coli*), mammalian cells (e.g., human or non-human cells), eukaryotic cells, prokaryotic cells, yeast cells, or other types of cells. The cells may arise from any suitable source, for example, a cell culture. In some cases, the cells may be taken from a tissue sample, e.g., from a biopsy, artificially grown or cultured, etc. In some cases, the cells are genetically engineered. In some cases, a tissue sample may be analyzed. In certain embodiments, a plurality of cells may be transfected as discussed herein, and the resulting phenotypes of the cells determined.

It should also be understood that certain embodiments of the invention may be directed to systems that do not necessarily include cells. For example, in some cases, one or more of the cells may be artificial cells, for example, wells that contain biological components that can express the desired phenotype. For example, in certain embodiments, the cells may comprise microfluidic wells or microfluidic droplets that contain enzymatic components required to perform in vitro translation.

In one set of embodiments, the cells may be transfected with a nucleic acid comprising an identification portion or "barcode" of nucleotides, which may be used to distinguish a nucleic acid in one cell from those in other cells. A library of identification portions may be used in certain embodiments, e.g., containing at least 10, at least $10^2$, at least $10^3$, at least $10^4$, at least $10^5$, at least $10^6$, at least $10^7$, at least $10^8$, etc. unique sequences. The unique sequences may be all individually determined (e.g., randomly), although in some cases, the identification portion may be defined as a plurality of variable portions (or "bits"), e.g., in sequence. For example, an identification portion may include at least 2, at least 3, at least 5, at least 7, at least 10, at least 15, at least 20, at least 25, at least 30, at least 40, or at least 50 variable portions. Each of the variable portions may include at least 2, at least 3, at least 4, at least 5, at least 7, at least 10, at least 15, at least 20, at least 25, at least 30, at least 40, at least 50, or more possibilities.

Thus, for example, an identification portion defined with 22 variable regions and 2 unique possibilities per variable region would define a library of identification portions with $2^{22}$=4,194,304 members. As another non-limiting example, an identification portion may be defined with 10 variable regions and 7 unique possibilities per variable region to define a library of identification portions with $7^{10}$ members. It should be understood that a variable portion may include any suitable number of nucleotides, and different variable portions within an identification portion may independently have the same or different numbers of nucleotides. Different variable regions also may have the same or different numbers of unique possibilities.

For example, a variable portion may be defined having a length of at least 2, at least 3, at least 4, at least 5, at least 7, at least 10, at least 15, at least 20, at least 25, at least 30, at least 40, at least 50, or more nucleotides, and/or a maximum length of no more than 50, no more than 40, no more than 30, no more than 25, no more than 20, no more than 15, no more than 10, no more than 7, no more than 5, no more than 4, no more than 3, or no more than 2 nucleotides. Combinations of these are also possible, e.g., a variable portion may have a length of between 5 and 50 nt, or between 15 and 25 nt, etc. A non-limiting example of a library is illustrated with Readout sequences 1-1, 1-0, 2-1, 2-0, etc. through 22-1 and 22-0, which may be concatenated together (e.g., Readout sequence 1-Readout sequence 2-Readout sequence 3- . . . -Readout 22) to produce an identification sequence (in this non-limiting example, each sequence position 1, 2, . . . 22 may have one of two possibilities, identified with –0 and –1, e.g., sequence position 1 can be either Readout sequence 1-1 or 1-0, sequence position 2 can be either Readout sequence 2-1 or 2-0, etc.). Similarly, according to certain embodiments, information could also be included in the absence of such sequences. For example, the same information included in the presence of one sequence (e.g. sequence 1-0), could also be determined from the absence of another sequence (e.g., sequence 1-1)

Each readout sequence position may be thought of as a "bit" (e.g., 1 or 0 in this example), although it should be understood that the number of possibilities for each "bit" is not necessarily limited to only 2, unlike in a computer. In other embodiments, as previously discussed, there may be 3 possibilities (i.e., a "trit"), 4 possibilities (i.e., a "quad-bit"), 5 possibilities, etc., instead of only 2 possibilities as in some embodiments. However, the use of bits (of any number of possibilities) to form an identification portion can allow, in some but not all embodiments, the use of codewords, error-detecting codes, error-correcting codes, or the like within the identification portion, for example, as discussed in detail herein.

In some cases, the variable portions of the identification portion may be concatenated together to produce the identification portion. In other cases, however, one or more variable portions may be separated, for example, with constant portions of nucleotides, to produce the identification portion. In addition, in some cases, all of the possible variable portions within a library may be unique, e.g., to minimize confusion. Any method may be used for the concatenation. For example, the portions may be concatenated together using ligation, overlap PCR, oligonucleotide pool synthesis, or other techniques known to those of ordinary skill in the art for joining or concatenating nucleic acids together.

In certain embodiments, all members of a library are produced and/or are used. In other embodiments, however, not all members of a library are necessarily produced and/or used. For example, in some embodiments, e.g., to reduce or eliminate ambiguity or inadvertent reuse, a smaller subset of the library may be used, e.g., less than 75%, less than 50%, less than 40%, less than 30%, less than 20%, or less than 10% of all possible members of a library are produced and/or are used.

In addition, in one set of embodiments, the cells may be transfected with a nucleic acid comprising an expression portion. The expression portion may be any suitable nucleic acid sequence that is suspected of being able to alter the phenotype of a cell. For example, the expression portion may encode a gene, a protein, a regulatory sequence (for example, an operon, a promoter, a repressor, a transcription factor binding site, etc.), a sequence encoding non-coding RNA (for example, miRNA, siRNA, rRNA, tRNA, lncRNA, snoRNA, snRNAs, exRNAs, piRNA, tsRNA, rsRNA, shRNA, Cas9 guide RNA, etc.), or the like. In some cases, the expression portion may be part of the same nucleic acid comprising an identification portion; in other cases, however, the expression portion may be part of a different nucleic acid.

In certain embodiments, there may be more than one possibility for the expression portion. For example, a library of nucleic acids may be prepared where there are at least two possibilities for the expression portion. In certain cases, there may be at least 10, at least $10^2$, at least $10^3$, at least $10^4$, at least $10^5$, etc. possibilities for an expression portion. In addition, in some cases, more than one expression portion may be present (for example, encoding two genes, a gene and a noncoding nucleic acid sequence such as an siRNA sequence, or the like).

As an example, a plurality of distinguishable nucleic acids may be prepared using one or more identification portions (such as those described above) and one or more expression portions. It should be understood, however, that the number of possible identification portions need not equal the number of possible expression portions, i.e., there may be some redundancy involved.

In certain embodiments, the expression portion and the identification portions are combined randomly within the nucleic acids, e.g., to form a nucleic acid library. In other embodiments, the expression portion and the identification portion are combined deterministically within the nucleic acids, e.g., to form a nucleic acid library.

In some cases, the association between identification portion and expression portion can be determined by sequencing the nucleic acids. Any technique may be used for sequencing, for example, Sanger sequencing, high-throughput sequencing, next generation sequencing, nanopore sequencing, sequencing by ligation, sequencing by synthesis, etc. Those of ordinary skill in the art will be aware of different techniques for sequencing nucleic acids.

To facilitate sequencing, in some embodiments, each unique associated expression portion and identification portion may additionally be associated with another nucleotide sequence, for example, of at least 5, at least 10, at least 15, between 5 and 50, between 10 and 100, between 5 and 30 nucleotides, or the like. For example, the unique nucleotide sequence may be used to match reads in, for example, high-throughput sequencing. In some cases, the identification portion and the expression portion may contain a selective factor that allows selection for properly combined identification portions and expression portions. As a non-limiting example, the identification portion could be associated with, for example, an antibiotic resistance gene and the expression portion could, for example, be associated with a plasmid replication origin. Thus, for example, transfected cells can be selected or sorted in certain embodiments, for example, by antibiotic selection using the resistance gene.

In certain embodiments, for example, an expression portion may comprise a gene. In some cases, more than one possibility for the gene may be present in a library. For instance, one possibility may represent a wild-type form while another possibility may represent a diseased form, a genetic variant, a mutant form, or the like of a protein. In some cases, there may be a gene and all (or a subset of all) possible single amino acid substitutions and/or all possible single amino acid insertions of the gene and/or all possible single amino acid deletions of the gene present within the library. In addition, this may be extended even further. For example, there may also be all possible (or a subset of all) two amino acid substitutions of the gene and/or all possible two amino acid insertions of the gene and/or all possible two amino acid deletions of the gene (and these two amino acid substitutions and/or insertions and/or deletions may be consecutive or nonconsecutive). This can be extended to three, four, five, etc. amino acids as well in certain instances.

In other embodiments, the expression portion may represent a property of an external environment to which the cell is exposed. As non-limiting examples, the expression portion may correspond to viral vectors printed onto discrete regions of a cell culture substrate, with the spatial location of the cells determining which of the expression portions to which they are exposed. Similarly, in another example, the expression portion could represent small molecules added individually to the cells (for example, if the cells are in wells).

It should be understood that although the number of expression portions and/or identification portions may be relatively large number of possibilities (for example, millions), this is readily achievable by one of ordinary skill in the art using technologies such as computers and automated nucleic acid synthesis machines (many of which are commercially available), as well as techniques such as solid-phase synthesis and/or isothermal assembly (see, e.g., Example 4) and/or error-prone PCR and/or ligating or otherwise assembling by for example overlap PCR multiple variable regions combinatorially. Similarly, a correspondingly relatively large number of unique identification portions may be correlated with such large numbers of possibilities for the expression portions, for example, through the use of relatively small numbers of suitable variable regions and unique "bits" that can be produced for each. Accordingly, a library of nucleic acids (e.g., each containing an identification portion and an expression portion) may be prepared, e.g., containing at least 10, at least $10^2$, at least $10^3$, at least $10^4$, at least $10^5$, at least $10^6$, at least $10^7$, at least $10^8$, etc. unique members.

In one set of embodiments, nucleic acids from the library of nucleic acids may be transfected or otherwise introduced into a cell. Any suitable technique may be used to introduce the nucleic acid. In one set of embodiments, the nucleic acids may be incorporated into plasmids that may be taken up by the cells. Other methods of transfection of nucleic acids into cells include, but are not limited to, calcium phosphate (e.g., tricalcium phosphate), electroporation, cell squeezing, mixing a cationic lipid with the material to produce liposomes which fuse with the cell membrane, or the like. Additional non-limiting examples of suitable methods include dendrimers, cationic polymers, lipofection, FuGENE, sonoporation, optical transfection, protoplast fusion, impalefection, the gene gun, magnetofection, particle bombardment, viral infection, or the like.

In certain embodiments, the nucleic acids may be introduced to the cells such that at least 50% of the cells have only 0 or 1 nucleic acids introduced therein, e.g., transfected. In some cases, at least 60%, at least 70%, at least 80%, at least 85%, at least 90%, or at least 95% of the cells may have only 0 or 1 nucleic acids introduced therein. This may be achieved, for example, using suitable dilution techniques, suitable cell sorting techniques, or through the use of other techniques such as microfluidic droplets. In other cases, the percent of transfected cells may be smaller, such as less than 50%, less than 20%, less than 10%, less than 1%. In some embodiments, the non-transfected cells may be removed. Non-limiting examples of cell removal include treatment with a chemical (such as an antibiotic) that, for example, kills or prevents from dividing the non-transfected cells. In another example, some or all of the non-transfected cells may be sorted from the transfected cells using, for example fluorescence activated cell sorting and/or other suitable cell sorting or microfluidic techniques.

In certain embodiments, the identification portion and the expression portion may be combined onto a single source, e.g. a single plasmid. In other embodiments, these portions may be provided to the cell in separate sources, e.g. two different plasmids, or two different viral delivery vehicles. Other examples of introducing a nucleic acid into a cell are disclosed herein, and the methods of introduction may be the same or different. In some embodiments, the expression portion could represent an external stimulus provided to the sample, such as those provided via small molecules.

The combination of the identification portion and the expression portion, whether it is on the same or different vehicles, e.g., plasmids, can be determined, for example, randomly or deterministically. For example, a given protein mutant can be assigned to a given barcode, and the plasmids expressed each of these items co-transfected into a single cell culture. As another example, a library of protein mutants and a library of given barcodes can be combined with each cell obtaining a random combination of the two. In some embodiments, the specific association between the identification and the expression portions can be measured with any of a variety of techniques. For example, PCR may be used to amplify a portion of a plasmid containing both the identification and the expression portions, and then sequencing approaches, included next-generation sequencing methods, can be used to identify which identification region occurs with which expression portion via direct sequencing of this PCR product. Those of ordinary skill in the art will be aware of other techniques that can be used to sequence the nucleic acids, e.g., containing the identification portion and the expression portion.

The cells may be analyzed to determine their phenotype, in another aspect. The phenotype may be determined using any suitable technique, for example, using optical techniques, through analysis of cell behavior, or the like. Specific examples include, but are not limited to, microscopy or other optical techniques such as light microscopy, fluorescence microscopy, confocal microscopy, near-field microscopy, two-photon microscopy, or phase contrast microscopy, or other techniques described herein. In some cases, super-resolution techniques may be used, including any of those described herein. In some cases, the phenotype can be probed by other techniques, such as atomic force microscopy or patch clamping. In some cases, both microscopy and another technique can be used in combination for determining the phenotype.

Examples of phenotype that may be determined include, but are not limited to, the morphology of a cell (e.g., shape, size, visual appearance, organelles, etc.), certain characteristics of cell motility (for example, speed, persistence, chemotaxis behavior, etc.), certain characteristics of intercellular interactions (e.g. cell to cell adhesion, cell to cell avoidance etc.), or certain subcellular characteristics (for example position of a protein or nucleic acid, diffusion of protein or nucleic acids, binding of two or more proteins and/or nucleic acids, etc.). In certain embodiments, the cells are present on a substrate, for example, suitable for culturing and/or imaging cells. For example, the substrate may be glass, silicon, plastic (for example, polystyrene, polypropylene, polycarbonate, etc.), or the like. In some cases, at least a portion of the substrate may be at least partially optically transparent. The substrate may also be untreated or treated in some fashion to facilitate cell attachment.

In some embodiments, phenotypes that may be determined include all, or at least a portion, of the transcriptome of the cells. A variety of techniques may be used to determine transcriptomes including, but not limited to, smFISH, MERFISH, or other techniques such as those described herein. See also U.S. patent application Ser. No. 15/329,683 or Int. Pat. Apl. Pub. No. WO 2016/018960, each incorporated herein by reference in its entirety. In some cases, the transcriptome may be determined spatially within one or more cells.

In addition, in some cases, phenotypes that may be determined include all, or at least a portion, of the chromosome of the cells, and/or agents such as proteins or RNA that may be bound to or otherwise associated with the chromosome of the cells. For example, concentrations, spatial positions, activities, associations, etc. of the chromosomes and/or other associated agents may be determined, according to certain embodiments of the invention. In some cases, the chromosomes may be determined spatially within one or more cells. Non-limiting examples of techniques that may be used to determine chromosomes include multiplexed DNA FISH or CASFISH.

In addition, in some cases, phenotypes that may be determined include all, or at least a portion, of the proteome of the cells. A variety of techniques may be used to determine proteomes include antibody labeling, sequential antibody labeling, multiplexed antibody imaging, or other multiplexed protein imaging techniques. For example, concentrations, spatial positions, activities, associations, etc. of the proteins and/or other associated agents may be determined.

In certain embodiments, one or more markers may be determined within the cell to determine a phenotype. For example, the marker may be indicative for a certain cell protein, nucleic acid, morphological characteristic, or the like, or the marker may be indicative of cell behavior. In addition, the marker may be one that can be visually determined in some cases. For example, the marker may be fluorescent, or may alter fluorescence of another fluorescent entity within the cell (for example, via enhancement or quenching). The marker may also be a dye or may change color in some embodiments. Accordingly, differences in intensity, wavelength, frequency, position, distribution, or the like between cells in an image may be determined to determine phenotypes of the cells. Other methods of determining a marker may also be used in some cases; for example, the marker may be radioactive. Many such markers may be obtained commercially.

Moreover, it should be understood that these measurements are not mutually exclusive. Any combination of these measurements can be performed in a single sample. Moreover, such measurements may be repeated in some embodiments, e.g., for the same sample. For instance, the measurements may be repeated to ensure validity or reduce potential errors (e.g., measurement errors), or the measurements may be repeated after exposure to various stimuli or conditions, such as treatment with different nutritional sources, small molecules, or other suitable agents that may interact with the cells.

In some cases, the phenotype of a cell may be altered by application of an expression portion, e.g., as discussed above, that may be expressed in some form by the cell to alter its phenotype. For example, an expression portion that encodes a protein to the cell may be added, and the cell may express the protein. If different proteins are encoded in different cells, then the cells may exhibit different phenotypes, which can be determined as noted above. Thus, for instance, a plurality of cells may be transfected or otherwise introduced to a plurality of different expression portions, and then the cells studied to determine the effects the different expression portions have had on their phenotype.

The expression portion, in some embodiments, may produce the marker (for example, if the marker is a fluorescent protein), or the expression portion may produce a product (for example, a protein or a nucleic acid sequence) that can interact with a marker in some fashion, directly or indirectly, which results in a determinable change in phenotype (for example, that can be identified using a suitable fluorescent compound), or in other cases, the expression portion may otherwise change the abundance of the marker, directly or indirectly (for example, if the expression portion is a promoter, gene regulatory element, shRNA, guide RNA, etc.).

In certain embodiments, the phenotype may be produced from a specific combination of multiple sequences. For example, the phenotype might represent the overexpression of individual pairs of proteins. As another non-limiting example, the phenotype could be generated by a mutation to the host genome as well as overexpression of a separate protein. It should be understood that the expression portion represents the unique combination of the elements necessary to express the full phenotype and the number of elements need not be limited to two, as described here.

In some aspects, cells may be immobilized or fixed to a substrate, e.g., prior to determining genotype as discussed below. In some cases, immobilization or fixing of the cells may occur after determination of phenotype. This may be useful according to certain embodiments, for example, to correlate the phenotype of the cells within an image with the subsequent genotype of the cells (e.g., determined as discussed below). The cells can also be fixed in some embodiments before measuring the phenotype instead of after measuring the phenotype and before measuring the genotype.

Those of ordinary skill in the art will be aware of systems and methods for fixing or otherwise immobilizing cells on a substrate. As non-limiting examples, a cell may be fixed using chemicals such as formaldehyde, paraformaldehyde, glutaraldehyde, ethanol, methanol, acetone, acetic acid, or the like. In one embodiment, a cell may be fixed using Hepes-glutamic acid buffer-mediated organic solvent (HOPE). See also U.S. Pat. Apl. Ser. No. 62/419,033, incorporated herein by reference in its entirety.

In one aspect, the genotype of the cells are determined. This can be performed, for example, after determining their phenotype as discussed above. A variety of different techniques for determining the genotype of cells may be used, for example, FISH, smFISH, MERFISH, in situ hybridization, multiplexed FISH, CASFISH, or other techniques known to those of ordinary skill in the art. These approaches can involve, in some embodiments, the direct hybridization to the identification portion, or molecules generated via the host cell from that portion. It can also involve, in certain instances, binding of separate adaptor entities, which in turn bind directly to the identification portion or molecules generated from it. Additional non-limiting examples of techniques include those disclosed in U.S. patent application Ser. No. 15/329,683 or Int. Pat. Apl. Pub. No. WO 2016/018960, each incorporated herein by reference in its entirety.

In one set of embodiments, the determination of the genotype of the cells may be facilitated by determining an identification portion of a nucleic acid within the cells. For example, nucleic acids comprising an identification portion and an expression portion may have been introduced into the cells; the expression portion may have led to different phenotypes as discussed above. However, it would also be important to know which nucleic acids were introduced into which cells, thereby allowing an understanding between the observed phenotypes and the genotypes leading to those phenotypes. By determining the identification portion within the cells, as discussed herein, the identity of the nucleic acid contained within each cell may be determined, and thus a specific expression portion may also be determined, e.g., if the nucleic acid comprises the identification portion and the expression portion on the same individual nucleic acid.

As a non-limiting example, in one set of embodiments, the cells may be sequentially exposed to nucleic acid probes able to bind to different portions of the identification portion, or molecules, such as RNA, expressed by the cell from this identification portion, for example, nucleic acid probes comprising a target sequence (e.g., that is able to bind to at least a portion of the identification portion, in some cases specifically) and a read sequence (e.g., which may be "read" in some fashion to determine binding), and binding of the nucleic acid probes within the cells may be determined. For example, the cells may be exposed to secondary nucleic acid probe may contain a recognition sequence able to bind to or hybridize with a read sequence, and which may contain a signaling entity. By determining signaling entities within images (and in some cases, inactivating the signaling entities between images and exposure to different nucleic acid probes), the identification portions of the cells may be determined.

As discussed herein, a variety of nucleic acid probes may be used to determine one or more nucleic acids within a cell. The probes may comprise nucleic acids (or entities that can hybridize to a nucleic acid, e.g., specifically) such as DNA, RNA, LNA (locked nucleic acids), PNA (peptide nucleic acids), or combinations thereof. In some cases, additional components may also be present within the nucleic acid probes, e.g., as discussed below. In some embodiments, the nucleic acid probes can be created from other components, e.g. protein or other small molecules, or may represent a combination of these components with nucleic acids such as DNA, RNA, LNA, PNA, or the like.

The nucleic acid probes may be introduced into the cells using any suitable method. In some cases, the cells may be sufficiently permeabilized such that the nucleic acid probes may be introduced into the cells by flowing a fluid containing the nucleic acid probes around the cells. In some cases, the cells may be sufficiently permeabilized as part of a fixation process; in other embodiments, cells may be permeabilized by exposure to certain chemicals such as ethanol, methanol, Triton, or the like. In addition, in some embodiments, techniques such as electroporation or microinjection may be used to introduce nucleic acid probes into the cells.

The determination of nucleic acids within the cells may be qualitative and/or quantitative. In addition, the determination may also be spatial, e.g., the position of the nucleic acid within the cells may be determined in two or three dimensions. In some embodiments, the positions, number, and/or concentrations of nucleic acids within the cells may be determined.

Thus, certain aspects of the present invention are generally directed to nucleic acid probes that are introduced into a cell. The probes may comprise any of a variety of entities that can hybridize to a nucleic acid, typically by Watson-Crick base pairing, such as DNA, RNA, LNA, PNA, etc., depending on the application. The nucleic acid probe typically contains a target sequence that is able to bind to at least a portion of a target nucleic acid, in some cases specifically. When introduced into a cell or other system, the target system may be able to bind to a specific target nucleic acid (e.g., an mRNA, or other nucleic acids as discussed herein). In some cases, the nucleic acid probes may be determined using signaling entities (e.g., as discussed below), and/or by using secondary nucleic acid probes able to bind to the nucleic acid probes (i.e., to primary nucleic acid probes). The determination of such nucleic acid probes is discussed in detail below.

In some cases, more than one type of (primary) nucleic acid probe may be applied to the cells, e.g., simultaneously. For example, there may be at least 2, at least 5, at least 10, at least 25, at least 50, at least 75, at least 100, at least 300, at least 1,000, at least 3,000, at least 10,000, or at least 30,000 distinguishable nucleic acid probes that are applied to the cells, e.g., simultaneously or sequentially.

The target sequence may be positioned anywhere within the nucleic acid probe (or primary nucleic acid probe or encoding nucleic acid probe). The target sequence may contain a region that is substantially complementary to a portion of a target nucleic acid. In some cases, the portions may be at least 50%, at least 60%, at least 70%, at least 75%, at least 80%, at least 85%, at least 90%, at least 92%, at least 94%, at least 95%, at least 96%, at least 97%, at least 98%, at least 99%, or 100% complementary. In some cases, the target sequence may be at least 5, at least 10, at least 15, at least 20, at least 25, at least 30, at least 35, at least 40, at least 50, at least 60, at least 65, at least 75, at least 100, at least 125, at least 150, at least 175, at least 200, at least 250, at least 300, at least 350, at least 400, or at least 450 nucleotides in length. In some cases, the target sequence may be no more than 500, no more than 450, no more than 400, no more than 350, no more than 300, no more than 250, no more than 200, no more than 175, no more than 150, no more than 125, no more than 100, be no more than 75, no more than 60, no more than 65, no more than 60, no more than 55, no more than 50, no more than 45, no more than 40, no more than 35, no more than 30, no more than 20, or no more than 10 nucleotides in length. Combinations of any of these are also possible, e.g., the target sequence may have a length of between 10 and 30 nucleotides, between 20 and 40 nucleotides, between 5 and 50 nucleotides, between 10 and 200 nucleotides, or between 25 and 35 nucleotides, between 10 and 300 nucleotides, etc. Typically, complementarity is determined on the basis of Watson-Crick nucleotide base pairing.

The target sequence of a (primary) nucleic acid probe may be determined with reference to a target nucleic acid suspected of being present within a cell. For example, a target nucleic acid to a protein may be determined using the protein's sequence, by determining the nucleic acids that are expressed to form the protein. In some cases, only a portion of the nucleic acids encoding the protein are used, e.g., having the lengths as discussed above. In addition, in some cases, more than one target sequence that can be used to identify a particular target may be used. For instance, multiple probes can be used, sequentially and/or simultaneously, that can bind to or hybridize to different regions of the same target. Hybridization typically refers to an annealing process by which complementary single-stranded nucleic acids associate through Watson-Crick nucleotide base pairing (e.g., hydrogen bonding, guanine-cytosine and adenine-thymine) to form double-stranded nucleic acid.

In some embodiments, a nucleic acid probe, such as a primary nucleic acid probe, may also comprise one or more "read" sequences. However, it should be understood that read sequences are not necessary in all cases. In some embodiments, the nucleic acid probe may comprise 1, 2, 3, 4, 5, 6, 7, 8, 9, 10, 11, 12, 13, 14, 15, 16 or more, 20 or more, 32 or more, 40 or more, 50 or more, 64 or more, 75 or more, 100 or more, 128 or more read sequences. The read sequences may be positioned anywhere within the nucleic acid probe. If more than one read sequence is present, the read sequences may be positioned next to each other, and/or interspersed with other sequences. In some embodiments, the read sequence is contained within the identification portion and/or in RNA expressed from the identification portion.

The read sequences, if present, may be of any length. If more than one read sequence is used, the read sequences may independently have the same or different lengths. For instance, the read sequence may be at least 5, at least 10, at least 15, at least 20, at least 25, at least 30, at least 35, at least 40, at least 50, at least 60, at least 65, at least 75, at least 100, at least 125, at least 150, at least 175, at least 200, at least 250, at least 300, at least 350, at least 400, or at least 450 nucleotides in length. In some cases, the read sequence may be no more than 500, no more than 450, no more than 400, no more than 350, no more than 300, no more than 250, no more than 200, no more than 175, no more than 150, no more than 125, no more than 100, be no more than 75, no more than 60, no more than 65, no more than 60, no more than 55, no more than 50, no more than 45, no more than 40, no more than 35, no more than 30, no more than 20, or no more than 10 nucleotides in length. Combinations of any of these are also possible, e.g., the read sequence may have a length of between 10 and 30 nucleotides, between 20 and 40 nucleotides, between 5 and 50 nucleotides, between 10 and 200 nucleotides, or between 25 and 35 nucleotides, between 10 and 300 nucleotides, etc.

The read sequence may be arbitrary or random in some embodiments. In certain cases, the read sequences are chosen so as to reduce or minimize homology with other components of the cell, e.g., such that the read sequences do not themselves bind to or hybridize with other nucleic acids suspected of being within the cell. In some cases, the homology may be less than 10%, less than 8%, less than 7%, less than 6%, less than 5%, less than 4%, less than 3%, less than 2%, or less than 1%. In some cases, there may be a homology of less than 20 basepairs, less than 18 basepairs, less than 15 basepairs, less than 14 basepairs, less than 13 basepairs, less than 12 basepairs, less than 11 basepairs, or less than 10 basepairs. In some cases, the basepairs are sequential.

In one set of embodiments, a population of nucleic acid probes may contain a certain number of read sequences, which may be less than the number of targets of the nucleic acid probes in some cases. Those of ordinary skill in the art will be aware that if there is one signaling entity and n read sequences, then in general $2^n-1$ different nucleic acid targets may be uniquely identified. However, not all possible combinations need be used. For instance, a population of nucleic acid probes may target 12 different nucleic acid sequences, yet contain no more than 8 read sequences. As another example, a population of nucleic acids may target 140 different nucleic acid species, yet contain no more than 16 read sequences. Different nucleic acid sequence targets may be separately identified by using different combinations of read sequences within each probe. For instance, each probe may contain 1, 2, 3, 4, 5, 6, 7, 8, 9, 10, 11, 12, 13, 14, 15, etc. or more read sequences. In some cases, a population of nucleic acid probes may each contain the same number of read sequences, although in other cases, there may be different numbers of read sequences present on the various probes.

As a non-limiting example, a first nucleic acid probe may contain a first target sequence, a first read sequence, and a second read sequence, while a second, different nucleic acid probe may contain a second target sequence, the same first read sequence, but a third read sequence instead of the second read sequence. Such probes may thereby be distinguished by determining the various read sequences present or associated with a given probe or location, as discussed herein.

In addition, in some embodiments, the nucleic acid probes (and/or their corresponding, complimentary sites on, for example, the encoding probes or RNA that may be transcribed from the identification portion, or on the identification portion itself), in certain embodiments, may be made using only 2 or only 3 of the 4 bases, such as leaving out all the "G"s or leaving out all of the "C" s within the probe. Sequences lacking either "G"s or "C" s may form very little secondary structure in certain embodiments, and can contribute to more uniform, faster hybridization.

In some embodiments, the nucleic acid probe may contain a signaling entity. It should be understood that signaling entities are not required in all cases, however; for instance, the nucleic acid probe may be determined using secondary nucleic acid probes in some embodiments, as is discussed in additional detail below. Examples of signaling entities that can be used are also discussed in more detail below.

Other components may also be present within a nucleic acid probe as well. For example, in one set of embodiments, one or more primer sequences may be present, e.g., to allow for enzymatic amplification of probes. Those of ordinary skill in the art will be aware of primer sequences suitable for applications such as amplification (e.g., using PCR or other suitable techniques). Many such primer sequences are available commercially. Other examples of sequences that may be present within a primary nucleic acid probe include, but are not limited to promoter sequences, operons, identification sequences, nonsense sequences, or the like.

Typically, a primer is a single-stranded or partially double-stranded nucleic acid (e.g., DNA) that serves as a starting point for nucleic acid synthesis, allowing polymerase enzymes such as nucleic acid polymerase to extend the primer and replicate the complementary strand. A primer is (e.g., is designed to be) complementary to and to hybridize to a target nucleic acid. In some embodiments, a primer is a synthetic primer. In some embodiments, a primer is a non-naturally-occurring primer. A primer typically has a length of 10 to 50 nucleotides. For example, a primer may have a length of 10 to 40, 10 to 30, 10 to 20, 25 to 50, 15 to 40, 15 to 30, 20 to 50, 20 to 40, or 20 to 30 nucleotides. In some embodiments, a primer has a length of 18 to 24 nucleotides.

In addition, the components of the nucleic acid probe may be arranged in any suitable order. For instance, in one embodiment, the components may be arranged in a nucleic acid probe as: primer-read sequences-targeting sequence-read sequences-reverse primer. The "read sequences" in this structure may each contain any number (including 0) of read sequences, so long as at least one read sequence is present in the probe. Non-limiting example structures include primer-targeting sequence-read sequences-reverse primer, primer-read sequences-targeting sequence-reverse primer, targeting sequence-primer-targeting sequence-read sequences-reverse primer, targeting sequence-primer-read sequences-targeting sequence-reverse primer, primer-target sequence-read sequences-targeting sequence-reverse primer, targeting sequence-primer-read sequence-reverse primer, targeting sequence-read sequence-primer, read sequence targeting sequence-primer, read sequence-primer-targeting sequence-reverse primer, etc. In addition, the reverse primer is optional in some embodiments, including in all of the above-described examples.

After introduction of the nucleic acid probes into a cell, the nucleic acid probes may be directly determined by determining signaling entities (if present), and/or the nucleic acid probes may be determined by using one or more secondary nucleic acid probes, in accordance with certain aspects of the invention. As mentioned, in some cases, the determination may be spatial, e.g., in two or three dimensions. In addition, in some cases, the determination may be quantitative, e.g., the amount or concentration of a primary nucleic acid probe (and of a target nucleic acid) may be determined. Additionally, the secondary probes may comprise any of a variety of entities able to hybridize a nucleic acid, e.g., DNA, RNA, LNA, and/or PNA, etc., depending on the application. Signaling entities are discussed in more detail below.

A secondary nucleic acid probe may contain a recognition sequence able to bind to or hybridize with a read sequence of a primary nucleic acid probe. In some cases, the binding is specific, or the binding may be such that a recognition sequence preferentially binds to or hybridizes with only one of the read sequences that are present. The secondary nucleic acid probe may also contain one or more signaling entities. If more than one secondary nucleic acid probe is used, the signaling entities may be the same or different.

The recognition sequences may be of any length, and multiple recognition sequences may be of the same or different lengths. If more than one recognition sequence is used, the recognition sequences may independently have the same or different lengths. For instance, the recognition sequence may be at least 5, at least 10, at least 15, at least 20, at least 25, at least 30, at least 35, at least 40, or at least 50 nucleotides in length. In some cases, the recognition sequence may be no more than 75, no more than 60, no more than 65, no more than 60, no more than 55, no more than 50, no more than 45, no more than 40, no more than 35, no more than 30, no more than 20, or no more than 10 nucleotides in length. Combinations of any of these are also possible, e.g., the recognition sequence may have a length of between 10 and 30, between 20 and 40, or between 25 and 35 nucleotides, etc. In one embodiment, the recognition sequence is of the same length as the read sequence. In addition, in some cases, the recognition sequence may be at least 50%, at least 60%, at least 70%, at least 75%, at least 80%, at least 85%, at least 90%, at least 92%, at least 94%, at least 95%, at least 96%, at least 97%, at least 98%, at least 99%, or at least 100% complementary to a read sequence of the primary nucleic acid probe.

As mentioned, in some cases, the secondary nucleic acid probe may comprise one or more signaling entities. Examples of signaling entities are discussed in more detail below.

As discussed, in certain aspects of the invention, nucleic acid probes are used that contain various "read sequences." For example, a population of primary nucleic acid probes may contain certain "read sequences" which can bind certain of the secondary nucleic acid probes, and the locations of the primary nucleic acid probes are determined within the cells using secondary nucleic acid probes, e.g., which comprise a signaling entity. As mentioned, in some cases, a population of read sequences may be combined in various combinations to produce different nucleic acid probes, e.g., such that a relatively small number of read sequences may be used to produce a relatively large number of different nucleic acid probes.

Thus, in some cases, a population of primary nucleic acid probes (or other nucleic acid probes) may each contain a certain number of read sequences, some of which are shared between different primary nucleic acid probes such that the total population of primary nucleic acid probes may contain a certain number of read sequences. A population of nucleic acid probes may have any suitable number of read sequences. For example, a population of primary nucleic acid probes may have 1, 2, 3, 4, 5, 6, 7, 8, 9, 10, 11, 12, 13, 14, 15, 16, 17, 18, 19, 20 etc. read sequences. More than 20 are also possible in some embodiments. In addition, in some cases, a population of nucleic acid probes may, in total, have 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 20 or more, 24 or more, 32 or more, 40 or more, 50 or more, 60 or more, 64 or more, 100 or more, 128 or more, etc. of possible read sequences present, although some or all of the probes may each contain more than one read sequence, as discussed herein. In addition, in some embodiments, the population of nucleic acid probes may have no more than 100, no more than 80, no more than 64, no more than 60, no more than 50, no more than 40, no more than 32, no more than 24, no more than 20, no more than 16, no more than 15, no more than 14, no more than 13, no more than 12, no more than 11, no more than 10, no more than 9, no more than 8, no more than 7, no more than 6, no more than 5, no more than 4, no more than 3, or no more than two read sequences present. Combinations of any of these are also possible, e.g., a population of nucleic acid probes may comprise between 10 and 15 read sequences in total.

As a non-limiting example of an approach to combinatorially producing a relatively large number of nucleic acid probes from a relatively small number of read sequences, in a population of 6 different types of nucleic acid probes, each comprising one or more read sequences, the total number of read sequences within the population may be no greater than 4. It should be understood that although 4 read sequences are used in this example for ease of explanation, in other embodiments, larger numbers of nucleic acid probes may be realized, for example, using 5, 8, 10, 16, 32, etc. or more read sequences, or any other suitable number of read sequences described herein, depending on the application. If each of the primary nucleic acid probes contains two different read sequences, then by using 4 such read sequences (A, B, C, and D), up to 6 probes may be separately identified. It should be noted that in this example, the ordering of read sequences on a nucleic acid probe is not essential, i.e., "AB" and "BA" may be treated as being synonymous (although in other embodiments, the ordering of read sequences may be essential and "AB" and "BA" may not necessarily be synonymous). Similarly, if 5 read sequences are used (A, B, C, D, and E) in the population of primary nucleic acid probes, up to 10 probes may be separately identified. For example, one of ordinary skill in the art would understand that, for k read sequences in a population with n read sequences on each probe, up to $\binom{n}{k}$ different probes may be produced, assuming that the ordering of read sequences is not essential; because not all of the probes need to have the same number of read sequences and not all combinations of read sequences need to be used in every embodiment, either more or less than this number of different probes may also be used in certain embodiments. In addition, it should also be understood that the number of read sequences on each probe need not be identical in some embodiments. For instance example, some probes may contain 2 read sequences while other probes may contain 3 read sequences.

In some aspects, the read sequences and/or the pattern of binding of nucleic acid probes within the cells may be used to define an error-detecting and/or an error-correcting code, for example, to reduce or prevent misidentification or errors of the nucleic acids. Thus, for example, if binding is indicated (e.g., as determined using a signaling entity), then the location may be identified with a "1"; conversely, if no binding is indicated, then the location may be identified with a "0" (or vice versa, in some cases). Multiple rounds of binding determinations, e.g., using different nucleic acid probes, can then be used to create a "codeword," e.g., for that spatial location. In some embodiments, the codeword may be subjected to error detection and/or correction. For instance, the codewords may be organized such that, if no match is found for a given set of read sequences or binding pattern of nucleic acid probes, then the match may be identified as an error, and optionally, error correction may be applied sequences to determine the correct target for the nucleic acid probes. In some cases, the codewords may have fewer "letters" or positions that the total number of nucleic acids encoded by the codewords, e.g. where each codeword encodes a different nucleic acid.

Such error-detecting and/or the error-correction code may take a variety of forms. A variety of such codes have previously been developed in other contexts such as the telecommunications industry, such as Golay codes or Hamming codes. In one set of embodiments, the read sequences or binding patterns of the nucleic acid probes are assigned such that not every possible combination is assigned.

For example, if 4 read sequences are possible and a primary nucleic acid probe contains 2 read sequences, then up to 6 primary nucleic acid probes could be identified; but the number of primary nucleic acid probes used may be less than 6. Similarly, for k read sequences in a population with n read sequences on each primary nucleic acid probe, $$\binom{n}{k}$$

different probes may be produced, but the number of primary nucleic acid probes that are used may be any number more or less than $$\binom{n}{k}.$$

In addition, these may be randomly assigned, or assigned in specific ways to increase the ability to detect and/or correct errors.

As another example, if multiple rounds of nucleic acid probes are used, the number of rounds may be arbitrarily chosen. If in each round, each target can give two possible outcomes, such as being detected or not being detected, up to $2^n$ different targets may be possible for n rounds of probes, but the number of nucleic acid targets that are actually used may be any number less than $2^n$. For example, if in each round, each target can give more than two possible outcomes, such as being detected in different color channels, more than $2^n$ (e.g. $3^n$, $4^n$ . . . ) different targets may be possible for n rounds of probes. In some cases, the number of nucleic acid targets that are actually used may be any number less than this number. In addition, these may be randomly assigned, or assigned in specific ways to increase the ability to detect and/or correct errors.

For example, in one set of embodiments, the codewords or nucleic acid probes may be assigned within a code space such that the assignments are separated by a Hamming distance, which measures the number of incorrect "reads" in a given pattern that cause the nucleic acid probe to be misinterpreted as a different valid nucleic acid probe. In certain cases, the Hamming distance may be at least 2, at least 3, at least 4, at least 5, at least 6, or the like. In addition, in one set of embodiments, the assignments may be formed as a Hamming code, for instance, a Hamming(7, 4) code, a Hamming(15, 11) code, a Hamming(31, 26) code, a Hamming(63, 57) code, a Hamming(127, 120) code, etc. In another set of embodiments, the assignments may form a SECDED code, e.g., a SECDED(8,4) code, a SECDED(16, 4) code, a SCEDED(16, 11) code, a SCEDED(22, 16) code, a SCEDED(39, 32) code, a SCEDED(72, 64) code, etc. In yet another set of embodiments, the assignments may form an extended binary Golay code, a perfect binary Golay code, or a ternary Golay code. In another set of embodiments, the assignments may represent a subset of the possible values taken from any of the codes described above.

For example, a code with the same error correcting properties of the SECDED code may be formed by using only binary words that contain a fixed number of '1' bits, such as 4, to encode the targets. In another set of embodiments, the assignments may represent a subset of the possible values taken from codes described above for the purpose of addressing asymmetric readout errors. For example, in some cases, a code in which the number of '1' bits may be fixed for all used binary words may eliminate the biased measurement of words with different numbers of '1's when the rate at which '0' bits are measured as '1's or '1' bits are measured as '0's are different.

Accordingly, in some embodiments, once the codeword is determined (e.g., as discussed herein), the codeword may be compared to the known nucleic acid codewords. If a match is found, then the nucleic acid target can be identified or determined. If no match is found, then an error in the reading of the codeword may be identified. In some cases, error correction can also be applied to determine the correct codeword, and thus resulting in the correct identity of the nucleic acid target. In some cases, the codewords may be selected such that, assuming that there is only one error present, only one possible correct codeword is available, and thus, only one correct identity of the nucleic acid target is possible. In some cases, this may also be generalized to larger codeword spacings or Hamming distances; for instance, the codewords may be selected such that if two, three, or four errors are present (or more in some cases), only one possible correct codeword is available, and thus, only one correct identity of the nucleic acid targets is possible.

The error-correcting code may be a binary error-correcting code, or it may be based on other numbering systems, e.g., ternary or quaternary error-correcting codes. For instance, in one set of embodiments, more than one type of signaling entity may be used and assigned to different numbers within the error-correcting code. Thus, as a non-limiting example, a first signaling entity (or more than one signaling entity, in some cases) may be assigned as "1" and a second signaling entity (or more than one signaling entity, in some cases) may be assigned as "2" (with "0" indicating no signaling entity present), and the codewords distributed to define a ternary error-correcting code. Similarly, a third signaling entity may additionally be assigned as "3" to make a quaternary error-correcting code, etc. Non-limiting examples of such codes include the Reed-Solomon erasure codes and generalizations thereof.

In addition, the code can also be selected in some embodiments through random selection of a sub-set of all possible codewords. For example, a random subset of binary codewords of length n code be selected. In some cases, these codewords can be separated by Hamming distances, i.e. the number of bits that must be flipped to convert one into another, so that some of the used codewords maintain some error robust or correcting abilities. In some embodiments, approaches such as next-generations sequencing can be used to measure the random subset of codewords used and error robustness and error correction could be applied selectively on the codewords that satisfy the constraints necessary for these properties.

As discussed above, in certain aspects, signaling entities are determined, e.g., to determine nucleic acid probes and/or to create codewords. In some cases, signaling entities within the cells may be determined, e.g., spatially, using a variety of techniques. In some embodiments, the signaling entities may be fluorescent, and techniques for determining fluorescence within the cells, such as fluorescence microscopy or confocal microscopy, may be used to spatially identify the positions of signaling entities within a cell. In some cases, the positions of entities within the cells may be determined in two or even three dimensions. In addition, in some embodiments, more than one signaling entity may be determined at a time (e.g., signaling entities with different colors or emissions), and/or sequentially.

In addition, in some embodiments, a confidence level for the identified nucleic acid target may be determined. For example, the confidence level may be determined using a ratio of the number of exact matches to the number of matches having one or more one-bit errors. In some cases, only matches having a confidence ratio greater than a certain value may be used. For instance, in certain embodiments, matches may be accepted only if the confidence ratio for the match is greater than about 0.01, greater than about 0.03, greater than about 0.05, greater than about 0.1, greater than about 0.3, greater than about 0.5, greater than about 1, greater than about 3, greater than about 5, greater than about 10, greater than about 30, greater than about 50, greater than about 100, greater than about 300, greater than about 500, greater than about 1000, or any other suitable value. In addition, in some embodiments, matches may be accepted only if the confidence ratio for the identified nucleic acid target is greater than an internal standard or false positive control by about 0.01, about 0.03, about 0.05, about 0.1, about 0.3, about 0.5, about 1, about 3, about 5, about 10, about 30, about 50, about 100, about 300, about 500, about 1000, or any other suitable value In some embodiments, the spatial positions of the entities (and thus, nucleic acid probes that the entities may be associated with) may be determined at relatively high resolutions. For instance, the positions may be determined at spatial resolutions of better than about 100 micrometers, better than about 30 micrometers, better than about 10 micrometers, better than about 3 micrometers, better than about 1 micrometer, better than about 800 nm, better than about 600 nm, better than about 500 nm, better than about 400 nm, better than about 300 nm, better than about 200 nm, better than about 100 nm, better than about 90 nm, better than about 80 nm, better than about 70 nm, better than about 60 nm, better than about 50 nm, better than about 40 nm, better than about 30 nm, better than about 20 nm, or better than about 10 nm, etc.

There are a variety of techniques able to determine or image the spatial positions of entities optically, e.g., using fluorescence microscopy. In some cases, the spatial positions may be determined at super resolutions, or at resolutions better than the wavelength of light or the diffraction limit. Non-limiting examples include STORM (stochastic optical reconstruction microscopy), STED (stimulated emission depletion microscopy), NSOM (Near-field Scanning Optical Microscopy), 4Pi microscopy, SIM (Structured Illumination Microscopy), SMI (Spatially Modulated Illumination) microscopy, RESOLFT (Reversible Saturable Optically Linear Fluorescence Transition Microscopy), GSD (Ground State Depletion Microscopy), SSIM (Saturated Structured-Illumination Microscopy), SPDM (Spectral Precision Distance Microscopy), Photo-Activated Localization Microscopy (PALM), Fluorescence Photoactivation Localization Microscopy (FPALM), LIMON (3D Light Microscopical Nanosizing Microscopy), Super-resolution optical fluctuation imaging (SOFI), or the like. See, e.g., U.S. Pat. No. 7,838,302, issued Nov. 23, 2010, entitled "Sub-Diffraction Limit Image Resolution and Other Imaging Techniques," by Zhuang, et al.; U.S. Pat. No. 8,564,792, issued Oct. 22, 2013, entitled "Sub-diffraction Limit Image Resolution in Three Dimensions," by Zhuang, et al.; or Int. Pat. Apl. Pub. No. WO 2013/090360, published Jun. 20, 2013, entitled "High Resolution Dual-Objective Microscopy," by Zhuang, et al., each incorporated herein by reference in their entireties.

As an illustrative non-limiting example, in one set of embodiments, the cells may be imaged with a high numerical aperture, oil immersion objective with 100× magnification and light collected on an electron-multiplying CCD camera. In another example, the cells could be imaged with a high numerical aperture, oil immersion lens with 40× magnification and light collected with a wide-field scientific CMOS camera. With different combinations of objectives and cameras, a single field of view may correspond to no less than 40×40 microns, 80×80 microns, 120×120 microns, 240×240 microns, 340×340 microns, or 500×500 microns, etc. in various non-limiting embodiments. Similarly, a single camera pixel may correspond, in some embodiments, to regions of the cells of no less than 80×80 nm, 120×120 nm, 160×160 nm, 240×240 nm, or 300×300 nm, etc. In another example, the cells may be imaged with a low numerical aperture, air lens with 10× magnification and light collected with a sCMOS camera. In additional embodiments, the cells may be optically sectioned by illuminating it via a single or multiple scanned diffraction limited foci generated either by scanning mirrors or a spinning disk and the collected passed through a single or multiple pinholes. In another embodiment, the cells may also be illuminated via thin sheet of light generated via any one of multiple methods known to those versed in the art.

In one embodiment, the cells may be illuminated by single Gaussian mode laser lines. In some embodiments, the illumination profiled may be flattened by passing these laser lines through a multimode fiber that is vibrated via piezoelectric or other mechanical means. In some embodiments, the illumination profile may be flattened by passing single-mode, Gaussian beams through a variety of refractive beam shapers, such as the piShaper or a series of stacked Powell lenses. In yet another set of embodiments, the Gaussian beams may be passed through a variety of different diffusing elements, such as ground glass or engineered diffusers, which may be spun in some cases at high speeds to remove residual laser speckle. In yet another embodiment, laser illumination may be passed through a series of lenslet arrays to produce overlapping images of the illumination that approximate a flat illumination field.

In addition, the signaling entity may be inactivated in some cases. For example, in some embodiments, a first secondary nucleic acid probe containing a signaling entity may be applied to the cells that can recognize a first read sequence, then the first secondary nucleic acid probe can be inactivated before a second secondary nucleic acid probe is applied to the cells. If multiple signaling entities are used, the same or different techniques may be used to inactivate the signaling entities, and some or all of the multiple signaling entities may be inactivated, e.g., sequentially or simultaneously.

Inactivation may be caused by removal of the signaling entity (e.g., from the cells, or from the nucleic acid probe, etc.), and/or by chemically altering the signaling entity in some fashion, e.g., by photobleaching the signaling entity, bleaching or chemically altering the structure of the signaling entity, e.g., by reduction, etc.). For instance, in one set of embodiments, a fluorescent signaling entity may be inactivated by chemical or optical techniques such as oxidation, photobleaching, chemically bleaching, stringent washing or enzymatic digestion or reaction by exposure to an enzyme, dissociating the signaling entity from other components (e.g., a probe), chemical reaction of the signaling entity (e.g., to a reactant able to alter the structure of the signaling entity) or the like. For instance, bleaching may occur by exposure to oxygen, reducing agents, or the signaling entity could be chemically cleaved from the nucleic acid probe (for example, using tris(2-carboxyethyl)phosphine) and washed away via fluid flow.

In some embodiments, various nucleic acid probes (including primary and/or secondary nucleic acid probes) may include one or more signaling entities. If more than one nucleic acid probe is used, the signaling entities may each by the same or different. In certain embodiments, a signaling entity is any entity able to emit light. For instance, in one embodiment, the signaling entity is fluorescent. In other embodiments, the signaling entity may be phosphorescent, radioactive, absorptive, etc. In some cases, the signaling entity is any entity that can be determined within the cells at relatively high resolutions, e.g., at resolutions better than the wavelength of visible light or the diffraction limit. The signaling entity may be, for example, a dye, a small molecule, a peptide or protein, or the like. The signaling entity may be a single molecule in some cases. If multiple secondary nucleic acid probes are used, the nucleic acid probes may comprise the same or different signaling entities.

Non-limiting examples of signaling entities include fluorescent entities (fluorophores) or phosphorescent entities, for example, cyanine dyes (e.g., Cy2, Cy3, Cy3B, Cy5, Cy5.5, Cy7, etc.), Alexa Fluor dyes, Atto dyes, photoswtichable dyes, photoactivatable dyes, fluorescent dyes, metal nanoparticles, semiconductor nanoparticles or "quantum dots", fluorescent proteins such as GFP (Green Fluorescent Protein), or photoactivabale fluorescent proteins, such as PAGFP, PSCFP, PSCFP2, Dendra, Dendra2, EosFP, tdEos, mEos2, mEos3, PAmCherry, PAtagRFP, mMaple, mMaple2, and mMaple3. Other suitable signaling entities are known to those of ordinary skill in the art. See, e.g., U.S. Pat. No. 7,838,302 or U.S. Pat. Apl. Ser. No. 61/979,436, each incorporated herein by reference in its entirety.

In one set of embodiments, the signaling entity may be attached to an oligonucleotide sequence via a bond that can be cleaved to release the signaling entity. In one set of embodiments, a fluorophore may be conjugated to an oligonucleotide via a cleavable bond, such as a photocleavable bond. Non-limiting examples of photocleavable bonds include, but are not limited to, 1-(2-nitrophenyl)ethyl, 2☐nitrobenzyl, biotin phosphoramidite, acrylic phosphoramidite, diethylaminocoumarin, 1-(4,5-dimethoxy-2-nitrophenyl)ethyl, cyclo-dodecyl (dimethoxy-2-nitrophenyl)ethyl, 4-aminomethyl-3-nitrobenzyl, (4-nitro-3-(1-chlorocarbonyloxyethyl)phenyl)methyl-S-acetylthioic acid ester, (4-nitro-3-(1-thlorocarbonyloxyethyl)phenyl)methyl-3-(2-pyridyldithiopropionic acid) ester, 3-(4,4'-dimethoxytrityl)-1-(2-nitrophenyl)-propane-1,3-diol-[2-cyanoethyl-(N,N-diisopropyl)]-phosphoramidite, 1-[2-nitro-5-(6-trifluoroacetylcaproamidomethyl)phenyl]-ethyl-[2-cyanoethyl-(N,N-diisopropyl)]-phosphoramidite, 1-[2-nitro-5-(6-(4,4'-dimethoxytrityloxy)butyramidomethyl)phenyl]-ethyl-[2-cyanoethyl-(N,N-diisopropyl)]-phosphoramidite, 1-[2-nitro-5-(6-(N-(4,4'-dimethoxytrityl))-biotinamidocaproamido-methyl)phenyl]-ethyl-[2-cyanoethyl-(N,N-diisopropyl)]-phosphoramidite, or similar linkers. In another set of embodiments, the fluorophore may be conjugated to an oligonucleotide via a disulfide bond. The disulfide bond may be cleaved by a variety of reducing agents such as, but not limited to, dithiothreitol, dithioerythritol, beta-mercaptoethanol, sodium borohydride, thioredoxin, glutaredoxin, trypsinogen, hydrazine, diisobutylaluminum hydride, oxalic acid, formic acid, ascorbic acid, phosphorous acid, tin chloride, glutathione, thioglycolate, 2,3-dimercaptopropanol, 2-mercaptoethylamine, 2-aminoethanol, tris(2-carboxyethyl)phosphine, bis(2-mercaptoethyl) sulfone, N,N'-dimethyl-N,N'-bis(mercaptoacetyl)hydrazine, 3-mercaptoproptionate, dimethylformamide, thiopropyl-agarose, tri-n-butylphosphine, cysteine, iron sulfate, sodium sulfite, phosphite, hypophosphite, phosphorothioate, or the like, and/or combinations of any of these. In another embodiment, the fluorophore may be conjugated to an oligonucleotide via one or more phosphorothioate modified nucleotides in which the sulfur modification replaces the bridging and/or non-bridging oxygen. The fluorophore may be cleaved from the oligonucleotide, in certain embodiments, via addition of compounds such as but not limited to iodoethanol, iodine mixed in ethanol, silver nitrate, or mercury chloride. In yet another set of embodiments, the signaling entity may be chemically inactivated through reduction or oxidation. For example, in one embodiment, a chromophore such as Cy5 or Cy7 may be reduced using sodium borohydride to a stable, non-fluorescence state. In still another set of embodiments, a fluorophore may be conjugated to an oligonucleotide via an azo bond, and the azo bond may be cleaved with 2-[(2-N-arylamino)phenylazo]pyridine. In yet another set of embodiments, a fluorophore may be conjugated to an oligonucleotide via a suitable nucleic acid segment that can be cleaved upon suitable exposure to DNAse, e.g., an exodeoxyribonuclease or an endodeoxyribonuclease. Examples include, but are not limited to, deoxyribonuclease I or deoxyribonuclease II. In one set of embodiments, the cleavage may occur via a restriction endonuclease. Non-limiting examples of potentially suitable restriction endonucleases include BamHI, BsrI, NotI, XmaI, PspAI, DpnI, MboI, MnlI, Eco57I, Ksp632I, DraIII, AhaII, SmaI, MluI, HpaI, ApaI, BclI, BstEII, TaqI, EcoRI, SacI, HindII, HaeII, DraII, Tsp509I, Sau3AI, PacI, etc. Over 3000 restriction enzymes have been studied in detail, and more than 600 of these are available commercially. In yet another set of embodiments, a fluorophore may be conjugated to biotin, and the oligonucleotide conjugated to avidin or streptavidin. An interaction between biotin and avidin or streptavidin allows the fluorophore to be conjugated to the oligonucleotide, while sufficient exposure to an excess of addition, free biotin could "outcompete" the linkage and thereby cause cleavage to occur. In addition, in another set of embodiments, the probes may be removed using corresponding "toe-hold-probes," which comprise the same sequence as the probe, as well as an extra number of bases of homology to the encoding probes (e.g., 1-20 extra bases, for example, 5 extra bases). These probes may remove the labeled readout probe through a strand-displacement interaction.

As used herein, the term "light" generally refers to electromagnetic radiation, having any suitable wavelength (or equivalently, frequency). For instance, in some embodiments, the light may include wavelengths in the optical or visual range (for example, having a wavelength of between about 400 nm and about 700 nm, i.e., "visible light"), infrared wavelengths (for example, having a wavelength of between about 300 micrometers and 700 nm), ultraviolet wavelengths (for example, having a wavelength of between about 400 nm and about 10 nm), or the like. In certain cases, as discussed in detail below, more than one entity may be used, i.e., entities that are chemically different or distinct, for example, structurally. However, in other cases, the entities may be chemically identical or at least substantially chemically identical.

In one set of embodiments, the signaling entity is "switchable," i.e., the entity can be switched between two or more states, at least one of which emits light having a desired wavelength. In the other state(s), the entity may emit no light, or emit light at a different wavelength. For instance, an entity may be "activated" to a first state able to produce light having a desired wavelength, and "deactivated" to a second state not able to emit light of the same wavelength. An entity is "photoactivatable" if it can be activated by incident light of a suitable wavelength. As a non-limiting example, Cy5, can be switched between a fluorescent and a dark state in a controlled and reversible manner by light of different wavelengths, i.e., 633 nm (or 642 nm, 647 nm, 656 nm) red light can switch or deactivate Cy5 to a stable dark state, while 405 nm green light can switch or activate the Cy5 back to the fluorescent state. In some cases, the entity can be reversibly switched between the two or more states, e.g., upon exposure to the proper stimuli. For example, a first stimuli (e.g., a first wavelength of light) may be used to activate the switchable entity, while a second stimuli (e.g., a second wavelength of light) may be used to deactivate the switchable entity, for instance, to a non-emitting state. Any suitable method may be used to activate the entity. For example, in one embodiment, incident light of a suitable wavelength may be used to activate the entity to emit light, i.e., the entity is "photoswitchable." Thus, the photoswitchable entity can be switched between different light-emitting or non-emitting states by incident light, e.g., of different wavelengths. The light may be monochromatic (e.g., produced using a laser)

or polychromatic. In another embodiment, the entity may be activated upon stimulation by electric field and/or magnetic field. In other embodiments, the entity may be activated upon exposure to a suitable chemical environment, e.g., by adjusting the pH, or inducing a reversible chemical reaction involving the entity, etc. Similarly, any suitable method may be used to deactivate the entity, and the methods of activating and deactivating the entity need not be the same. For instance, the entity may be deactivated upon exposure to incident light of a suitable wavelength, or the entity may be deactivated by waiting a sufficient time.

Typically, a "switchable" entity can be identified by one of ordinary skill in the art by determining conditions under which an entity in a first state can emit light when exposed to an excitation wavelength, switching the entity from the first state to the second state, e.g., upon exposure to light of a switching wavelength, then showing that the entity, while in the second state can no longer emit light (or emits light at a much reduced intensity) when exposed to the excitation wavelength.

In one set of embodiments, as discussed, a switchable entity may be switched upon exposure to light. In some cases, the light used to activate the switchable entity may come from an external source, e.g., a light source such as a laser light source, another light-emitting entity proximate the switchable entity, etc. The second, light emitting entity, in some cases, may be a fluorescent entity, and in certain embodiments, the second, light-emitting entity may itself also be a switchable entity.

In some embodiments, the switchable entity includes a first, light-emitting portion (e.g., a fluorophore), and a second portion that activates or "switches" the first portion. For example, upon exposure to light, the second portion of the switchable entity may activate the first portion, causing the first portion to emit light. Examples of activator portions include, but are not limited to, Alexa Fluor 405 (Invitrogen), Alexa Fluor 488 (Invitrogen), Cy2 (GE Healthcare), Cy3 (GE Healthcare), Cy3B (GE Healthcare), Cy3.5 (GE Healthcare), or other suitable dyes. Examples of light-emitting portions include, but are not limited to, Cy5, Cy5.5 (GE Healthcare), Cy7 (GE Healthcare), Alexa Fluor 647 (Invitrogen), Alexa Fluor 680 (Invitrogen), Alexa Fluor 700 (Invitrogen), Alexa Fluor 750 (Invitrogen), Alexa Fluor 790 (Invitrogen), DiD, DiR, YOYO-3 (Invitrogen), YO-PRO-3 (Invitrogen), TOT-3 (Invitrogen), TO-PRO-3 (Invitrogen) or other suitable dyes. These may linked together, e.g., covalently, for example, directly, or through a linker, e.g., forming compounds such as, but not limited to, Cy5-Alexa Fluor 405, Cy5-Alexa Fluor 488, Cy5-Cy2, Cy5-Cy3, Cy5-Cy3.5, Cy5.5-Alexa Fluor 405, Cy5.5-Alexa Fluor 488, Cy5.5-Cy2, Cy5.5-Cy3, Cy5.5-Cy3.5, Cy7-Alexa Fluor 405, Cy7-Alexa Fluor 488, Cy7-Cy2, Cy7-Cy3, Cy7-Cy3.5, Alexa Fluor 647-Alexa Fluor 405, Alexa Fluor 647-Alexa Fluor 488, Alexa Fluor 647-Cy2, Alexa Fluor 647-Cy3, Alexa Fluor 647-Cy3.5, Alexa Fluor 750-Alexa Fluor 405, Alexa Fluor 750-Alexa Fluor 488, Alexa Fluor 750-Cy2, Alexa Fluor 750-Cy3, or Alexa Fluor 750-Cy3.5. Those of ordinary skill in the art will be aware of the structures of these and other compounds, many of which are available commercially. The portions may be linked via a covalent bond, or by a linker, such as those described in detail below. Other light-emitting or activator portions may include portions having two quaternized nitrogen atoms joined by a polymethine chain, where each nitrogen is independently part of a heteroaromatic moiety, such as pyrrole, imidazole, thiazole, pyridine, quinoine, indole, benzothiazole, etc., or part of a nonaromatic amine. In some cases, there may be 5, 6, 7, 8, 9, or more carbon atoms between the two nitrogen atoms.

Another aspect of the invention is directed to a computer-implemented method. For instance, a computer and/or an automated system may be provided that is able to automatically and/or repetitively perform any of the methods described herein. As used herein, "automated" devices refer to devices that are able to operate without human direction, i.e., an automated device can perform a function during a period of time after any human has finished taking any action to promote the function, e.g. by entering instructions into a computer to start the process. Typically, automated equipment can perform repetitive functions after this point in time. The processing steps may also be recorded onto a machine-readable medium in some cases.

For example, in some cases, a computer may be used to control imaging of the cells, e.g., using fluorescence microscopy, STORM or other super-resolution techniques such as those described herein. In some cases, the computer may also control operations such as drift correction, physical registration, hybridization and cluster alignment in image analysis, cluster decoding (e.g., fluorescent cluster decoding), error detection or correction (e.g., as discussed herein), noise reduction, identification of foreground features from background features (such as noise or debris in images), or the like. As an example, the computer may be used to control activation and/or excitation of signaling entities within the cells, and/or the acquisition of images of the signaling entities. In one set of embodiments, cells may be excited using light having various wavelengths and/or intensities, and the sequence of the wavelengths of light used to excite the cells may be correlated, using a computer, to the images acquired of the cells containing the signaling entities. For instance, the computer may apply light having various wavelengths and/or intensities to the cells to yield different average numbers of signaling entities in each region of interest (e.g., one activated entity per location, two activated entities per location, etc.). In some cases, this information may be used to construct an image and/or determine the locations of the signaling entities, in some cases at high resolutions, as noted above.

In some aspects, the cells are positioned on a microscope. In some cases, the microscope may contain one or more channels, such as microfluidic channels, to direct or control fluid to or from the cells. For instance, in one embodiment, nucleic acid probes such as those discussed herein may be introduced and/or removed from the cells by flowing fluid through one or more channels to or from the cells. In some cases, there may also be one or more chambers or reservoirs for holding fluid, e.g., in fluidic communication with the channel, and/or with the cells. Those of ordinary skill in the art will be familiar with channels, including microfluidic channels, for moving fluid to or from the cells.

The following documents are each incorporated herein by reference in their entireties: U.S. Provisional Patent Application Ser. No. 62/419,033, filed Nov. 8, 2016, entitled "Matrix Imprinting and Clearing"; International Patent Application Serial No. PCT/US17/60570; International Patent Application Serial No. PCT/US17/60558; International Patent Application Publication No. WO 2016/018960; and International Patent Application Publication No. WO 2016/018963. U.S. Provisional Patent Application Ser. No. 62/511,920, filed May 26, 2017, entitled "High-Throughput, Image-Based Screening of Genetic Variant Libraries," by Zhuang, et al., is also incorporated herein by reference in its entirety.

The following examples are intended to illustrate certain embodiments of the present invention, but do not exemplify the full scope of the invention.

Example 1

The ability to detect the genetic variant present in a library of surface adhered cells would allow highly versatile image based measurements to be used to determine phenotypes of genetic variant libraries. This example illustrates a new high-throughput, imaging-based screening method that allows the characterization of both phenotype and genotype for pooled populations of genetically diverse cells.

In this example, genetic variants are associated with a barcode composed of a series of short oligonucleotide hybridization sites. After introducing the barcoded genetic variant library into a population of cells and measuring phenotypes with imaging, the cells are fixed and the barcodes are determined using multiplexed error robust fluorescence in situ hybridization (MERFISH), a method that allows tens of thousands of barcodes to be read using combinatorial labeling plus sequential imaging. To test the feasibility and quantify the accuracy of this screening approach, a library was measured with a known phenotype, where half the library members have a fluorescent protein and half do not. In another example, similar methods were used to optimize the brightness and photostability of YFAST, a recently discovered fluorescent protein that becomes fluorescent upon binding to an exogenous chromophore. This allowed efficient screening of 20 million cells containing 160,000 unique barcodes and 60,000 unique mutants, which resulted in the identification of YFAST variants with substantially increased brightness and photostability.

In this example, to screen fluorescent protein mutant libraries for variants with improved properties, such as improved photostability and brightness, a unique barcode was introduced into each plasmid expressing a mutant fluorescent protein.

Each barcode was formed from a concatenation of hybridization sites encoding a N-bit binary word (FIG. 1A). Each of the N bit positions can have either a value of 0 or a value of 1 and for each possible bit value, a unique readout sequence was assigned. Altogether, there were 2N unique readout sequences in the barcode: readout sequence 1-0, readout sequence 1-1, readout sequence 2-0, readout sequence 2-1, . . . , readout sequence N-0, readout sequence N-1. For example, the binary word 101 . . . 1 would be encoded in a barcode consisting of readout sequence 1-1, followed by readout sequence 2-0, readout sequence 3-1, . . . , and finally readout sequence N-1.

Figure 1B:
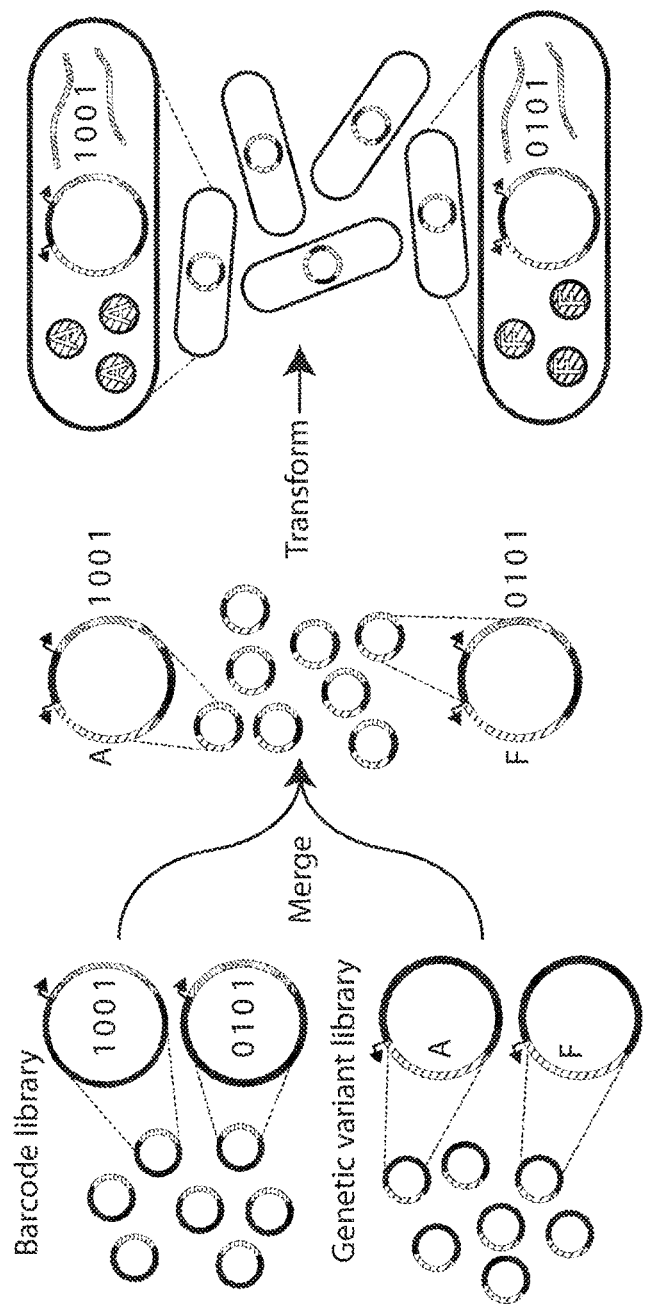

To create a barcoded library of genetic variants, the barcode library containing all possible N-bit barcodes and the library of genetic variants were merged so that the barcodes and genetic variants were associated randomly (FIG. 1B). The half of the plasmid containing the genetic variants from the genetic variant library was amplified and assembled with the amplified half of the plasmid containing the barcodes from the barcode library using isothermal assembly and the assembled product is electroporated into $E.\ coli$. To reduce the chance of a barcode appearing in the library associated with more than one genetic variant, the final barcoded mutant library was bottlenecked by limiting the number of cells to between 1% and 10% of the total barcode diversity of $2^N$. To determine which barcode was associated with which genetic variant, the plasmids were extracted from the $E.\ coli$ culture and sequenced by next generation sequencing to construct a look-up table. Still, a small probability remained that the same barcode appears associated with multiple mutants in a library. This situation was detected in the sequencing results and the affected barcodes are removed in further analysis. Within the $E.\ coli$ cells, the fluorescent protein and the barcode RNA were expressed from the plasmid, allowing the brightness and photostability of the fluorescent protein to be measured along with the identity of the barcode.

Figure 1C:
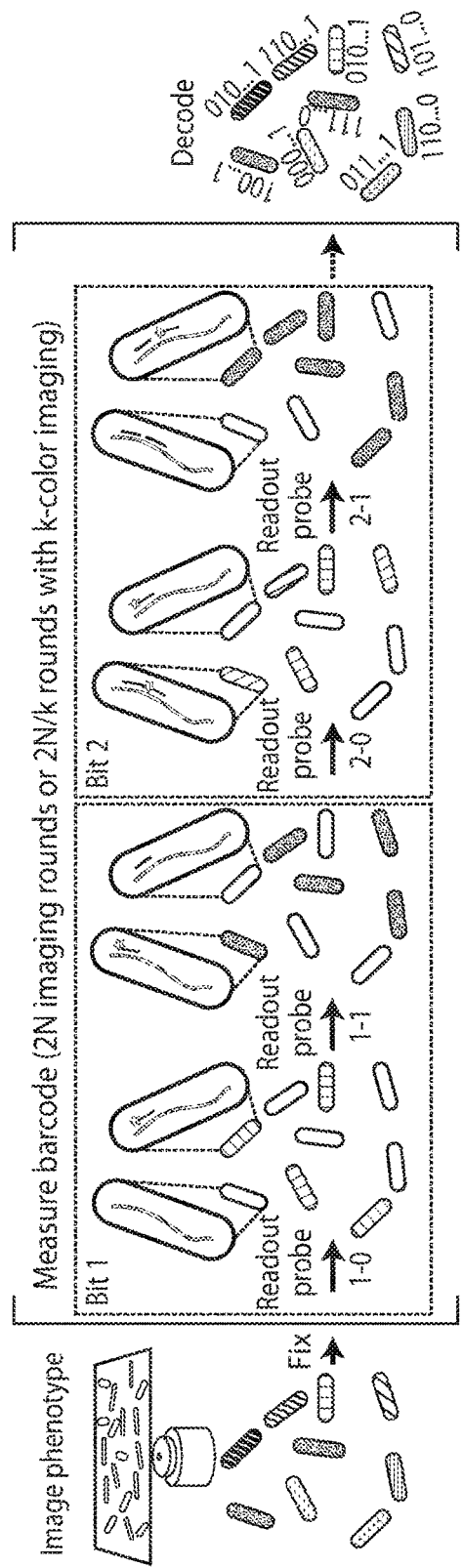

To screen the barcoded protein mutant library, the cells were adhered to a glass coverslip and their phenotypes, such as fluorescence intensity and photobleaching rate, were imaged while the cells were still alive (FIG. 1C). Then, the cells were fixed in methanol, without removing them from the microscope, and the barcode was read out using high-throughput imaging, such as multiplexed error-robust fluorescence in situ hybridization (MERFISH).

During the barcode readout process, multiple hybridization rounds were used and fluorescently labeled readout probes complementary to each readout sequence on the barcode were hybridized in each round to detect which readout sequences are present in which cells. First, readout probe 1-0, complementary to readout sequence 1-0, was introduced. It hybridizes to cells that contain readout sequence 1-0, namely the cells containing barcodes whose first bit is "0", causing those cells to become brightly fluorescent. All the cells were imaged and then the dye, attached to the readout probe by a disulfide bond, was reductively cleaved by TCEP (tris(2-carboxyethyl)phosphine) to make all cells non-fluorescent. Then, readout probe 1-1 was hybridized. Since every barcode contained either readout sequence 1-0 or readout sequence 1-1, the cells that did not become fluorescent in the first round should now become fluorescent. The value for bit 1 for each cell was then assigned based on the fluorescence intensity ratio between probe 1-0 and probe 1-1. The dye was then cleaved. This process was iterated until all N bits were probed. To reduce the number of hybridization rounds, three color imaging was used to allow three probes with spectrally distinct fluorescent dyes to be hybridized and imaged simultaneously.

Since each cell expresses many copies of its corresponding barcode RNA, the fluorescence signal was very bright, and hence the readout error rate for each bit is very small, an error correcting code was unnecessary and all $2^N$ possible barcodes could be used. But, as described above, to avoid a barcode appearing paired with multiple mutants in the same library, the number of unique library members was restricted to be between 1% and 10% the total barcode diversity of $2^N$ by bottlenecking. Still, with this binary encoding scheme, the number of possible binary words scaled exponentially with the number of bits, allowing millions of unique barcodes to be measured with only tens of hybridization rounds.

FIG. 1 shows a high-throughput, image-based screening method using massively multiplexed fluorescence in situ hybridization. FIG. 1A shows a schematic depiction of the barcode. Each barcode was formed from a concatenation of bit-encoding nucleotide sequences where each bit position has either the sequence corresponding to a "0" or a "1." FIG. 1B shows a schematic depiction of library construction. The library of barcodes was merged with a library of genetic variants and transformed into bacteria. The correspondence between the barcodes and genetic variants was determined by sequencing.

FIG. 1C is a schematic diagram of the image-based phenotype-genotype characterization. The phenotype is first characterized in surface-adhered cells. Then, the cells were fixed, and multiple rounds of hybridization were used to measure the barcodes. During the first round, readout probe 1-0 was added and cells with barcodes that read "0" in the first bit, which contained the readout sequence 1-0, should bind to the probe and become fluorescent, whereas cells with barcodes that read "1" in the first bit should remain dark. Once readout probe 1-0 was extinguished, readout probe 1-1 was added and the cells with barcodes that read "1" in the first bit, which contain the readout sequence 1-1, should become fluorescent. This difference in fluorescence intensity allows the value of bit 1 to be determined for each cell. This was repeated similarly for the remaining bits. After measuring all bits, the barcode was decoded, revealing the identity of each cell, the genotype of the genetic variant contained in the cell, and which phenotype the genotype corresponds to. FIG. 1C also demonstrates that the number of hybridization rounds can be reduced if multi-color imaging is utilized. Specifically, multiple readout probes, each conjugated to a different fluorophore, are hybridized simultaneously in one round, and multi-color imaging is used to probe the presence of each of these different readout probes.

Example 2

Figure 2A:
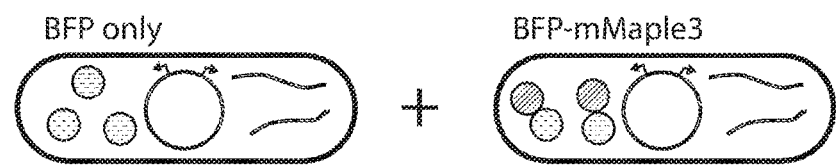
FIGS. 2A-2F illustrate the determination of cells containing barcodes of nucleic acids and the determination of the phenotype of those cells, in another embodiment of the invention.

To test the accuracy of this screening approach, a library was created containing only two "genetic variants," the mTagBFP2 gene and the fusion of mTagBFP2 and mMaple3 genes (FIG. 2A). Two libraries were created by merging a 21-bit barcode library, consisting of more than 2 million unique barcodes, with the two plasmids (containing the mTagBFP2 and mTagBFP2-mMaple3 genes, respectively) by isothermal assembly. Then, each of these complete libraries was bottlenecked to ~40,000 unique members and sequenced to determine which of the ~2 million possible barcodes are present in each library. Sequencing revealed that in the mixture of the two libraries, 80,000 unique barcodes are expected, which represent 4% of the possible barcodes.

Figure 2B:
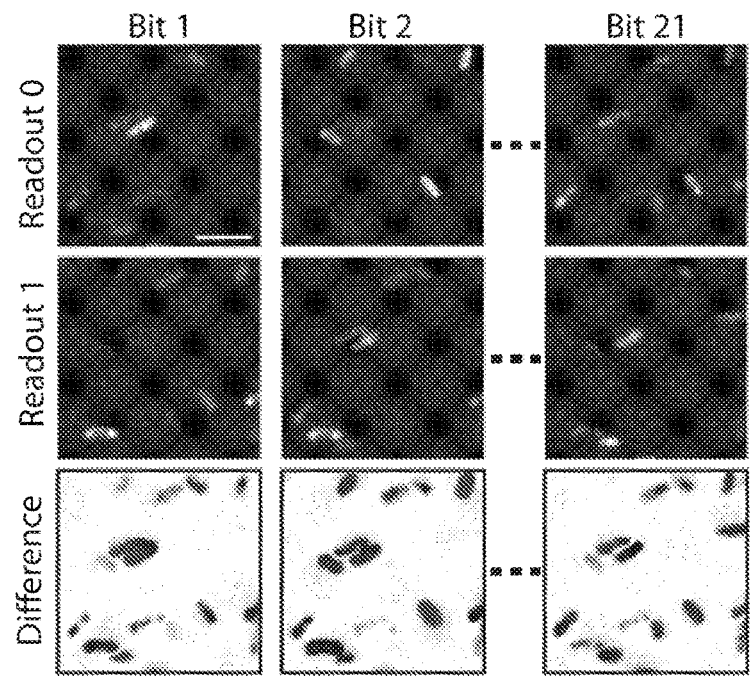
Figure 2C:
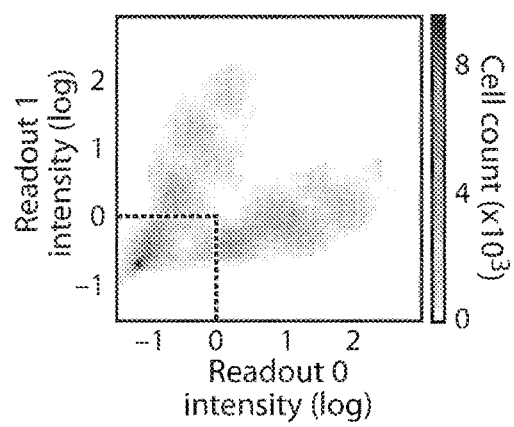

This combined library was characterized using this screening strategy. The fluorescence properties of the cells expressing mTagBFP2 or mTagBFP2-mMaple3 were measured by illuminating with 405 nm light to measure mTagBFP2 fluorescence, illuminating with 405 nm light for an additional ~4 s in order to switch the mMaple3 protein to its red-shifted fluorescent state, and then measuring the fluorescence intensity of the red-shifted mMaple3 by illuminating with 560 nm light. The cells were then fixed in methanol and barcodes were read out in each cell using the procedure described above. Indeed, as expected, cells that are bright for one readout of a given bit are dim for the other readout (FIG. 2B). For all 1.5 million cells observed, a two-dimensional (2D) histogram of the bit 1 measurements, i.e. the fluorescence intensities determined in the probe 1-0 imaging round and probe 1-1 imaging round, was constructed and this histogram suggested there were two distinct populations of cells (FIG. 2C). The first population appears bright when hybridized to probe 1-0 and dim when hybridized to probe 1-1 while the second population appears dim when hybridized to probe 1-0 and bright when hybridized to probe 1-1. This is consistent with the readout sequence 1-0 being present in the first population and readout sequence 1-1 being present in the second.

Figure 2D:
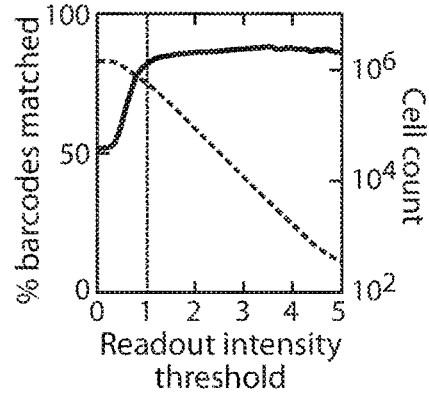
Figure 3:
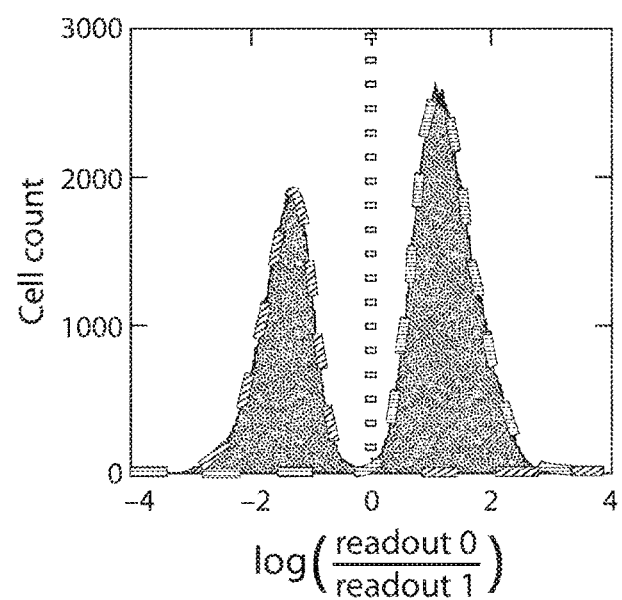
FIG. 3 illustrates the distribution of the ratio of readout 0 intensity to the readout 1 intensity for reading one bit of the barcode, in one embodiment of the invention.

However, a substantial fraction of cells appeared dark in both imaging rounds, possibly because they were not expressing sufficient barcode RNA, or they were insufficiently permeabilized for readout probe hybridization. A threshold intensity was used to remove these cells from further analysis. Specifically, each set of intensities for each readout probe was normalized by the median value of all corresponding measurements and cells where both normalized readout intensities for the "0" and the "1" readout fell below 1 for any bit were removed. More than 600,000 measured cells were brighter than this intensity threshold and the barcodes expressed in these cells are determined. Among these cells, 84% of them matched a barcode contained in the library pre-determined by sequencing (FIG. 2D). Among cells assigned to valid barcodes, the distribution of "0"-to-"1" probe-intensity ratios for each bit showed two distinct cell populations with essentially zero overlap (FIG. 3).

For the unmatched 16% of the cells, an experimental error must have occurred. Either the barcode is present in the library but it was not detected by sequencing or the barcode is not present in the library and an error occurred during barcode imaging. Those cells were not used in further analysis. However, the presence of this unmatched fraction suggested that some of the barcodes in the 84% cells that match the barcodes in the library could also be mis-identified. In order to determine this misidentification rate, it was first noted that the library only contained 4% of all possible barcodes for the 21-bit binary encoding used, so assuming that a readout error in the imaging process is equally likely to result in a cell being assigned any of the $2^{21}$ barcodes, there was a 96% chance that the error results in identifying a barcode that does not match one in the library.

Next, the probability that the barcode in a cell was incorrectly determined was denoted as x. Then, this probability x multiplied by 96% should be equal to 16%, the fraction of cells that were found containing barcodes that do not match any barcode in the library. Hence, x should be equal to 0.167 and the probability that the error results in a different barcode that is present in the library should be only 4% of x, which is ~0.67%. Therefore, the estimated misidentification rate, i.e. the probability that both an error occurs and the error yields a barcode this is already present in the library, is only less than one percent.

Figure 2E:
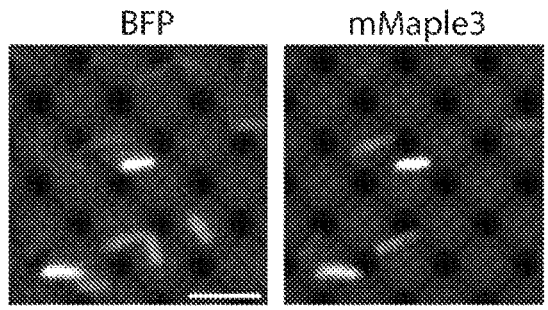
Figure 2F:
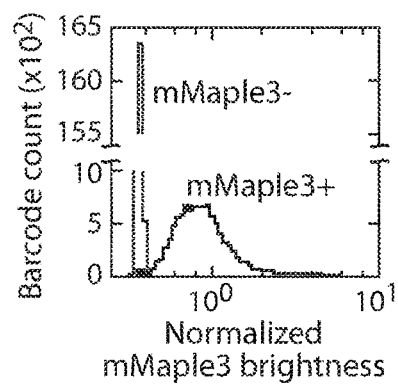

The fidelity of the barcode measurement could also be verified by considering the phenotype measurements described above to determine the mTagBFP2 fluorescence intensity and the mMaple3 fluorescence intensity of each cell (FIG. 2E). All cells with identical barcode classifications were grouped and the median ratio of mMaple3 intensity to mTagBFP2 intensity was calculated for each. Since from sequencing, it was determined which barcodes should be associated with mMaple3, the median intensity ratio for these barcodes was calculated and a histogram was calculated with these ratios. Using the same approach, a histogram of the ratio for the barcodes known to only be associated with mTagBFP2 was calculated (FIG. 2F). These two distributions were largely separated with only small overlap. A threshold was set based on the intersection point of the two histograms such that the cells with fluorescence intensity ratio larger than this threshold was classified as containing the mTagBFP2-mMaple3 fusion protein and the cells with the intensity ratio below the threshold as containing mTagBFP2. Based on this criterion, it was found that less than 1% of cells had their barcodes misidentified. It was noted that this was an overestimate of the error, since not all cells crossed the threshold value into the other population is necessarily due to barcode mis-identification—the intensity spread of the fluorescent proteins could contribute to the crossing too.

FIG. 2 illustrates measuring 1.5 million cells containing 80,000 unique barcodes using a 21-bit code. FIG. 2A is a schematic diagram of the library constituents. Among the 80,000 distinct barcodes, half were associated with the mTagBFP2 gene while the other half were associated with the mTagBFP2 gene fused to the mMaple3 gene. The cells containing plasmids harboring these barcodes and the associated fluorescent protein genes would express both the barcode RNA and the fluorescent proteins. FIG. 2B shows fluorescent images for each readout of each bit. The difference of the two readout images for each bit determined the value of that bit in each cell. The first row displayed the readout 0 images of each bit (i.e. images with readout probes 1-0, 2-0, . . . , N-0) for a field of view and the second row displayed the readout 1 images (i.e. images with readout probes 1-1, 2-1, . . . , N-1). The third row displayed the difference images with the darker shading indicating that readout 0 intensity is greater than the readout 1 intensity, and the lighter shading indicate the opposite. Each bit was assigned either a "0" value or a "1" value based on the ratio of the readout 0 intensity to readout 1 intensity.

FIG. 2C shows a two-dimensional histogram of normalized fluorescence intensities for readout 0 and readout 1 of bit 1 for each cell. The fluorescence intensities were normalized to the median values. The dotted line depicted the threshold used for eliminating cells that appear dim in both readouts. FIG. 2D shows the percent of barcodes decoded in the imaging experiment that match barcodes determined to be in the library by sequencing (left) and number of cells above the bit readout intensity threshold (right, downward-sloping line) with varying threshold magnitude. The dotted line corresponded with the threshold of 1 shown in FIG. 2C. FIG. 2E shows a fluorescence image of BFP and fluorescence image of post-activation mMaple3 in the same region as FIG. 2B. FIG. 2F shows histograms of median mMaple3-fluorescence intensity normalized to mTagBFP intensity for barcodes associated with the mMaple3-mTagBFP2 fusion gene (rightward curve) and for those associated with the mTagBFP2-gene (leftward curve).

FIG. 3 shows a histogram of the natural logarithm of the ratio of readout 0 intensity to readout 1 intensity for bit 1 for only cells that were assigned barcodes that match barcodes that were determined to be in the library by sequencing. The histogram was fit to a sum of two skewed Gaussian curves and each fit Gaussian is depicted (dashed lines). The vertical dotted line depicts the bit-calling threshold.

Example 3

Figure 4A:
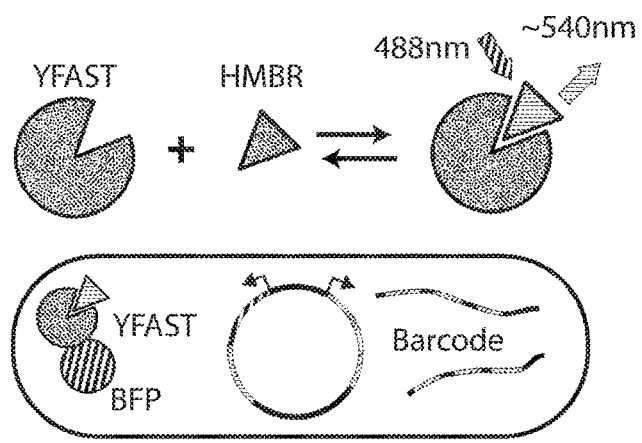
FIGS. 4A-4G illustrate screening of cells, in yet another embodiment of the invention.

To demonstrate the utility of a high-throughput approach for screening a large library of mutants to find proteins with desired properties, this example screened for increased photostability and increased brightness of a recently developed fluorescent protein, YFAST. YFAST is a protein that is not itself fluorescent, but only becomes fluorescent upon binding to an exogenous, GFP-like chromophore known as HMBR (FIG. 4A). Libraries of YFAST variants were created that contained variants with single amino acid mutations throughout the whole protein in addition to variants with multiple mutations in residues in the vicinity of the chromophore. These libraries were assembled by incorporating synthetized DNA oligonucleotides designed to have sequences corresponding to the desired mutations into a purification plasmid. This plasmid filters frameshift and nonsense errors from the pool by using a downstream translational fusion to the chloramphenicol resistance gene. Then, the library of YFAST variants was merged with the 21-bit barcode library so that a single, unique barcode was randomly associated with each variant. To normalize for variation in expression levels of YFAST between different cells, YFAST was fused to mTagBFP2, a fluorescent protein that is spectrally distinct from YFAST. To determine which barcode was associated with each genetic variant, the barcoded genetic variant library was sequenced using high-throughput sequencing.

Figure 4B:
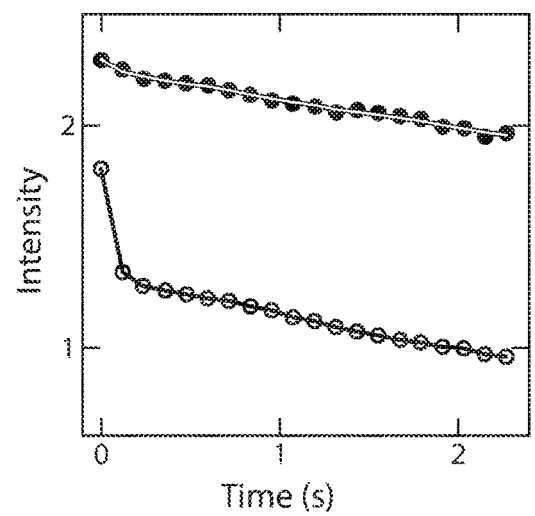
Figure 5:
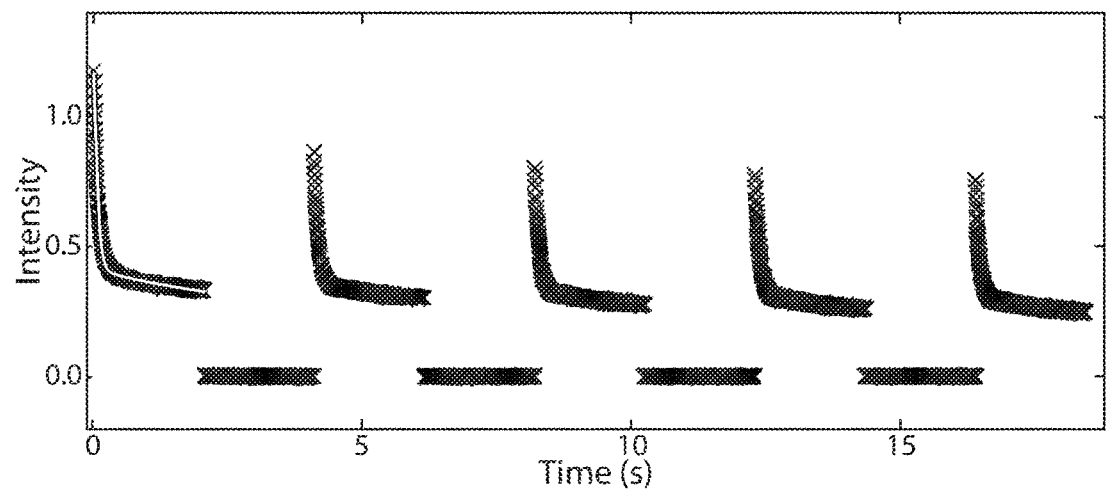
FIG. 5 illustrates the fluorescence decay and recovery of YFAST upon periodic illumination, in another embodiment of the invention.

The library of barcoded YFAST variants was inserted into E. coli and the E. coli were adhered to a glass surface for imaging. First, the photophysical properties of the YFAST variant in each cell were measured. The fluorescence intensity of mTagBFP2 was measured in one camera image under 405 nm illumination. Then the photobleaching time-course of YFAST was measured over 20 images with constant 488 nm illumination (FIG. 4B). The acquired images were segmented to determine the boundaries of each cell and the average intensity for each cell was calculated for each image. The fluorescence background upon 488 nm illumination was subtracted from the photobleaching time series for each cell and each time series was normalized for cell-to-cell variation in expression levels of YFAST by dividing by the measured 405 fluorescence intensity. Since YFAST exhibits biphasic fluorescence decay upon photobleaching (FIG. 5), the background subtracted and normalized intensity time series for each cell was fit to a double exponential with the rate of the fast exponential fixed to a constant value (FIG. 4B and FIG. 5). From the fit, the slow photobleaching amplitude, slow photobleaching rate, and fractional fast photobleaching amplitude were determined for each cell.

Figure 4C:
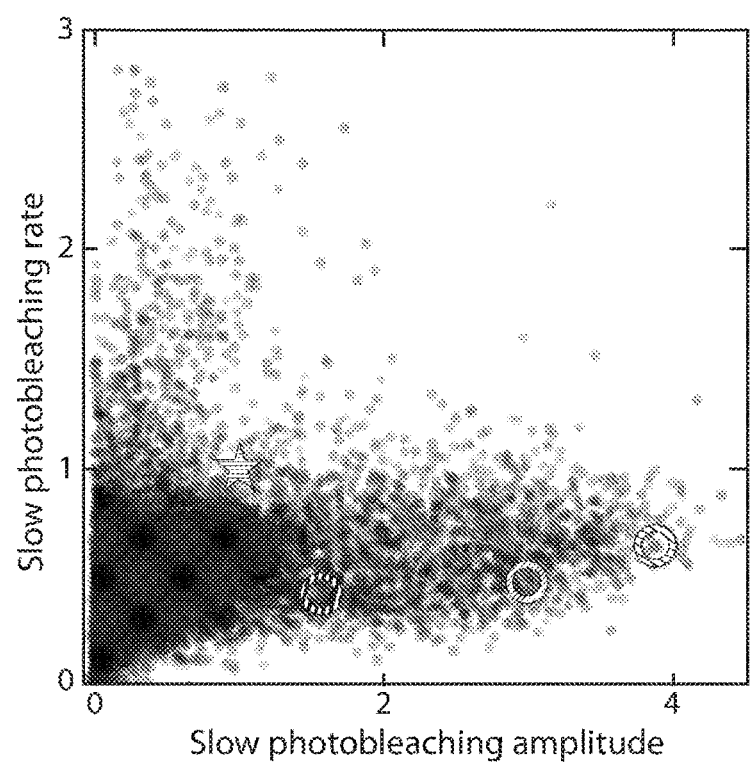
Figure 4D:
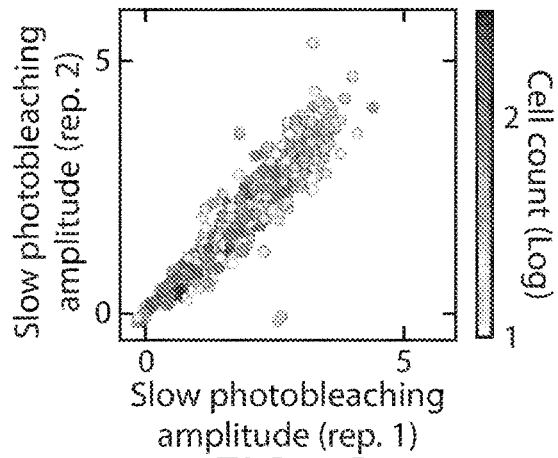
Figure 4F:
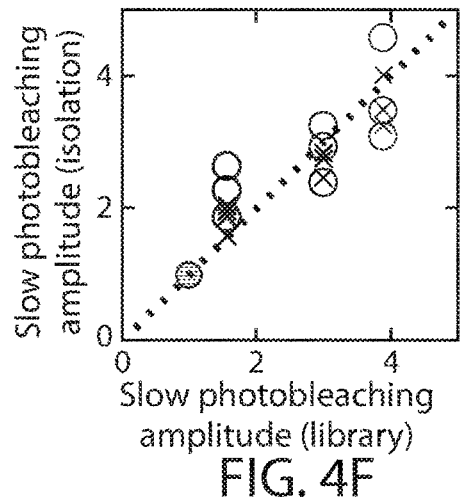
Figure 4E:
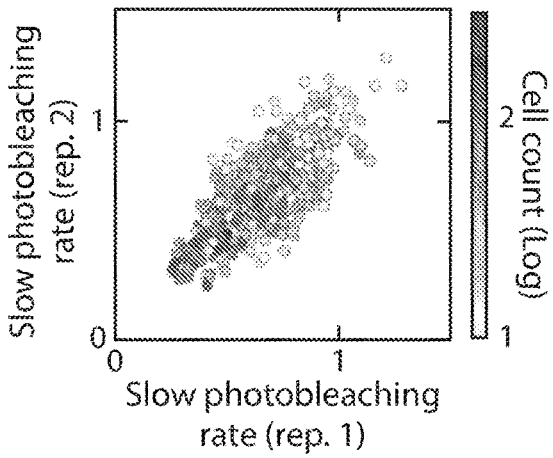
Figure 6A:
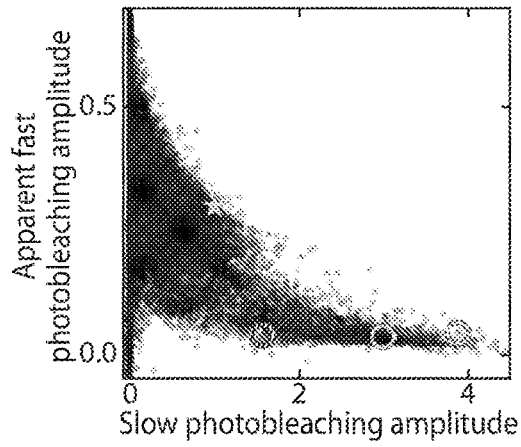
FIGS. 6A-6F illustrate additional screening of cells, in yet another embodiment of the invention.
Figure 6B:
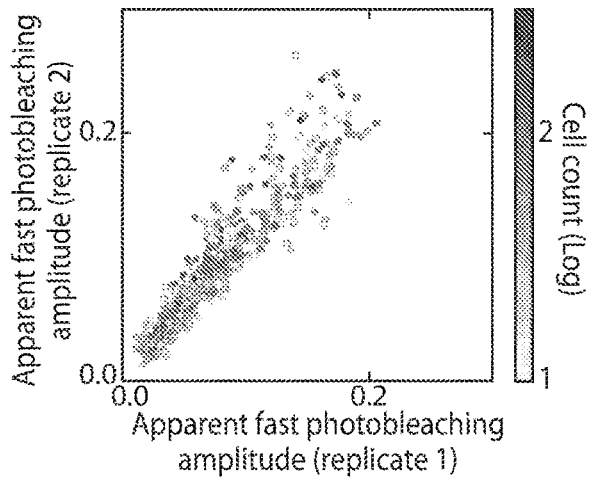
Figure 6C:
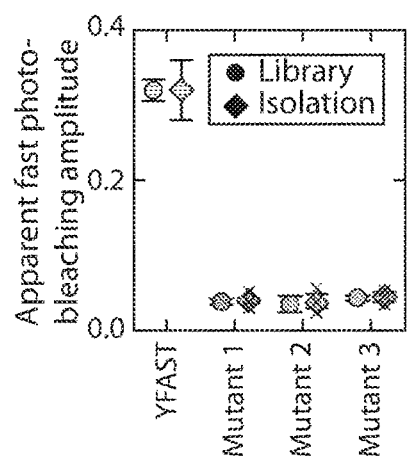
Figure 6D:
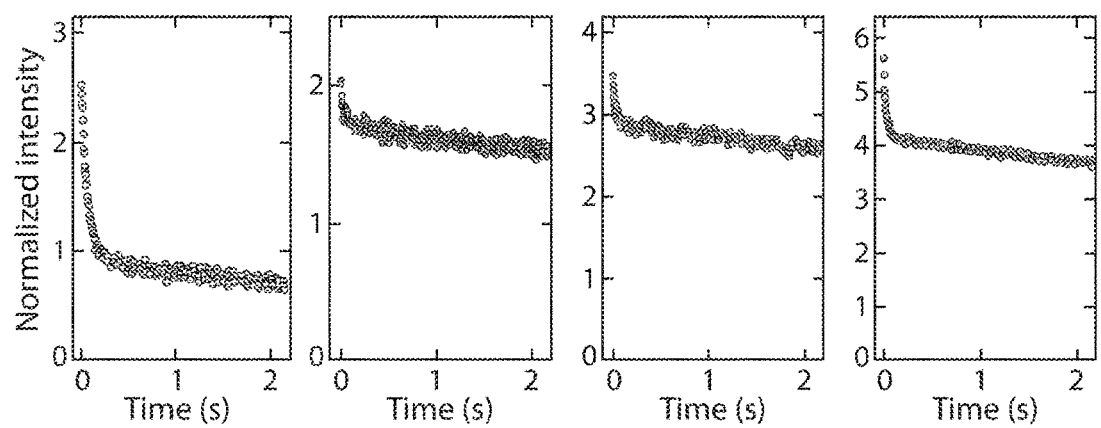
Figure 6E:
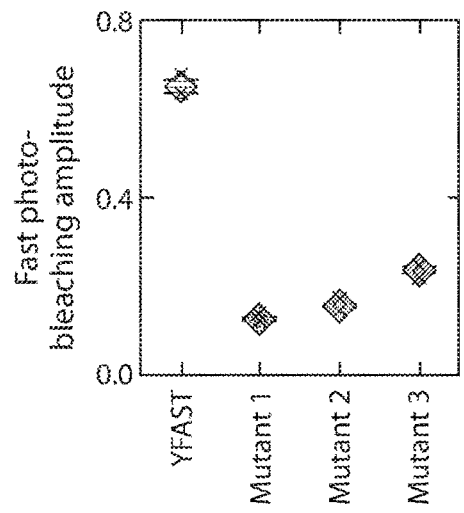
Figure 6F:
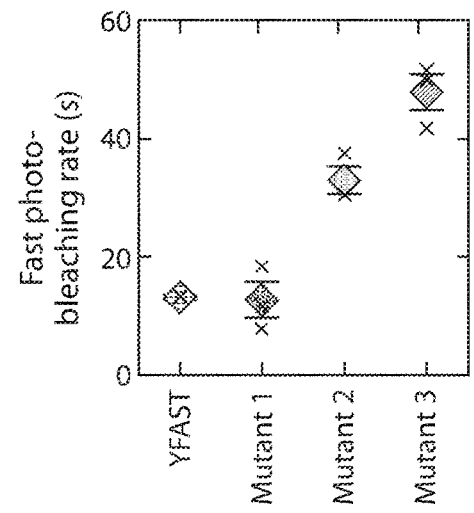

After measuring the phenotype of the YFAST variants, the cells were methanol fixed and the barcodes were measured as described above. The cells were grouped based on the measured YFAST mutant genotype and the median slow photobleaching amplitude, slow photobleaching rate, and relative fast photobleaching amplitude were calculated for each mutant (FIG. 4C and FIG. 6A). Altogether, ~20 million cells containing ~60,000 YFAST variants and ~160,000 barcodes were screened. A subset of the library measurements was replicated and the measured parameters were reproduced (FIG. 4D, FIG. 4E, and FIG. 6B).

Figure 4G:
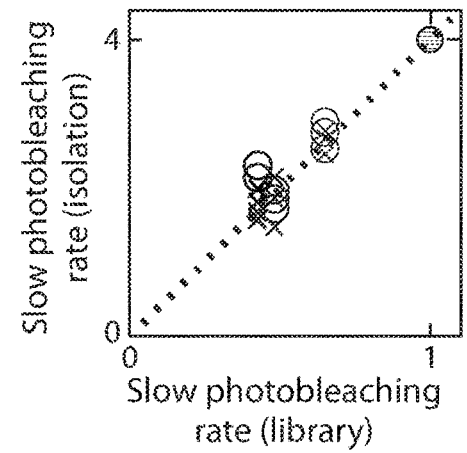

To further test the accuracy of the screen, three brighter and more photostable mutants were selected and characterized in homogeneous cultures where all bacteria express one of the selected mutants. As demonstrated by such measurements, these mutants were substantially brighter and more photostable than the original YFAST protein (FIG. 4F and FIG. 4G). Additionally, these isolated mutants were measured with higher temporal resolution to demonstrate that the magnitude and the rate of the fast photobleaching component are consistent with a decreased relative fast photobleaching amplitude measured in the screen with a lower temporal resolution (FIG. 6C, FIG. 6D, FIG. 6E, and FIG. 6F).

FIG. 4 shows screening YFAST mutant libraries for decreased slow-photobleaching rate and increased brightness. FIG. 4A shows a schematic diagram of YFAST library design. YFAST is dark on its own, but it becomes fluorescent upon binding to the ligand, HMBR. A library of YFAST variants fused to mTagBFP2 for normalization was merged with a library of barcodes and transformed into E. coli cells. FIG. 4B shows the phenotype measurement for two cells containing two variants of the YFAST protein. The fluorescence decay curve of the original YFAST (bottom curve) and a YFAST variant (top curve) was measured by illumination with 488 nm light to excite YFAST only. From each of these curves, the slow photobleaching rate, slow photobleaching amplitude, and fractional fast photobleaching rate were determined by fitting the curve with a double exponential decay. FIG. 4C shows a scatter plot of the slow photobleaching rate and the slow photobleaching amplitude for each mutant in the library. Library measurements of the original YFAST and three mutants are indicated by the star and open circles. FIG. 4D and FIG. 4E show the amplitudes (FIG. 4D) and rate constants (FIG. 4E) of the slow photobleaching component for two replicate measurements. Each filled circle in FIG. 4C-E depicts the median rate constants and amplitude of all cells associated with one mutant, and only mutants containing at least ten imaged cells are depicted. FIG. 4F and FIG. 4G show the amplitudes (FIG. 4F) and rate constants (FIG. 4G) of the slow photobleaching component of three selected mutants measured in isolation versus those measured in the library screen. Each point corresponds with a replicate of the isolation measurements conducted at the library-screen time resolution (120 ms; crosses) or at a 4-ms time resolution (circles). Amplitudes and rates are normalized to those of the original YFAST.

FIG. 5 shows the reversible and biphasic photobleaching kinetics of YFAST. The normalized fluorescence intensity (crosses) upon intermittent illumination with 488-nm light and a fit to a double exponential decay (solid line). $E.$ $coli$ expressing mTagBFP2-YFAST were adhered to a glass coverslip, immersed in 10 micromolar HMBR in PBS and imaged at 4-ms time resolution. The YFAST fluorescence intensity for each cell is normalized by the mTagBFP2 fluorescence and averaged over multiple cells in the imaged area. The 488-nm illumination was switched on and off with a period of 2 seconds. Intensity values of zero represent the period of time when the illumination was off.

FIG. 6 shows quantifications of the fast photobleaching amplitude from the same library measurements as FIG. 4. FIG. 6A depicts a scatter plot of apparent fast photobleaching amplitude and slow photobleaching amplitude for each mutant in the library. Library measurements of the original YFAST and three mutants are indicated by the star and open circles. FIG. 6B shows the apparent fast photobleaching amplitude for two replicate library measurements. Each filled circle in FIGS. 6A and B depicts the amplitude of all cells associated with one mutant, and only mutants containing at least ten imaged cells are depicted. FIG. 6C shows the apparent fast photobleaching amplitude of three selected mutants from the library screen and their corresponding values measured in isolation with the same time resolution as the library measurements. FIG. 6D shows the fluorescence decay of the original YFAST and three select mutants measured at a 4-ms time resolution. The depicted mutants correspond to the open circles in FIG. 6A. FIGS. 6E and F depict fractional photobleaching amplitude (FIG. 6E) and photobleaching rate (FIG. 6F) of the fast photobleaching component for the original YFAST and the selected mutants characterized in isolation measurements at a 4-ms time resolution.

In summary, these examples show methods for image-based screening of large genetic variant libraries by co-expressing the genetic variants and barcode that can identify these genetic variants in cells, and determining both the phenotypes of the genetic variants and the barcodes in the same cells using imaging. By reading out barcodes using massively multiplexed FISH, the ability to screen hundreds of thousands of barcodes that correspond to tens of thousands of unique genetic variations was shown. Using these techniques, mutations in the YFAST protein, a recently discovered ligand-dependent fluorescent protein with substantially improved brightness and photostability, were demonstrated in this example.

Example 4

Following are materials and methods used in some of the above examples.

Barcode library assembly. The barcode library used a set of plasmids, each containing a DNA barcode sequence that encodes a RNA designed to represent a single N-bit binary word. Every barcode in the library had N readout sequences, one corresponding to each bit, designed to be read out by hybridizing fluorescent probes with the complementary sequence. For each bit position, one 20-mer sequence was assigned to encode a value of "0" and another 20-mer sequence to encode a value of "1". To increase the rate of hybridization, these encoding sequences were constructed from a three-letter nucleotide alphabet, one with only A, T, and C, in order to destabilize potential secondary structures. The utilized sequences were drawn from those previously used for MERFISH with additional sequences designed using approaches described previously. For each barcode, the bits were concatenated with a single G separating each. Although bits are present in the barcode set that was constructed here, to reduce the number of hybridization rounds, experiments were conducted by reading out either 21 or 18 of the possible bits, depending on the library size.

Figure 7:
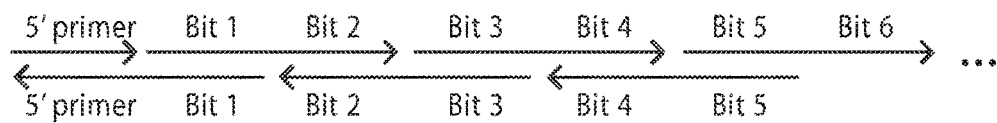
FIG. 7 illustrates the structure of a nucleic acid containing bits, in still another embodiment of the invention.

This barcode library was assembled by ligating a mixture of short, overlapping oligonucleotides, each representing a pair of adjacent bits (FIG. 7). For each pair of adjacent bits, there were four unique combinations of bit values ("00", "01", "10", and "11"). Each corresponding sequence was synthesized as a single-stranded oligonucleotide. The oligonucleotides were then ligated to form complete, double-stranded barcodes that contain concatenated sequences of all bits with all possible bit values. For the ligation step, all oligonucleotides were mixed and diluted so that each oligo was present at a concentration of 100 nM. The mixture was phosphorylated by incubating with T4 polynucleotide kinase (16 microliter oligonucleotide mixture, 2 microliter T4 ligase buffer, 2 microliter PNK [NEB, M0201S]) at 37° C. for 30 minutes and ligated by adding 1 microliter T4 ligase (NEB, M0202S), and incubating for 1 hour at room temperature.

To prepare a plasmid library containing these barcode sequences under the control of the 1pp promoter, the ligation product was diluted 10-fold and amplified by limited-cycle PCR on a Bio-Rad CFX96 using Phusion polymerase (NEB, M0531S0) and EvaGreen (Biotium, 3100). The PCR product was run in an agarose gel, and the band of the expected length was extracted and purified (Zymo Zymoclean Gel DNA Recovery Kit, D4002). The purified product was inserted by isothermal assembly for 1 hour at 50° C. (NEB NEBuilder HiFi DNA Assembly Master Mix, E2621L) into a plasmid backbone fragment containing the colE1 origin, the ampicillin resistance gene, and other elements taken from the pZ series of plasmids. The assembled plasmids were purified (Zymo DNA Clean and Concentration, D4003), eluted into 6 microliter water, mixed with 10 microliter of electro-competent $E.$ $coli$ on ice (NEB, C2986K), and electroporated using an Amaxa Nucleofector II. Immediately after electroporation, 1 mL SOC was added and the culture was incubated at 37° C. on a shaker for one hour. Subsequently, the SOC culture was diluted into 50 mL of LB (Teknova, L8000) supplemented with 0.1 mg/mL carbenicillin (ThermoFisher, 10177-012) and placed on the shaker at 37° C. overnight. The following day, the culture was miniprepped (Zymo Zyppy Plasmid Miniprep Kit, D4019), yielding the complete barcode library.

Assembling protein mutant libraries. To create a library of mutant proteins, short nucleotide sequences containing regions of the protein with the desired mutations were synthesized as complex oligonucleotide pools. To then create the desired mutant genes from these pools, the pool and its corresponding expression plasmid was amplified via limited cycle PCR and these fragments assembled using isothermal assembly. The expression backbone was derived from the colE1 origin and the chloramphenicol resistance gene from the pZ series of plasmids. Oligonucleotide pool synthesis may be prone to deletions, which could lead to frameshift mutations that produce non-viable proteins. To remove these variants prior to measurement, the protein variants were translationally fused upstream to the chloramphenicol resistance protein. These constructs were electroporated into E. coli, as described above, and these cultures grown in the presence of chloramphenicol to select only for protein variants that did not have frame-shift mutations and which could, thus, translate competent chloramphenicol resistance. These plasmids were re-isolated via plasmid miniprep and the genetic variants extracted via PCR prior to combination with the barcode library.

Merging mutation libraries with the barcode library. To merge a mutant library with the barcode library, the corresponding halves of each plasmid library were amplified by limited-cycle PCR. Of note, the forward primer for amplifying the barcode library contained 20 random nucleotides so that each assembled plasmid contained a 20-mer unique molecular identifier (UMI). Also, the protein mutant half contained the plasmid's replication origin (colE1) while the barcode half contained the ampicillin resistance gene ensuring that only plasmids containing both halves were competent. The two halves were assembled by isothermal assembly and transfected into electrocompetent E. coli as described earlier. After incubating in SOC for 1 hour at 37° C., the culture was again diluted into 50 mL LB and grown until it reached an optical density at 600 nm (OD600) of ~1. To limit the possibility that a single bacterium had taken up more than one plasmid, plasmids were extracted again from this culture and reinserted at a concentration where the number of E. coli cells significantly outnumbered the number of plasmids. Specifically, 2 microliter of the plasmid library at 100 pg/microliter was re-electroporated into 10 microliter of fresh electro-competent E. coli. This culture was then grown and diluted to a concentration of ~1000 cells/microliter by using the OD600 to determine the number of cells in the culture and, thus, the appropriate dilution. From the diluted culture, a volume containing the desired number of cells, and hence the desired number of unique barcode-mutant pairs, was inoculated into a new culture. This culture was incubated at 37° C. overnight and the following day it was archived for future imaging experiments by diluting 1:1 in 50% glycerol (Teknova, G1796), separating into 100 microliter aliquots, and storing at −80° C. The remaining culture was mini-prepped to use as a PCR template for constructing the barcode to genotype lookup table.

Constructing the barcode-to-genotype lookup table. Since barcodes and gene variants were assembled randomly, next generation sequencing was used to construct a look-up table that links barcodes to their corresponding gene variant. The total length of the combined sequence of the gene variant and the barcode exceeded the read length of the sequencing platform used (Illumina MiSeq). To circumvent this challenge, multiple fragments were extracted from each library, sequenced independently and grouped computationally using the UMI.

The mini-prepped libraries were prepared for sequencing by two sequential limited-cycle PCRs. The first PCR extracted the desired region while adding the sequencing priming regions, and the second PCR added multiplexing indices and the Illumina adapter sequences. Between PCRs, the product was purified in an agarose gel and the final product was gel purified prior to sequencing.

For each sequencing read, the corresponding barcode or gene variant sequence was extracted. The reads were then grouped by common UMI, and the most frequently occurring barcode and gene variant seen for each UMI was assigned to that UMI, constructing the barcode-to-gene variant lookup table for every variant in the library. Any ambiguous barcode (i.e. a barcode assigned to more than one genetic variant) was excluded from further analysis. This analysis was conducted in custom software written in Matlab.

Library design of YFAST variants. Since YFAST is a recently developed fluorescent protein, the consequences of mutating different regions of the protein are not well characterized in the literature. Hence, the screen in this example was started by concurrently designing libraries following two distinct strategies. In the first strategy, a structurally naive view was used and a library was constructed (library type 1, LT1) having mutants corresponding to all possible single amino acid substitutions, insertions, and deletions at each location within YFAST. The second strategy made use of structural information of the YFAST precursor, Photoactive Yellow Protein (PYP) (PDB: 1NWZ) to target residues adjacent to the chromophore (library type 2, LT2-1), introducing up to 6 amino-acid substitutions per mutant. These libraries were screened using this screening method. Since many of the mutants in LT2-1 appeared dark, the selection of mutations was refined by redesigning the oligonucleotide pool to only include those amino-acid substitutions that appeared bright with relatively high frequencies in the LT2-1 library and another library (LT2-2) was created that combined these substitutions, containing up to 6 substitutions per mutant. This library was screened with this method as well. A library (library type 3, LT3) was created by combining mutations found to have favorable brightness and photostability (i.e. relatively large amplitude of the slow bleaching component) in LT1 with those mutations found to have favorable brightness and photostability in all LT2. Each variant in LT3 contains up to 10 mutations. LT3 was screened and a mutant with 6 amino acid substitutions that is particularly photostable with a large amplitude of the slow bleaching component and nearly eliminated the fast component at the library measurement time resolution was identified. Next, to further improve the fluorescent properties of this mutant, a new library (library type 4, LT4) that contained all possible single amino acid substitution, insertion, and deletion at every residue of this mutant was created. Finally, based on the screening results of LT4, library type 5 (LT5) was created by splitting the entire protein sequence into 6 regions, selecting LT4 mutations with favorable brightness and photostability in each region, and creating all possible combinations of these mutations. LT5 contains 6-12 mutations per library member.

Some of the above libraries were constructed and measured concurrently while developing and optimizing the screening protocol. Therefore, all of the libraries were re-measured again, by mixing them into pools containing ~25,000 barcodes each. Instead of combining all libraries into a single pool and measuring a very large number of cells in a single screen over a long time, the measurements were split into smaller pools and measured at 1-2 million cells per experiment. Since the phenotype accuracy increases with the number of cells measured, the results from the earlier measurements of individual libraries that were performed using the optimized protocol were also included. FIG. 4 and FIG. 6 contain results from all library measurements performed with the optimized protocol.

Phenotype and barcode imaging. Each library was prepared for imaging by thawing the 100 microliter aliquot from −80° C. to room temperature and diluting into 2 mL LB supplemented with 0.1 mg/mL carbenicillin. Imaging coverslips (Bioptechs, 0420-0323-2) in 60-mm-diameter cell culture dishes were prepared by covering them in 1% polyethylenimine (Sigma-Aldrich, P3143-500ML) in water for 30 minutes followed by a single wash with phosphate buffered saline (PBS). The E. coli culture was diluted 10-fold into PBS, poured into the culture dish, and spun at 100 g for 5 minutes to adhere cells to the surface.

The sample coverslip was assembled into a Bioptech's FCS2 flow chamber. A peristaltic pump (Gilson, MINIPULS 3) pulled liquid through the chamber while three computer-controlled valves (Hamilton, MVP and HVXM 8-5) were used to select the input fluid. The sample was imaged on a custom microscope built around a Nikon Ti-U microscope body with a Nikon CFI Plan Apo Lambda 60× oil immersion objective with 1.4 NA. Illumination was provided at 405, 488, 560, 647, and 750 nm using solid-state single-mode lasers (Coherent, Obis 405 nm LX 200 mW; Coherent, Genesis MX488-1000; MPB Communications, 2RU-VFL-P-2000-560-B1R, MPB Communication, 2RU-VFL-P-1500-647-B1R; and MPB Communications, 2RU-VFL-P-500-750-B1R) in addition to the overhead halogen lamp for bright field illumination. The Gaussian profile from the lasers was transformed into a top-hat profile using a refractive beam shaper (Newport, GBS-AR14). The intensity of the 488-, 560-, and 647-nm lasers was controlled by an acousto-optic tunable-filter (AOTF), the 405-nm laser was modulated by a direct digital signal, and the 750-nm laser and overhead lamp were switched by mechanical shutters. The excitation illumination was separated from the emission using a custom dichroic (Chroma, zy405/488/561/647/752RP-UF1) and emission filter (Chroma, ZET405/488/461/647-656/752m). The emission was imaged onto an Andor iXon+888 EMCCD camera. During acquisition, the sample was translated using a motorized XY stage (Ludl, BioPrecision2) and kept in focus using a home-built auto-focus system.

Phenotype measurements were conducted immediately after cells were deposited onto the coverslip, inserted into the flow chamber, and immersed in PBS. For imaging E. coli cells expressing mMaple3-mTagBFP2 fusion or mTagBFP2 alone, an image was first acquired for 1 frame with 405-nm illumination to excite mTagBFP2 at a frame rate of 8.4 Hz (120 ms), followed by illumination with 405-nm light for 30 additional frames at 8.4 Hz to photoactivate mMaple3. Then an image was acquired with 560-nm illumination for 1 frame to detect mMaple3 fluorescence. For imaging E. coli cells expressing the YFAST mutants, images were first acquired in the absence of the chromophore with 405-nm illumination for 1 frame to measure the mTagBFP2 fluorescence to determine the position of each cell followed by an image with bright-field illumination for alignment between multiple imaging rounds. Then 10 micromolar of the chromophore HMBR in PBS was flowed over the cells and a fluorescence image was acquired with 488-nm illumination for 1 frame to measure YFAST intensity, 405-nm illumination for 1 frame to measure mTagBFP2 intensity, and a bright-field image was acquired again for alignment, followed by at least 20 frames at 8.4 Hz with constant 488-nm illumination to measure the decrease in intensity upon photobleaching. Since 8.4 Hz is the full field frame rate of the camera that was used, increasing the time resolution would require imaging a smaller field of view per frame and hence a reduction in the measurement throughput. Images were acquired at thousands of locations in the sample, each corresponding to a ~200×200 micrometer$^2$ field-of-view. All fields were imaged prior to the addition of the chromophore to determine the position of each cell, and then after the chromophore was added, all of the subsequent exposure sequence described above was completed at each field prior to moving to the next. The illumination intensities at the back-focal plane used in these experiments were 1 W/cm$^2$, 3 W/cm$^2$, and 10 W/cm$^2$ for the 405-nm, 488-nm, and 561-nm lasers, respectively. Following the phenotype measurement, the cells were fixed by incubation for 30 minutes in a mixture of methanol and acetone at a 4:1 ratio for fast hybridization to RNA. To prevent salts from precipitating and clogging the flow system, water was flowed before and after the fixation mixture. Once fixed, the cells were washed in 2× Saline Sodium Chloride (SSC) and hybridizations for MERFISH imaging were started.

To determine the RNA barcode expressed within each cell, multiple rounds of hybridizations were performed. For each hybridization round, the sample was incubated for 30 minutes in hybridization buffer (2×SSC; 5% w/v dextran sulfate (EMD Millipore, 3730-100ML), 5% w/v ethylene carbonate (Sigma-Aldrich, E26258-500G), 0.05% w/v yeast tRNA, and 0.1% v/v Murine RNase inhibitor (NEB, M0314L)) with a mixture of readout probes labeled with either ATTO565, Cy5, or Alexa750 (Bio-Synthesis Inc.) each at a concentration of 10 nM). In the readout probes, the dyes were linked to the oligonucleotides through a disulfide bond. Then, the hybridization buffer was replaced by an oxygen-scavenging buffer for imaging (2×SSC; 50 mM TrisHCl pH 8, 10% w/v glucose (Sigma-Aldrich, G8270), 2 mM Trolox (Sigma-Aldrich, 238813), 0.5 mg/mL glucose oxidase (Sigma-Aldrich, G2133), and 40 µg/mL catalase (Sigma-Aldrich, C100-500 mg)). Each position in the flow cell was imaged with 750-, 647-, and 560-nm illumination from longest to shortest wavelength followed by bright-field illumination for alignment before continuing to the next location. Following the imaging of all regions, the disulfide bonds linking the dyes to the oligonucleotides in the readout probes were cleaved by incubating the sample in 50 mM tris (2-carboxyethyl)phosphine (TCEP; Sigma-Aldrich, 646547-10X1ML) in 2×SSC for 15 minutes. The sample was then rinsed in 2×SSC and the next hybridization round started. For each round of hybridization, three readout probes with spectrally discernable dyes (ATTO565, Cy5, and Alexa750) were hybridized simultaneously as described above. Altogether, with 14 hybridization rounds, all 42 readouts corresponding to 21 bits were measured in 40 hours. For smaller libraries, the imaging area was reduced, and the number of hybridization rounds was decreased to 12 (for 18-bit readout), reducing the measurement time to 22 hours.

Image analysis. To correct for residual illumination variations across the camera, a flat-field correction was performed as follows. Every image was divided by the mean intensity image for all images with the given illumination color. Then, the images for different rounds corresponding to the same region were aligned using the image acquired under bright field illumination by up-sampled cross-correlation, creating a normalized image stack of all images at each position in the flow chamber. If the radial power spectral density of any given bright field image did not contain sufficient high frequency power, the image was designated as out-of-focus and all images for the corresponding region were excluded from further analysis.

To extract cell intensities, the edges of each cell were detected using the Canny edge detection algorithm on the image acquired with 405-nm illumination for mTagBFP2 imaging. The edges that formed closed boundaries were filled in and closed regions of pixels were extracted. If a given closed pixel region had a filled area of more than 20 pixels and the ratio of the filled area to the area of the convex hull was greater than 0.9, it was classified as a cell. To increase the cell detection efficiency, the detected cells were then removed from the binary image, the image was dilated, filled, and eroded and cells were extracted again. This allowed cells where gaps exist in the detected edges to still be detected. For each cell, the mean intensity was extracted for the corresponding pixels in every image.

From the cell intensities, the phenotypes and barcodes were calculated. For each measured readout sequence, the measured intensity was normalized by subtracting the minimum and dividing by the median signal observed for that readout sequence across all cells. To determine whether a barcode contained a "1" or a "0" at each bit, the measured intensities of the "1" readout sequence and the "0" readout sequence for that bit were compared. Specifically, a threshold was selected on the ratio of these two values, called the "0"-to-"1" intensity ratio. If the "0"-to-"1" intensity ratio was above the threshold, the bit was called as a "0". Otherwise, the bit was called as a "1". Because the "1" and "0" readout sequences were measured in different hybridization rounds and there was variation in staining quality between rounds, this threshold was optimized for each bit individually. This optimization was performed by randomly selecting 150 barcodes (a training set) from the set of known barcodes that were determined to be present in the library by sequencing. An initial set of thresholds was selected and the fraction of cells matching these barcodes was determined. The threshold for each bit was then varied independently to identify the threshold set that maximizes this fraction. This optimized threshold set was then used for determining the bit values for all cells.

Once the barcode was determined for each cell, cells were grouped by barcode and the median of the various phenotype values was computed to determine the measured phenotype for the genotype corresponding to that barcode. For the mMaple3 measurement, the normalized brightness was determined from the ratio of the mMaple3 intensity under 560-nm illumination to the mTagBFP2 intensity under 405-nm illumination, as discussed above. For YFAST measurements, the normalized intensity was determined by the ratio of the YFAST fluorescence intensities under 488-nm illumination in the presence of the YFAST chromophore HMBR to the mTagBFP2 fluorescence intensities under 405-nm illumination. To account for the fluorescence background present in *E. coli* upon 488-nm illumination, the background was independently determined and subtracted before calculating the fluorescence ratio. The background was estimated by calculating the median intensity of all cells upon 488-nm illumination predicted to contain a non-fluorescent YFAST mutant. Specifically, cells, grouped by barcode, were assigned to the non-fluorescent population if the Pearson correlation coefficient between the fluorescence intensity measured under 488-nm illumination (YFAST channel) and those measured under 405-nm illumination (mTagBFP2 channel) for the grouped cells fell below a threshold of 0.2. Since the YFAST variant is translationally fused to mTagBFP2, when the two intensities are uncorrelated, it suggests that the number of YFAST proteins in the cells does not affect the brightness of the cell and hence the YFAST associated with that barcode should be dark.

The initial high-time resolution (4-ms) measurements of the original YFAST variant revealed a biphasic decay of fluorescence with time. To quantify this behavior, the background-subtracted photobleaching curve, b(t), was fit to the sum of two exponentials:

$$b(t) = p_{fast} e^{-At} + p_{slow} e^{-Bt}$$

where $p_{fast}$ and A represent the amplitude and decay rate constant for the fast photobleaching component and $p_{slow}$ and B represent the corresponding values for the slow photobleaching component. These fits of the original YFAST showed that the decay rate constants for the fast and slow components were ~10 s-1 and ~0.1 s-1, respectively, under this illumination intensity.

This double-exponential decay function was also used to characterize the library screen measurements. However, to increase the throughput of the screens, the full imaging frame of the camera was utilized, which required the use of a slower frame rate (8.4 Hz, ~120 ms). This frame rate was comparable to the decay rate observed for the fast component of the original YFAST variant; thus, it was not anticipated that the rate constant associated with the fast component would be well constrained by this double-exponential fit. To address this, the rate constant of the fast component was initially fixed to the value determined from the original YFAST and the other three parameters allowed to vary in the fit. The time resolution of the library measurements was much higher than the decay time constant of the slow component; thus, the parameters associated with the slow component, $p_{slow}$ and B, were well constrained by this fit—a point confirmed by the observation that $p_{slow}$ and B did not change appreciably (by <0.5%) when the fixed value of A was varied over a wide range, or A was also used as a fitting parameter. Furthermore, it was anticipated that the time resolution, 120 ms, and duration, 2.5 s, of the library measurements, plus the independent determination of the background level (discussed above), should allow $p_{slow}$ and B to be determined reliably. Though there was a possibility that beyond the measurement duration, YFAST displays more complicated photobleaching kinetics with more decay rate constants, in which case, the reported rate constant B for the slow component should be considered the initial decay rate of this component. To estimate the fast component amplitude, $p_{fast}$, the well-constrained value of the slow component amplitude, $p_{slow}$, was utilized. Specifically, $p_{fast}$ was calculated from the difference of the initial brightness of each variant ($p_{fast} + p_{slow}$) and the fit value for the slow component amplitude, $p_{slow}$. Because of the limited time resolution of the library screen, the rate constant of the fast bleaching component was not extracted. It was noted that the apparent amplitude that was determined for the fast bleaching component may systematically underestimate this amplitude. Nonetheless, it should still provide useful information for future imaging experiments using the YFAST variants at ~100 ms or slower time resolution.

The reported values for the slow component amplitude and decay rate were normalized to the corresponding values measured for the original YFAST, unless otherwise mentioned. The fast photobleaching component amplitude was not normalized in this fashion but rather was reported as the fraction of the total brightness, which was termed the fractional fast photobleaching amplitude.

This analysis was conducted in custom software written in Python.

Example 5

Considerations when designing a high-throughput screen. There are several aspects that should be taken into account when designing a high-throughput screen, including, for example, the number of bits in the barcodes, the fraction of possible barcodes used, and the number of cells that should be measured per variant to allow phenotypes to be measured accurately. This example summarizes some points that may be considered when designing a screen to measure the phenotypic variability within a given library.

Bottlenecking barcodes. In these examples, only a small fraction of all possible N-bit binary barcodes were used in a library, and this bottlenecking strategy served two purposes: (i) to limit the frequency with which the same barcode might be associated with two or more different genetic variants and (ii) to introduce an error robustness into this barcode-to-genotype identification process. In the construction of the barcoded genetic variants, barcodes were associated with individual genetic variants randomly, hence the probability that a given barcode could be assigned to multiple different genetic variant could be high. While this situation may be detected via next-generation sequencing when the barcode-to-genetic variant lookup table is built, these barcodes may also need to be discarded from the library screen measurement since cells containing such barcodes could not be unambiguously assigned to a given genotype. If a large fraction of the used barcodes were associated with multiple genetic variants, the number of barcodes that would need to be discarded would be high. To overcome this, the number of barcodes used in the library discussed above was restricted to be less than 10% of the total number of possible N-bit binary barcodes. Specifically, after the barcoded genetic variants were assembled, the size of the barcoded genetic variants library was bottlenecked such that the number of genetic variant-barcode pairs in the library was <10% of the total number of possible N-bit binary barcodes. Because only such a small fraction of barcodes are included, most barcodes would be present only once in the library, and the chance that a barcode was present more than once (hence allowing the possibility of being paired with more than one genetic variant) was very small (<10%). The remaining small fraction of barcodes that were paired with more than one variant could be detected by sequencing and discarded in further analysis.

The second reason why bottlenecking was used was to introduce error robustness into the genotype identification process. Specifically, if only a relatively small fraction of all possible barcodes was used, barcode measurement errors would more likely produce a barcode that is not present in the library, i.e. an invalid barcode. Because the exact barcodes that are present in the library via next-generation sequencing are known, it is possible to identify the invalid barcodes that resulted from errors during barcode imaging and discard them. This ability greatly reduced the rate at which the genotype of a given cell was misidentified. For example, if the barcode number was bottlenecked such that <10% of the total possible barcodes are present in the library, the chance that a barcode imaging error would lead to genotype misidentification will be reduced to <10%.

In the above experiments, a degree of bottlenecking was chosen such that only 1-10% of the possible 21-bit binary barcodes was present in the libraries. The bottlenecking was achieved experimentally by selecting a small, random subset of cells after transforming *E. coli* cells with the barcode-mutant plasmids under the condition that each cell contains a unique barcode-mutant pair. For example, to achieve a bottlenecking degree of 4%, the number of cells that is 4% of the number of possible 21-bit binary barcodes was selected.

Determining the number bits in the barcodes. The number of bits in the barcode was determined by the number of gene variants that was needed to screen. While optimizing YFAST, mutant libraries were created in two ways: (1) The first type of libraries contained a defined, relatively small number of mutants that was hoped to be screened exhaustively; (2) the second type of libraries contained a very large number of possible mutants where screening only a random subset of these mutants would already be very informative. When the first type of libraries was created, a barcode diversity was chosen such that the number of barcodes in the library was 5 times more than the number of unique mutants to ensure that each mutant (or at least the vast majority of them) was present in the library at least once. Because of the bottlenecking strategy describe above, namely the number of barcodes in the library being <10% of the total number of possible N-bit binary barcodes, the total number of possible barcodes needed to be 50 times more than the number of mutants to screen. Based on this number, the desired number of bits was determined. For example, if 20,000 specific mutants needed to be screened, more than 1 million possible barcodes would be needed, and hence a 21-bit barcoding scheme that can give ~2 million possible barcodes was used. When the second type of libraries was created in which only a subset of possible mutants will be screened, a library size was selected to be equal to the number of mutants that was intended to subsample from the larger library; in this case, each mutant in the library was only associated with a single barcode and the number of barcodes in the library was equal to the number of mutants to be screened. The number of possible N-bit binary barcodes and hence the number of bits required were then likewise determined based on the bottlenecking strategy.

Determining the desired number of measured cells per genetic variant. In the library screens, the number of cells that need to be measured for each genetic variant was largely determined by the accuracy of the phenotype measurement. As the number of cells measured for each genotype increases, the accuracy with which that phenotype is measured improves. The desired cell number per genetic variant was set by the noise properties of the screened phenotype and the measurement accuracy that is needed to discriminate phenotype variations.

For the screen of YFAST variants, a large cell-to-cell variance in the fluorescence intensity measurements was observed between cells expressing the same genotype. This variance was observed even within a monoculture of the original YFAST. This observation indicated that the measurement accuracy of this type of phenotype from a single cell was low and, thus, required screening many more cells than mutants to increase this accuracy. In addition, it was found that different mutants appear in different abundance within the libraries, and this natural variation arose because of the random processes of constructing the plasmid-mutant libraries and transforming *E. coli*. To ensure that the majority of mutants were measured with a desired number of cells, this abundance variation further increased the oversampling requirement. For the YFAST measurements, ~100 cells on average per mutant were measured.

Finally, in the genotype (barcode) measurements, a substantial fraction of the cells were discarded by readout intensity thresholding and by the rejection of barcodes that do not match the valid barcodes present in the library, as described above. In the above measurements, ~66% of the measured cells were discarded because of the above procedures. As a result, on average, 300 cells per YFAST variant needed to be measured to achieve of the goal of ~100 cells per mutant. Therefore, 20 million cells were measured to screen 60,000 YFAST variants in these experiments.

Since the noise properties of the screened phenotype and the measurement accuracy that was needed to discriminate phenotype variations both depend on the phenotype to be screened, the number of cells that needs to be measured per genotype depended on the phenotype to be screened. It is worth noting that given the reproducibility between phenotypes measured for the same genotype in separate screens, it may also be possible to increase the number of cells measured on average for a given library by simply replicating the screen multiple times with the same library and pooling the results so as to improve the accuracy of phenotype variability if it is determined not to be sufficient from a single measurement, in certain embodiments.

Estimate of the maximum plausible library size of the genetic variants. There are multiple factors that determine the maximum library size of genetic variants that can be screened. The first potential limitation to the size of the library is the number of unique barcodes that can be measured. These experiments demonstrated the ability to image 21-bit barcodes, and degradation in the image quality between the last imaged bit and the first imaged bit was not observed. Thus, adding more bits to the barcode should be possible. For example, 25-bit barcodes can also readily be measurable. Moreover, given such a modest extension in the length of the barcode, constructing plasmids that contain 25-bit barcodes (or other barcodes with 22 or more bits), or creating a barcode-mutant lookup table using existing next-generation sequencing approaches (Illumina HiSeq or NovaSeq). As a non-limiting example, 25-bits would produce ~30 million possible barcodes. Based on the bottlenecking strategy, <10% of the possible barcodes can be selected to include in the library, which means <3 million barcodes to include in the library. By utilizing high-competency E. coli strains, as shown here, 10-fold more transformants than library members can be created, a sufficient coverage level, by pooling a few transformation reactions. If the aim is to see each mutant (or the vast majority of them) at least once, 5 times more barcodes in the library than the number of genetic variants can be used, which, in this case, means the library could contain up to ~600,000 genetic variants. Assuming that 10-100 cells per variant were measured on average (depending on the phenotype measurement accuracy requirement), and based on the current settings of the barcode readout intensity threshold, in which ⅓ of cells pass the threshold and generate correct barcodes, ~18-180 million cells should be measured. In the measurements demonstrated here, ~1-2 million E. coli cells were characterized in a 40-hour long screen. However, in these measurements a relatively low density of E. coli on the coverslips were used, so as to minimize the chance of cells contacting each other. This density could be increased by at least 10-fold, e.g., without producing substantial cell-cell contact, and improvement in cell-segmentation algorithms should also allow contacting cells to be properly segmented. Thus, the density of cells is not a critical factor. Accordingly, measuring ~18-180 million cells with a reasonable imaging time (e.g., 2-18 days) is reasonable.

Moreover, there are multiple ways that the protocols could be modified so as to further increase throughput. For example, improved hybridization approaches can reduce the number of dim or dark cells, allowing more of the measured cells to be utilized in the screen. Lower magnification objectives can be used to measure much larger fields of view and hence allow substantial improvements in the measurement throughput. Low magnification for genotype (barcode) imaging while keeping the use of high magnification for the high-resolution phenotype measurements can be used in some embodiments, because the phenotype measurements are typically fast and the total imaging time of the screen is dominated by barcode imaging which requires many rounds of hybridization. In addition, the number of barcodes can be increased in some embodiments, for example, by either increasing the number of bits in the binary barcode scheme, and/or by using higher order barcoding schemes, such as ternary or quaternary schemes, etc.

Example 6

Following are some of the sequences used in the above examples.

```
Original YFAST, amino acid sequence:
                                        (SEQ ID NO: 1)
EHVAFGSEDIENTLAKMDDGQLDGLAFGAIQLDGDGNILQYNAAEGDITG

RDPKQVIGKNFFKDVAPGTDSPEFYGKFKEGVASGNLNTMFEWMPTSRGP

TKVKVHMKKALSGDSYWVFVKRV

Original YFAST, nucleotide sequence:
                                        (SEQ ID NO: 2)
GAACATGTGGCGTTTGGAAGTGAGGACATTGAGAATACGCTTGCGAAGAT

GGATGATGGTCAACTGGATGGTCTTGCCTTTGGAGCAATTCAGTTGGATG

GCGATGGTAACATCTTGCAGTACAATGCCGCCGAGGGTGATATTACAGGA

CGTGATCCCAAACAAGTGATTGGAAAAAATTTTTTCAAAGATGTAGCGCC

TGGCACTGACTCACCCGAGTTTTACGGTAAGTTCAAAGAAGGCGTGGCTT

CCGGTAATCTTAATACGATGTTTGAGTGGATGATCCCCACTAGCCGTGGA

CCCACCAAGGTGAAAGTGCATATGAAGAAGGCCTTATCGGGCGATAGCTA

CTGGGTGTTCGTTAAACGTGTT

Example improved YFAST, amino acid sequence:
                                        (SEQ ID NO: 3)
EHVAFGSEDIENTLAKMDDGQLDGLAFGAIQLDGDGNILQYNAAEGDITG

RDPKQVIGKNLFKDVACGTRSSEFYGKFKEGVASGNLNTMFEWMIPTSRG

PTKVKVHMKKALSGDSYWVFVKRV

Example improved YFAST, nucleotide sequence:
                                        (SEQ ID NO: 4)
GAACATGTGGCGTTTGGAAGTGAGGACATTGAGAATACGCTTGCGAAGAT

GGATGATGGTCAACTGGATGGTCTTGCCTTTGGAGCAATTCAGTTGGATG

GCGATGGTAACATCTTGCAGTACAATGCCGCCGAGGGTGATATTACAGGA

CGTGATCCCAAACAAGTGATTGGAAAAAATCTGTTCAAAGATGTAGCGTG

CGGCACTCGTTCAAGCGAGTTTTACGGTAAGTTCAAAGAAGGCGTGGCTT

CCGGTAATCTTAATACGATGTTTGAGTGGATGATCCCCACTAGCCGTGGA

CCCACCAAGGTGAAAGTGCATATGAAGAAGGCCTTATCGGGCGATAGCTA

CTGGGTGTTCGTTAAACGTGTT
``` mTagBFP2, amino acid sequence:
(SEQ ID NO: 5)
MVSKGEELIKENMHMKLYMEGTVDNHHFKCTSEGEGKPYEGTQTMRIKVV

EGGPLPFAFDILATSFLYGSKTFINHTQGIPDFFKQSFPEGFTWERVTTY

EDGGVLTATQDTSLQDGCLIYNVKIRGVNFTSNGPVMQKKTLGWEAFTET

LYPADGGLEGRNDMALKLVGGSHLIANAKTTYRSKKPAKNLKMPGVYYVD

YRLERIKEANNETYVEQHEVAVARYCDLPSKLGHKLN mTagBFP2, nucleotide sequence:
(SEQ ID NO: 6)
ATGGTGTCTAAAGGAGAGGAACTTATCAAAGAAAATATGCACATGAAGCT

TTACATGGAAGGAACAGTGGACAATCACCATTTTAAATGTACATCAGAAG

GCGAGGGTAAACCTTATGAGGGGACGCAAACCATGCGTATCAAGGTCGTA

GAGGGCGGCCCTTTGCCTTTCGCTTTCGACATTCTTGCAACCTCATTCTT

GTATGGCTCCAAGACTTTTATCAACCATACACAAGGCATTCCCGATTTCT

TTAAACAATCGTTCCCTGAAGGTTTTACATGGGAACGTGTAACAACATAT

GAAGATGGGGAGTTTTAACTGCCACACAGGATACATCTTTACAGGATGG

CTGCCTGATCTATAATGTAAAGATCCGTGGAGTGAACTTTACCTCGAACG

GCCCCGTCATGCAGAAAAAGACCCTTGGGTGGGAGGCCTTTACGGAAACG

CTTTACCCCGCGGACGGAGGTCTGGAAGGACGTAATGACATGGCGCTGAA

GCTTGTCGGAGGATCCCATCTGATCGCAAATGCTAAGACCACCTATCGTA

GCAAGAAACCTGCTAAAAACTTAAAAATGCCTGGTGTTTACTACGTGGAC

TATCGTCTTGAGCGTATTAAGGAGGCAAATAACGAAACCTATGTTGAACA

ACACGAGGTCGCTGTGGCCCGCTATTGCGACTTGCCCTCGAAGCTGGGGC

ATAAGTTGAAT mMaple3, amino acid sequence:
(SEQ ID NO: 7)
VSKGEETIMSVIKPDMKIKLRMEGNVNGHAFVIEGEGSGKPFEGIQTIDL

EVKEGAPLPFAYDILTTAFHYGNRVFTKYPRKIPDYFKQSFPEGYSWERS

MTYEDGGICNATNDITMEEDSFINKIHFKGTNFPPNGPVMQKRTVGWEVS

TEKMYVRDGVLKGDVKMKLLLKGGSHYRCDFRTTYKVKQKAVKLPKAHFV

DHRIEILSHDKDYNKVKLYEHAVARNSTDSMDELYK mMaple3, nucleotide sequence:
(SEQ ID NO: 8)
GTTAGCAAGGGCGAGGAGACCATCATGAGCGTGATCAAGCCGGACATGAA

GATCAAGCTGCGCATGGAGGGCAACGTGAACGGCCATGCCTTTGTGATCG

AGGGCGAGGGCAGCGGTAAGCCGTTTGAGGGCATCCAGACCATCGACCTG

GAGGTTAAGGAAGGCGCACCGCTGCCGTTTGCCTACGACATCCTGACCAC

CGCATTCCACTACGGCAACCGCGTGTTCACCAAGTACCCGCGCAAGATCC

CGGACTACTTCAAGCAGAGCTTCCCGGAGGGCTACAGTTGGGAACGCAGC

ATGACCTACGAGGACGGCGGTATCTGCAACGCCACCAACGACATCACCAT

GGAAGAAGATAGCTTCATCAACAAGATCCACTTCAAGGGCACAAACTTCC

CGCCGAATGGTCCGGTTATGCAGAAGCGCACCGTTGGCTGGGAGGTGAGC

ACCGAGAAGATGTATGCGCGACGGTGTGCTGAAGGGCGACGTGAAGAT

GAAGCTGCTGCTGAAGGGTGGCAGCCACTACCGCTGCGACTTCCGCACCA

CCTACAAAGTTAAGCAAAAGGCAGTGAAGTTACCGAAGGCCCACTTCGTG

GACCACCGCATCGAAATCCTGAGCCACGACAAGGACTATAACAAAGTGAA

GCTGTACGAGCACGCCGTGGCCCGTAACAGCACCGACAGCATGGATGAGC

TGTACAAA

Below explains a barcode library used in some of the above examples. The barcodes are 22 bits but only 21 of the bits were read out in the experiments described above. Each barcode has 22 readout sequences, one sequence corresponding to each bit. The 22 bit sequences used in the barcode library were:

Readout 1-1:
(SEQ ID NO: 9)
ATCCTCCTTCAATACATCCC

Readout 1-0:
(SEQ ID NO: 10)
TATCTCATCAATCCCACACT

Readout 2-1:
(SEQ ID NO: 11)
ACACTACCACCATTTCCTAT

Readout 2-0:
(SEQ ID NO: 12)
AAACACACACTAAACCACCC

Readout 3-1:
(SEQ ID NO: 13)
ACTCCACTACTACTCACTCT

Readout 3-0:
(SEQ ID NO: 14)
AACTCATCTCAATCCTCCCA

Readout 4-1:
(SEQ ID NO: 15)
ACCCTCTAACTTCCATCACA

Readout 4-0:
(SEQ ID NO: 16)
AATACTCTCCCACCTCAACT

Readout 5-1:
(SEQ ID NO: 17)
ACCACAACCCATTCCTTTCA

Readout 5-0:
(SEQ ID NO: 18)
TCTATCATCTCCAAACCACA

Readout 6-1:
(SEQ ID NO: 19)
TTTCTACCACTAATCAACCC

Readout 6-0:
(SEQ ID NO: 20)
TCCAACTCATCTCTAATCTC

Readout 7-1:
(SEQ ID NO: 21)
ACCCTTTACAAACACACCCT

Readout 7-0:
(SEQ ID NO: 22)
TTCCTAACAAATCACATCCC

Readout 8-1:
(SEQ ID NO: 23)
TCCTATTCTCAACCTAACCT

Readout 8-0:
(SEQ ID NO: 24)
ATAAATCATTCCCACTACCC

Readout 9-1:
(SEQ ID NO: 25)
TATCCTTCAATCCCTCCACA

Readout 9-0:
(SEQ ID NO: 26)
ACCCAACACTCATAACATCC

Readout 10-1:
(SEQ ID NO: 27)
ACATTACACCTCATTCTCCC

Readout 10-0:
(SEQ ID NO: 28)
TACTACAAACCCATAATCCC

Readout 11-1:
(SEQ ID NO: 29)
TTTACTCCCTACACCTCCAA

Readout 11-0:
(SEQ ID NO: 30)
ACTTTCCACATACTATCCCA

Readout 12-1:
(SEQ ID NO: 31)
TTCTCCCTCTATCAACTCTA

Readout 12-0:
(SEQ ID NO: 32)
TTCTTCCCTCAATCTTCATC

Readout 13-1:
(SEQ ID NO: 33)
ACCCTTACTACTACATCATC

Readout 13-0:
(SEQ ID NO: 34)
AATCTCACCTTCCACTTCAC

Readout 14-1:
(SEQ ID NO: 35)
TCCTAACAACCAACTACTCC

Readout 14-0:
(SEQ ID NO: 36)
ACCTTTCTCCATACCCAACT

Readout 15-1:
(SEQ ID NO: 37)
TCTATCATTACCCTCCTCCT

Readout 15-0:
(SEQ ID NO: 38)
TCCTCATCTTACTCCCTCTA

Readout 16-1:
(SEQ ID NO: 39)
TATTCACCTTACAAACCCTC

Readout 16-0:
(SEQ ID NO: 40)
TCAAACTTTCCAACCACCTC

Readout 17-1:
(SEQ ID NO: 41)
TTACCTCTAACCCTCCATTC

Readout 17-0:
(SEQ ID NO: 42)
ACACCATTTATCCACTCCTC

Readout 18-1:
(SEQ ID NO: 43)
TCCCAACTAACCTAACATTC

Readout 18-0:
(SEQ ID NO: 44)
ACATCCTAACTACAACCTTC

Readout 19-1:
(SEQ ID NO: 45)
ATCCTCACTACATCATCCAC

Readout 19-0:
(SEQ ID NO: 46)
TCTCACACCACTTTCCTCAT

Readout 20-1:
(SEQ ID NO: 47)
TCCCTATCAATCTCCATAAC

Readout 20-0:
(SEQ ID NO: 48)
TTATCCATCCCTCTTCCTAC

Readout 21-1:
(SEQ ID NO: 49)
TCACCTCTAACTCATTACCT

Readout 21-0:
(SEQ ID NO: 50)
TCCTACAACATCCTTCCTAA

Readout 22-1:
(SEQ ID NO: 51)
ATCTCCCTTCTCTTCTCATA

Readout 22-0:
(SEQ ID NO: 52)
ATTACACCTCAACCCACACA

The various readout bits (Readout 1, Readout 2, Readout 3, ... Readout 22) were sequentially combined to produce the final sequence. So, for example, one barcode might have a structure:

Readout 1-1-Readout 2-0-Readout 3-0-...-Readout 22-1 and it would have the sequence:

(SEQ ID NO: 53)
ATCCTCCTTCAATACATCCC AAACACACACTAAACCACCCAACTCATCT

CAATCCTCCCA ... ATCTCCCTTCTCTTCTCATA and encode the binary word:

100 ... 1

All possible combinations of the 0 readout and the 1 readout for each bit ($2^{22}$ combinations, or over 4 million sequences) were used in the barcode library.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of correlating a genotype and a phenotype of a genetic variant, comprising:
   a) contacting a sample comprising a population of cells with a pool of nucleic acid constructs, wherein each construct comprises a sequence encoding a distinct variant operably linked to a barcode sequence encoding an N-bit binary barcode assigned to the distinct variant, wherein the barcode sequence comprises a pair of read sequences for each N position of the binary code wherein one of the read sequences of the pair is assigned to encode a value of "0" and the other read sequence of the pair is assigned to encode a value of "1";
   b) determining the phenotype, following expression of the nucleic acid construct, of the population of cells;
   c) contacting the sample with a plurality of readout probes comprising a fluorescent label, wherein the readout probes are configured to hybridize to one of the read sequences in each of the pair of read sequences of the expressed barcode sequence;
   d) imaging the readout probes bound to the expressed barcode sequence; and, repeating steps c) and d) in one or more sequential hybridization and imaging rounds until all N positions in the binary code have been imaged to determine the genotype; and
   e) determining the phenotype corresponding with the genotype.

2. The method of claim 1, wherein contacting the sample with the nucleic acid constructs comprises transfecting the nucleic acid constructs into the population of cells.

3. The method of claim 2, wherein the transfected cells are selected using antibiotic selection.

4. The method of claim 1, wherein the nucleic acid construct encodes at least two distinct variants.

5. The method of claim 1, wherein the barcode sequence encodes at least a 3-bit binary barcode and wherein each possible combination of the N-bit binary barcode is present within the pool of nucleic acid constructs.

6. The method of claim 1, wherein the barcode comprises an error-correcting code.

7. The method of claim 1, wherein cells having different phenotypes have different fluorescences when imaged.

8. The method of claim 1, wherein determining the phenotype of the cells comprises determining at least a portion of the transcriptome of the population of cells.

9. The method of claim 8, wherein determining the transcriptome comprises determining the transcriptome using multiplexed error robust fluorescence in situ hybridization (MERFISH).

10. The method of claim 1, wherein determining the phenotype of the cells comprises determining morphology of the cells.

11. The method of claim 1, wherein the pool of nucleic acid constructs encode a subset of possible single or multiple amino acid substitutions or deletions of a gene.

12. The method of claim 1, wherein the pool of nucleic acid constructs comprise interference RNA coding sequences.

13. The method of claim 1, wherein the barcode sequence comprises at least 10 unique sequences.

* * * * *

SEQUENCE LISTING

```
<160> NUMBER OF SEQ ID NOS: 53

<210> SEQ ID NO 1
<211> LENGTH: 124
<212> TYPE: PRT
<213> ORGANISM: Saccharomyces cerevisiae

<400> SEQUENCE: 1

Glu His Val Ala Phe Gly Ser Glu Asp Ile Glu Asn Thr Leu Ala Lys
1               5                   10                  15

Met Asp Asp Gly Gln Leu Asp Gly Leu Ala Phe Gly Ala Ile Gln Leu
            20                  25                  30

Asp Gly Asp Gly Asn Ile Leu Gln Tyr Asn Ala Ala Glu Gly Asp Ile
        35                  40                  45

Thr Gly Arg Asp Pro Lys Gln Val Ile Gly Lys Asn Phe Phe Lys Asp
    50                  55                  60
```

```
Val Ala Pro Gly Thr Asp Ser Pro Glu Phe Tyr Gly Lys Phe Lys Glu
 65                  70                  75                  80

Gly Val Ala Ser Gly Asn Leu Asn Thr Met Phe Glu Trp Met Ile Pro
                 85                  90                  95

Thr Ser Arg Gly Pro Thr Lys Val Lys Val His Met Lys Lys Ala Leu
            100                 105                 110

Ser Gly Asp Ser Tyr Trp Val Phe Val Lys Arg Val
            115                 120

<210> SEQ ID NO 2
<211> LENGTH: 372
<212> TYPE: DNA
<213> ORGANISM: Saccharomyces cerevisiae

<400> SEQUENCE: 2
gaacatgtgg cgtttggaag tgaggacatt gagaatacgc ttgcgaagat ggatgatggt      60
caactggatg gtcttgcctt tggagcaatt cagttggatg gcgatggtaa catcttgcag     120
tacaatgccg ccgagggtga tattacagga cgtgatccca acaagtgat tggaaaaaat      180 tttttcaaag atgtagcgcc tggcactgac tcacccgagt tttacggtaa gttcaaagaa     240
ggcgtggctt ccggtaatct taatacgatg tttgagtgga tgatccccac tagccgtgga     300
cccaccaagg tgaaagtgca tatgaagaag gccttatcgg gcgatagcta ctgggtgttc     360
gttaaacgtg tt                                                         372

<210> SEQ ID NO 3
<211> LENGTH: 124
<212> TYPE: PRT
<213> ORGANISM: Artificial Sequence
<220> FEATURE:
<223> OTHER INFORMATION: Synthetic polypeptide

<400> SEQUENCE: 3

Glu His Val Ala Phe Gly Ser Glu Asp Ile Glu Asn Thr Leu Ala Lys
  1               5                  10                  15

Met Asp Asp Gly Gln Leu Asp Gly Leu Ala Phe Gly Ala Ile Gln Leu
                 20                  25                  30

Asp Gly Asp Gly Asn Ile Leu Gln Tyr Asn Ala Ala Glu Gly Asp Ile
             35                  40                  45

Thr Gly Arg Asp Pro Lys Gln Val Ile Gly Lys Asn Leu Phe Lys Asp
     50                  55                  60

Val Ala Cys Gly Thr Arg Ser Ser Glu Phe Tyr Gly Lys Phe Lys Glu
 65                  70                  75                  80

Gly Val Ala Ser Gly Asn Leu Asn Thr Met Phe Glu Trp Met Ile Pro
                 85                  90                  95

Thr Ser Arg Gly Pro Thr Lys Val Lys Val His Met Lys Lys Ala Leu
            100                 105                 110

Ser Gly Asp Ser Tyr Trp Val Phe Val Lys Arg Val
            115                 120

<210> SEQ ID NO 4
<211> LENGTH: 372
<212> TYPE: DNA
<213> ORGANISM: Artificial Sequence
<220> FEATURE:
<223> OTHER INFORMATION: Synthetic polynucleotide

<400> SEQUENCE: 4
```

```
gaacatgtgg cgtttggaag tgaggacatt gagaatacgc ttgcgaagat ggatgatggt    60
caactggatg gtcttgcctt tggagcaatt cagttggatg gcgatggtaa catcttgcag   120
tacaatgccg ccgagggtga tattacagga cgtgatccca acaagtgat tggaaaaaat   180 ctgttcaaag atgtagcgtg cggcactcgt tcaagcgagt tttacggtaa gttcaaagaa   240
ggcgtggctt ccggtaatct taatacgatg tttgagtgga tgatccccac tagccgtgga   300
cccaccaagg tgaaagtgca tatgaagaag gccttatcgg cgatagcta ctgggtgttc   360 gttaaacgtg tt                                                       372
```

<210> SEQ ID NO 5
<211> LENGTH: 237
<212> TYPE: PRT
<213> ORGANISM: Artificial Sequence
<220> FEATURE:
<223> OTHER INFORMATION: Synthetic polypeptide

<400> SEQUENCE: 5

```
Met Val Ser Lys Gly Glu Glu Leu Ile Lys Glu Asn Met His Met Lys
1               5                   10                  15

Leu Tyr Met Glu Gly Thr Val Asp Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Leu Tyr Gly Ser Lys Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Thr Ser Asn Gly Pro Val Met Gln Lys Lys Thr Leu Gly Trp
    130                 135                 140

Glu Ala Phe Thr Glu Thr Leu Tyr Pro Ala Asp Gly Gly Leu Glu Gly
145                 150                 155                 160

Arg Asn Asp Met Ala Leu Lys Leu Val Gly Gly Ser His Leu Ile Ala
                165                 170                 175

Asn Ala Lys Thr Thr Tyr Arg Ser Lys Lys Pro Ala Lys Asn Leu Lys
            180                 185                 190

Met Pro Gly Val Tyr Tyr Val Asp Tyr Arg Leu Glu Arg Ile Lys Glu
        195                 200                 205

Ala Asn Asn Glu Thr Tyr Val Glu Gln His Glu Val Ala Val Ala Arg
    210                 215                 220

Tyr Cys Asp Leu Pro Ser Lys Leu Gly His Lys Leu Asn
225                 230                 235
```

<210> SEQ ID NO 6
<211> LENGTH: 711
<212> TYPE: DNA
<213> ORGANISM: Artificial Sequence
<220> FEATURE:
<223> OTHER INFORMATION: Synthetic polynucleotide

<400> SEQUENCE: 6

-continued

```
atggtgtcta aaggagagga acttatcaaa gaaaatatgc acatgaagct ttacatggaa    60
ggaacagtgg acaatcacca ttttaaatgt acatcagaag gcgagggtaa accttatgag   120
gggacgcaaa ccatgcgtat caaggtcgta gagggcggcc ctttgccttt cgctttcgac   180
attcttgcaa cctcattctt gtatggctcc aagactttta tcaaccatac acaaggcatt   240
cccgatttct ttaaacaatc gttccctgaa ggttttacat gggaacgtgt aacaacatat   300
gaagatgggg gagttttaac tgccacacag gatacatctt tacaggatgg ctgcctgatc   360
tataatgtaa agatccgtgg agtgaacttt acctcgaacg gccccgtcat gcagaaaaag   420
acccttgggt gggaggcctt tacggaaacg ctttaccccg cggacggagg tctggaagga   480
cgtaatgaca tggcgctgaa gcttgtcgga ggatcccatc tgatcgcaaa tgctaagacc   540
acctatcgta gcaagaaacc tgctaaaaac ttaaaaatgc ctggtgttta ctacgtggac   600
tatcgtcttg agcgtattaa ggaggcaaat aacgaaacct atgttgaaca cacgaggtc   660 gctgtggccc gctattgcga cttgccctcg aagctggggc ataagttgaa t            711
```

<210> SEQ ID NO 7
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 7

```
Val Ser Lys Gly Glu Glu Thr Ile Met Ser Val Ile Lys Pro Asp Met
1               5                   10                  15

Lys Ile Lys Leu Arg Met Glu Gly Asn Val Asn Gly His Ala Phe Val
            20                  25                  30

Ile Glu Gly Glu Gly Ser Gly Lys Pro Phe Glu Gly Ile Gln Thr Ile
        35                  40                  45

Asp Leu Glu Val Lys Glu Gly Ala Pro Leu Pro Phe Ala Tyr Asp Ile
    50                  55                  60

Leu Thr Thr Ala Phe His Tyr Gly Asn Arg Val Phe Thr Lys Tyr Pro
65                  70                  75                  80

Arg Lys Ile Pro Asp Tyr Phe Lys Gln Ser Phe Pro Glu Gly Tyr Ser
                85                  90                  95

Trp Glu Arg Ser Met Thr Tyr Glu Asp Gly Gly Ile Cys Asn Ala Thr
            100                 105                 110

Asn Asp Ile Thr Met Glu Glu Asp Ser Phe Ile Asn Lys Ile His Phe
        115                 120                 125

Lys Gly Thr Asn Phe Pro Pro Asn Gly Pro Val Met Gln Lys Arg Thr
    130                 135                 140

Val Gly Trp Glu Val Ser Thr Glu Lys Met Tyr Val Arg Asp Gly Val
145                 150                 155                 160

Leu Lys Gly Asp Val Lys Met Lys Leu Leu Lys Gly Gly Ser His
                165                 170                 175

Tyr Arg Cys Asp Phe Arg Thr Thr Tyr Lys Val Lys Gln Lys Ala Val
            180                 185                 190

Lys Leu Pro Lys Ala His Phe Val Asp His Arg Ile Glu Ile Leu Ser
        195                 200                 205

His Asp Lys Asp Tyr Asn Lys Val Lys Leu Tyr Glu His Ala Val Ala
    210                 215                 220

Arg Asn Ser Thr Asp Ser Met Asp Glu Leu Tyr Lys
225                 230                 235
```

<210> SEQ ID NO 8
<211> LENGTH: 708
<212> TYPE: DNA
<213> ORGANISM: Artificial Sequence
<220> FEATURE:
<223> OTHER INFORMATION: Synthetic polynucleotide

<400> SEQUENCE: 8

```
gttagcaagg gcgaggagac catcatgagc gtgatcaagc cggacatgaa gatcaagctg      60
cgcatggagg gcaacgtgaa cggccatgcc tttgtgatcg agggcgaggg cagcggtaag     120
ccgtttgagg gcatccagac catcgacctg gaggttaagg aaggcgcacc gctgccgttt     180
gcctacgaca tcctgaccac cgcattccac tacggcaacc gcgtgttcac caagtacccg     240
cgcaagatcc cggactactt caagcagagc ttcccggagg gctacagttg ggaacgcagc     300
atgacctacg aggacggcgg tatctgcaac gccaccaacg acatcaccat ggaagaagat     360
agcttcatca acaagatcca cttcaagggc acaaacttcc cgccgaatgg tccggttatg     420
cagaagcgca ccgttggctg ggaggtgagc accgagaaga tgtatgtgcg cgacggtgtg     480
ctgaagggcg acgtgaagat gaagctgctg ctgaagggtg gcagccacta ccgctgcgac     540
ttccgcacca cctacaaagt taagcaaaag gcagtgaagt taccgaaggc ccacttcgtg     600
gaccaccgca tcgaaatcct gagccacgac aaggactata acaaagtgaa gctgtacgag     660
cacgccgtgg cccgtaacag caccgacagc atggatgagc tgtacaaa                708
```

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9

```
atcctccttc aatacatccc                                                  20
```

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10

```
tatctcatca atcccacact                                                  20
```

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11

```
acactaccac catttcctat                                                  20
```

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
aaacacacac taaaccaccc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
actccactac tactcactct                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
aactcatctc aatcctccca                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
accctctaac ttccatcaca                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
aatactctcc cacctcaact                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
accacaaccc attcctttca                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
tctatcatct ccaaaccaca                                              20

<210> SEQ ID NO 19
<211> LENGTH: 20
<212> TYPE: DNA

```
<213> ORGANISM: Artificial Sequence
<220> FEATURE:
<223> OTHER INFORMATION: Synthetic polynucleotide

<400> SEQUENCE: 19
tttctaccac taatcaaccc                                                   20

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20
tccaactcat ctctaatctc                                                   20

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
accctttaca aacacaccct                                                   20

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
ttcctaacaa atcacatccc                                                   20

<210> SEQ ID NO 23
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 23
tcctattctc aacctaacct                                                   20

<210> SEQ ID NO 24
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 24
ataaatcatt cccactaccc                                                   20

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
tatccttcaa tccctccaca                                                   20
```

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26
acccaacact cataacatcc                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27
acattacacc tcattctccc                                                    20

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28
tactacaaac ccataatccc                                                    20

<210> SEQ ID NO 29
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 29
tttactccct acacctccaa                                                    20

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
actttccaca tactatccca                                                    20

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
ttctccctct atcaactcta                                                    20

<210> SEQ ID NO 32
<211> LENGTH: 20
<212> TYPE: DNA
<213> ORGANISM: Artificial Sequence
<220> FEATURE:

```
<223> OTHER INFORMATION: Synthetic polynucleotide

<400> SEQUENCE: 32
ttcttccctc aatcttcatc                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 33
acccttacta ctacatcatc                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 34
aatctcacct tccacttcac                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 35
tcctaacaac caactactcc                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 36
acctttctcc atacccaact                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 37
tctatcatta ccctcctcct                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 38
tcctcatctt actccctcta                                              20
```

```
<210> SEQ ID NO 39
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 39
tattcacctt acaaaccctc                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 40
tcaaactttc caaccacctc                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 41
ttacctctaa ccctccattc                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 42
acaccattta tccactcctc                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 43
tcccaactaa cctaacattc                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 44
acatcctaac tacaacccttc                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic polynucleotide
```

<400> SEQUENCE: 45
atcctcacta catcatccac            20

<210> SEQ ID NO 46
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 46
tctcacacca ctttcctcat            20

<210> SEQ ID NO 47
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 47
tccctatcaa tctccataac            20

<210> SEQ ID NO 48
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 48
ttatccatcc ctcttcctac            20

<210> SEQ ID NO 49
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 49
tcacctctaa ctcattacct            20

<210> SEQ ID NO 50
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 50
tcctacaaca tccttcctaa            20

<210> SEQ ID NO 51
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 51
atctcccttc tcttctcata            20

<210> SEQ ID NO 52
<211> LENGTH: 20

```
<212> TYPE: DNA
<213> ORGANISM: Artificial Sequence
<220> FEATURE:
<223> OTHER INFORMATION: Synthetic polynucleotide

<400> SEQUENCE: 52
attacacctc aacccacaca                                           20

<210> SEQ ID NO 53
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 53
atcctccttc aatacatccc aaacacacac taaaccaccc aactcatctc aatcctccca    60
atctcccttc tcttctcata                                           80
```